(12) United States Patent
Behrens et al.

(10) Patent No.: US 8,524,465 B2
(45) Date of Patent: Sep. 3, 2013

(54) AGONISTS OF BITTER TASTE RECEPTORS AND USES THEREOF

(75) Inventors: Maik Behrens, Nuthetal (DE); Anne Brockhoff, Potsdam (DE); Christina Kuhn, Nuthetal (DE); Wolfgang Meyerhof, Norderstedt (DE); Giovanni Appendino, Novara (IT)

(73) Assignee: Deutsches Institut fuer Ernaehrungsforschung Potsdam-Rehbruecke, Nuthetal (DE)

( * ) Notice: Subject to any disclaimer, the term of this patent is extended or adjusted under 35 U.S.C. 154(b) by 0 days.

(21) Appl. No.: 13/584,592

(22) Filed: Aug. 13, 2012

(65) Prior Publication Data

US 2012/0309703 A1 Dec. 6, 2012

Related U.S. Application Data

(62) Division of application No. 12/593,479, filed as application No. PCT/EP2008/002529 on Mar. 31, 2008, now Pat. No. 8,309,314.

(60) Provisional application No. 60/921,157, filed on Mar. 29, 2007.

(30) Foreign Application Priority Data

Mar. 29, 2007 (EP) ..................................... 07006595

(51) Int. Cl.
*G01N 33/567* (2006.01)
*C07K 14/705* (2006.01)

(52) U.S. Cl.
USPC ........................... 435/7.21; 435/7.2; 436/501

(58) Field of Classification Search
None
See application file for complete search history.

(56) References Cited

U.S. PATENT DOCUMENTS

2006/0275765 A1  12/2006  Slack et al.

FOREIGN PATENT DOCUMENTS

WO      03006482      1/2003
WO    2004029087      4/2004

OTHER PUBLICATIONS

International Search Report for PCT/EP2008/002529, dated Nov. 25, 2008 (9 pages).
Behrens, M et al., "The human taste receptor hTAS2R14 responds to a variety of different bitter compounds", 2 Biochemical and Biophysical Research Communications, Academic Press Inc. Orlando, FL, 0 US, vol. 319, No. 2, Jun. 25, 2004, pp. 479-485, XP004512461, ISSN: 0006-291X.
Guinard Jean-Xavier et al., "Chemoreception and perception of the bitterness of isohumulones", Physiology and Behavior, vol. 56, No. 6, 1994, pp. 1257-1263, XP002505253, ISSN: 0031-9384.

*Primary Examiner* — John Ulm
(74) *Attorney, Agent, or Firm* — Baker, Donelson, Bearman, Caldwell & Berkowitz, PC

(57) ABSTRACT

The present invention relates to agonists of the human bitter-taste receptors hTAS2R14, hTAS2R10 and hTAS2R4 and their role in bitter taste transduction. The invention also relates to methods for identifying molecules that modulate, e.g. suppress, or enhance hTAS2R14, hTAS2R10 and hTAS2R4 bitter taste transduction or bitter taste response.

11 Claims, 3 Drawing Sheets

AGONISTS OF BITTER TASTE RECEPTORS AND USES THEREOF

CROSS REFERENCE TO RELATED APPLICATIONS

Figure 1:
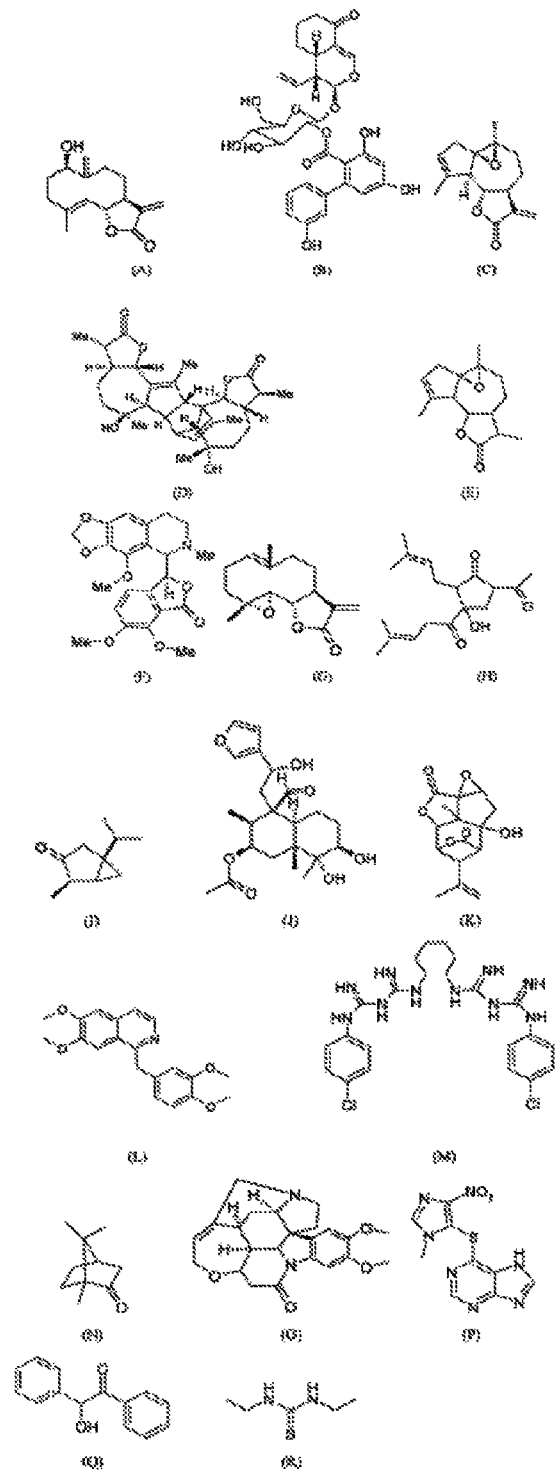

This application is a Divisional of U.S. application Ser. No. 12/593,479, filed Sep. 28, 2009, which is a §371 National Stage Application of PCT/EP2008/002529, filed Mar. 31, 2008, which claims priority to European Application 07006595.8, filed Mar. 29, 2007, and U.S. Application No. 60/921,157, filed Mar. 29, 2007, the contents of each are hereby incorporated by reference in their entireties.

FIELD OF THE INVENTION

The present invention relates to agonists of the human bitter-taste receptors hTAS2R14, hTAS2R10 and hTAS2R4 and their role in bitter taste transduction. The invention also relates to methods for identifying molecules that modulate, e.g. suppress, or enhance hTAS2R14, hTAS2R10 and hTAS2R4 bitter taste transduction or bitter taste response.

BACKGROUND OF THE INVENTION

Investigators have recently turned their attention to understanding the biological mechanisms of taste, and in particular bitter taste. For a review of the literature see, for example, Caicedo A. and Roper S D. (2001) Science 291: 1557-1560; Dulac C. (2000) Cell 100: 607-610; Kinnamon S. C. (2000) Neuron 25: 507-510; Lindemann B. (2001) Nature 413: 219-225; and Margolskee R F. (2001) J. Biol. Chem. 277: 1-4.

Bitter taste is aversive, and as such provides humans with a mechanism of protection against poisonous substances, which are generally bitter-tasting compounds. More subtly, bitter-tastants also affect the palatability of food, beverages, thereby influencing human nutritional habits as is more fully discussed by Drewnowski in "The Science and Complexity of Bitter Taste", (2001) Nutr. Rev. 59: 163-169. They also affect the palatability of other ingestibles such as orally administered pharmaceuticals and nutraceuticals. Understanding the mechanism of bitter taste transduction has implications for the food and pharmaceutical industries. If the bitter taste transduction pathway can be manipulated, it may be possible to suppress or eliminate bitter taste to render foods more palatable and increase patient compliance with oral pharmaceutics.

Taste transduction involves the interaction of molecules, i.e. tastants with taste receptor-expressing cells which reside in the taste buds located in the papillae of the tongue. Taste buds relay information to the brain on the nutrient content of food and the presence of poisons. Recent advances in biochemical and physiological studies have enabled researchers to conclude that bitter taste transduction is mediated by so-called G-protein coupled receptors (GPCRs). GPCRs are 7 transmembrane domain cell surface proteins that amplify signals generated at a cell surface when the receptor interacts with a ligand (a tastant) whereupon they activate heterotrimeric G-proteins. The G-proteins are protein complexes that are composed of alpha and beta-gamma sub-units. They are usually referred to by their alpha subunits and classified generally into 4 groups: G alpha s, i, q and 12. The G alpha q type couple with GPCRs to activate phospholipase C which leads to an increase in cellular $Ca^{2+}$. There are many Gq-type G-proteins that are promiscuous and can couple to GPCRs, including taste receptors, and these so-called "promiscuous" G-proteins are well known in the art. These G-proteins dissociate into alpha and beta-gamma subunits upon activation, resulting in a complex cascade of cellular events that results in the cell producing second messengers, such as calcium ions, that enable the cells to send a signal to the brain indicating a bitter response.

There is also anatomical evidence that GPCRs mediate bitter taste transduction: clusters of these receptors are found in mammalian taste cells containing gustducin. Gustducin is a G-protein subunit that is implicated in the perception of bitter taste in mammals see, for example, Chandrashekar, J. et al (2000) Cell 100: 703-711; Matsunami H. et al. (2000) Nature 404: 601-604; or Adler E. et al. (2000) Cell 100: 693-702. cDNAs encoding such GPCRs have been identified, isolated, and used as templates to compare with DNA libraries using in-silico data-mining techniques to identify other related receptors. In this manner it has been possible to identify a family of related receptors, the so-called T2R or TAS2R family of receptors, that have been putatively assigned as bitter taste receptors.

Humans are able to detect with a limited genetic repertoire of about 30 receptor genes thousands of different bitter compounds. Since their discovery in the year 2000 (Adler E. et al. (2000) supra; Chandrashekar J. et al. (2000) supra; Matsunami H. et al (2000) supra) only few mammalian TAS2Rs have been deorphanised, i.e. ligands, in particular agonists have been identified. The murine mTAS2R5 (Chandrashekar J. et al (2000) supra) and the rat rTAS2R9 (Bufe B. et al. (2002) Nature Genetics 32:397-401) respond to the toxic bitter substance cycloheximide, the mouse mTAS2R8 and the human hTAS2R4 respond to high doses of denatonium and, to a lesser extend, to 6-n-propyl-2-thiouracil (Chandrashekar J. et al. (2000) supra), the human hTAS2R10 and hTAS2R16 respond selectively to strychnine and bitterglucopyranosides, respectively (Bufe B. et al (2002) supra). Although for some TAS2Rs a limited promiscuity (mTAS2R8, hTAS2R4) or specificity for a group of chemically related compounds (hTAS2R16) was reported, the relative selectivity of ligand recognition by the receptors published to date does, by far, not explain the enormous number of bitter tastants recognised by the mammalian gustatory system. There are several possible mechanisms conceivable to increase the number of tastants recognised by a limited number of taste receptor genes, the simplest way would be to have receptors which exhibit a broad tuning to a great number of structurally divergent ligands.

As stated before, thousands of different bitter compounds can elicit bitter taste. Consequently, not all bitter tasting substances can be prevented to elicit bitter taste by blocking only a small subset of receptors within the bitter taste receptor family. In order to carry out a method for isolating additional agonists or antagonists to complement already known ones, it is therefore necessary to deorphanize bitter taste receptors and gain insight in what particular agonists are targeting the receptors for which no agonists or antagonists are known. The knowledge about the receptor specificity for a given agonist is prerequisite to the implementation of a method to isolate structurally related agonists or antagonists which may be at least as potent in activating or suppressing the bitter taste receptor activity as the original compound and which may feature additional advantages such as lower toxicity, better solubility, improved stability and so forth. A bitter taste receptor agonist isolated by such method can furthermore be utilized to identify a respective antagonist for the same receptor. Furthermore, agonists and antagonists can be isolated and modified in such a way that they are capable of targeting a broader range of known bitter taste receptors with high affinity to achieve a more effective enhancement or suppression of bitter taste.

In addition to the deorphanization of the human bitter taste receptor hTAS2R4, the present inventors teach that the human bitter taste receptors hTAS2R14, hTAS2R10 and hTAS2R4, respond to specific bitter compounds, namely, to a bitter compound selected from the group consisting of absinthin, artemorin, arglabin, azathioprine, azepinon, benzoin, brucine, camphor, chlorhexidine, N,N'-diethylthiourea, herbolid A, isohumulone, noscapine, parthenolid, or arborescin for hTAS2R14; to a bitter compound selected from the group consisting of absinthin, artemorin, amarogentin, arglabin, azathioprine, benzoin, camphor, cascarillin, papaverin, parthenolid, picrotoxinin, arborescin or (−)-a-thujon for hTAS2R10; or to a bitter compound selected from the group consisting of artemorin, amarogentin, azathioprine or campor for hTAS2R4. Therefore, the disclosure of the present patent application allows the implementation of a method to isolate effective agonists or antagonists for particularly these receptors.

DESCRIPTION OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Klbl, H. eds. (1995), Helvetica Chimica Acta, CH-4010 Basel, Switzerland).

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps. In the following passages different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

In the following definitions of the terms: alkyl, heteroalkyl, cycloalkyl, heterocycloalkyl, alicyclic system, aryl, aralkyl, heteroaryl, heteroaralkyl, alkenyl and alkynyl are provided. These terms will in each instance of its use in the remainder of the specification have the respectively defined meaning and preferred meanings.

The term "alkyl" refers to a saturated straight or branched carbon chain. Preferably, the chain comprises from 1 to 10 carbon atoms, i.e. 1, 2, 3, 4, 5, 6, 7, 8, 9 or 10 e.g. methyl, ethyl methyl, ethyl, propyl, iso-propyl, butyl, iso-butyl, tert-butyl, pentyl, hexyl, heptyl, or octyl. Alkyl groups are optionally substituted.

The term "heteroalkyl" refers to a saturated straight or branched carbon chain. Preferably, the chain comprises from 1 to 9 carbon atoms, i.e. 1, 2, 3, 4, 5, 6, 7, 8, 9 e.g. methyl, ethyl, propyl, iso-propyl, butyl, iso-butyl, sec-butyl, tert-butyl, pentyl, hexyl, heptyl, octyl, which is interrupted one or more times, e.g. 1, 2, 3, 4, 5, with the same or different heteroatoms. Preferably the heteroatoms are selected from O, S, and N, e.g. —O—$CH_3$, —S—$CH_3$, —$CH_2$—O—$CH_3$, —$CH_2$—O—$C_2H_5$, —$CH_2$—S—$CH_3$, —$CH_2$—S—$C_2H_5$, —$C_2H_4$—O—$CH_3$, —$C_2H_4$—O—$C_2H_5$, —$C_2H_4$—S—$CH_3$, —$C_2H_4$—S—$C_2H_5$ etc. Heteroalkyl groups are optionally substituted.

The terms "cycloalkyl" and "heterocycloalkyl", by themselves or in combination with other terms, represent, unless otherwise stated, cyclic versions of "alkyl" and "heteroalkyl", respectively, with preferably 3, 4, 5, 6, 7, 8, 9 or 10 atoms forming a ring, e.g. cyclopropyl, cyclobutyl, cyclopentyl, cyclohexyl, cycloheptyl, cyclooctyl etc. The terms "cycloalkyl" and "heterocycloalkyl" are also meant to include bicyclic, tricyclic and polycyclic versions thereof. If more than one cyclic ring is present such as in bicyclic, tricyclic and polycyclic versions, then these rings may also comprise one or more aryl- or heteroaryl ring. The term "heterocycloalkyl" preferably refers to a saturated ring having five members of which at least one member is a N, O or S atom and which optionally contains one additional O or one additional N; a saturated ring having six members of which at least one member is a N, O or S atom and which optionally contains one additional O or one additional N or two additional N atoms; or a saturated bicyclic ring having nine or ten members of which at least one member is a N, O or S atom and which optionally contains one, two or three additional N atoms. "Cycloalkyl" and "heterocycloalkyl" groups are optionally substituted. Additionally, for heterocycloalkyl, a heteroatom can occupy the position at which the heterocycle is attached to the remainder of the molecule. Preferred examples of cycloalkyl include $C_3$-$C_{10}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantly, or decahydro-naphthalenyl. Preferred examples of heterocycloalkyl include $C_3$-$C_{10}$-heterocycloalkyl, in particular 1-(1,2,5,6-tetrahydropyridyl), 1-piperidinyl, 2-piperidinyl, 3-piperidinyl, 4-morpholinyl, 3-morpholinyl, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuran-3-yl, tetrahydrothien-2-yl, tetrahydrothien-3-yl, 1-piperazinyl, 2-piperazinyl, and the like.

The term "alicyclic system" refers to mono, bicyclic, tricyclic or polycyclic version of a cycloalkyl or heterocycloalkyl comprising at least one double and/or triple bond. However, an alicyclic system is not aromatic or heteroaromatic, i.e. does not have a system of conjugated double bonds/ free electron pairs. Thus, the number of double and/or triple bonds maximally allowed in an alicyclic system is determined by the number of ring atoms, e.g. in a ring system with up to 5 ring atoms an alicyclic system comprises up to one double bond, in a ring system with 6 ring atoms the alicyclic system comprises up to two double bonds. Thus, the "cycloalkenyl" as defined below is a preferred embodiment of an alicyclic ring system. Alicyclic systems are optionally substituted. Alicyclic systems comprise one, two, three or more heteroatoms, independently selected from the group consisting of nitrogen, sulphur and oxygen.

The term "aryl" preferably refers to an aromatic monocyclic ring containing 6 carbon atoms, an aromatic bicyclic ring system containing 10 carbon atoms or an aromatic tricyclic ring system containing 14 carbon atoms. Examples are phenyl, naphtyl or anthracenyl. The aryl group is optionally substituted.

The term "aralkyl" refers to an alkyl moiety, which is substituted by aryl, wherein alkyl and aryl have the meaning as outlined above. An example is the benzyl radical. Preferably, in this context the alkyl chain comprises from 1 to 8 carbon atoms, i.e. 1, 2, 3, 4, 5, 6, 7, or 8, e.g. methyl, ethyl methyl, ethyl, propyl, iso-propyl, butyl, iso-butyl, sec-butenyl, tert-butyl, pentyl, hexyl, pentyl, octyl. The aralkyl group is optionally substituted at the alkyl and/or aryl part of the group.

The term "heteroaryl" preferably refers to a five or six-membered aromatic monocyclic ring wherein at least one of the carbon atoms are replaced by 1, 2, 3, or 4 (for the five membered ring) or 1, 2, 3, 4, or 5 (for the six membered ring) of the same or different heteroatoms, preferably selected from O, N and S; an aromatic bicyclic ring system wherein 1, 2, 3, 4, 5, or 6 carbon atoms of the 8, 9, 10, 11 or 12 carbon atoms have been replaced with the same or different heteroatoms, preferably selected from O, N and S; or an aromatic tricyclic ring system wherein 1, 2, 3, 4, 5, or 6 carbon atoms of the 13, 14, 15, or 16 carbon atoms have been replaced with the same or different heteroatoms, preferably selected from O, N and S. Examples are oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothiophenyl, 2-benzothiophenyl, 1H-indazolyl, benzimidazolyl, benzoxazolyl, indoxazolyl, 2,1-benzisoxazoyl, benzothiazolyl, 1,2-benzisothiazolyl, 2,1-benzisothiazolyl, benzotriazolyl, quinolinyl, isoquinolinyl, quinoxalinyl, quinazolinyl, 1,2,3-benzotriazinyl, or 1,2,4-benzotriazinyl.

The term "heteroaralkyl" refers to an alkyl moiety, which is substituted by heteroaryl, wherein alkyl and heteroaryl have the meaning as outlined above. An example is the 2-alklypyridinyl, 3-alkylpyridinyl, or 2-methylpyridinyl. Preferably, in this context the alkyl chain comprises from 1 to 8 carbon atoms, i.e. 1, 2, 3, 4, 5, 6, 7, or 8, e.g. methyl, ethyl methyl, ethyl, propyl, iso-propyl, butyl, iso-butyl, sec-butenyl, tert-butyl, pentyl, hexyl, pentyl, octyl. The heteroaralkyl group is optionally substituted at the alkyl and/or heteroaryl part of the group.

The terms "alkenyl" and "cycloalkenyl" refer to olefinic unsaturated carbon atoms containing chains or rings with one or more double bonds. Examples are propenyl and cyclohexenyl. Preferably, the alkenyl chain comprises from 2 to 8 carbon atoms, i.e. 2, 3, 4, 5, 6, 7, or 8, e.g. ethenyl, 1-propenyl, 2-propenyl, iso-propenyl, 1-butenyl, 2-butenyl, 3-butenyl, iso-butenyl, sec-butenyl, 1-pentenyl, 2-pentenyl, 3-pentenyl, 4-pentenyl, hexenyl, heptenyl, octenyl. The term also comprises $CH_2$, i.e. methenyl, if the substituent is directly bonded via a double bond to the carbon atom to which it is attached. Preferably the cycloalkenyl ring comprises from 3 to 14 carbon atoms, i.e. 3, 4, 5, 6, 7, 8, 9, 10, 11, 12, 13 or 14, e.g. cyclopropenyl, cyclobutenyl, cyclopentenyl, cyclohexenyl, cycloheptenyl, cyclooctyl, cyclononenyl, cyclodecenyl, spiro[3,3]heptenyl, spiro[3,4]octenyl, spiro[4,3]octenyl, spiro[3,5]nonenyl, spiro[5,3]nonenyl, spiro[3,6]decenyl, spiro[6,3]decenyl, spiro[4,5]decenyl, spiro[5,4]decenyl, bicyclo[4.1.0]heptenyl, bicyclo[3.2.0]heptenyl, bicyclo[2.2.1]heptenyl, bicyclo[2.2.2]octenyl, bicyclo[5.1.0]octenyl, bicyclo[4.2.0]octenyl, hexahydro-pentalenyl, hexahydro-indenyl, octahydro-azulenyl, or octahydro-naphthalenyl.

The term "alkynyl" refers to unsaturated carbon atoms containing chains or rings with one or more triple bonds. An example is the propargyl radical. Preferably, the alkynyl chain comprises from 2 to 8 carbon atoms, i.e. 2, 3, 4, 5, 6, 7, or 8, e.g. ethynyl, 1-propynyl, 2-propynyl, 1-butynyl, 2-butynyl, 3-butynyl, 1-pentynyl, 2-pentynyl, 3-pentynyl, 4-pentynyl, hexynyl, pentynyl, octynyl.

The term "optionally substituted" in each instance if not further specified preferably refers to halogen, preferably, F, Cl, or Br, —$NO_2$, —CN, —OR', —NR'R", —COOR', —CONR'R", —NR'"COR'", —NR'"COR'", =O, =S, —NR'"CONR'R", —NR'"SO$_2$A, —COR'", —SO$_2$NR'R", —OOCR'", —CR'"R'"OH, R'"OH, and -E or two substituents at adjacent carbon moieties or heteromoieties, as the case may be, form a cycloalkyl, heterocycloalkly, alicyclic system, aryl or heteroaryl;

R' and R" is each independently selected from the group consisting of hydrogen, alkyl, alkenyl, alkynyl, cycloalkyl, heterocycloalkyl, aryl, heteroaryl, and aralkyl or together form a heteroaryl, or heterocycloalkyl;

R'" and R"" is each independently selected from the group consisting of hydrogen, alkyl, alkenyl, alkynyl, cycloalkyl, heterocycloalkyl, alkoxy, aryl, aralkyl, heteroaryl, and —NR'R"; E is selected from the group consisting of alkyl, alkenyl, cycloalkyl, alkoxy, alkoxyalkyl, heterocycloalkyl, an alicyclic system, aryl and heteroaryl; optionally substituted;

The present inventors have identified an agonist of the human hTAS2R14 (DNA sequence according to SEQ ID NO: 1 and amino acid sequence according to SEQ ID NO: 2), hTAS2R10 (DNA sequence according to SEQ ID NO: 3 and amino acid sequence according to SEQ ID NO: 4) and hTAS2R4 (DNA sequence according to SEQ ID NO: 5 and amino acid sequence according to SEQ ID NO: 6) bitter taste receptors, and have found that they respond with specificity toward the following bitter substances: absinthin, artemorin, arglabin, azathioprine, azepinon, benzoin, brucine, camphor, chlorhexidine, N,N'-diethylthiourea, herbolid A, isohumulone, noscapine, parthenolid, or arborescin for hTAS2R14; absinthin, artemorin, amarogentin, arglabin, azathioprine, benzoin, camphor, cascarillin, papaverin, parthenolid, picrotoxinin, arborescin and (−)-a-thujon for hTAS2R10; and artemorin, amarogentin, azathioprine or campor for hTAS2R4—an important finding for the food and pharmaceutical industries. The agonist provided by the present inventors enables the skilled person to design intelligent compound libraries to screen for antagonists to the bitter response of these receptors, which in turn enables the development of compounds and compositions to suppress or eliminate bitter tasting components of foods, in particular animal foods, nutrients and dietary supplements and pharmaceutical or homeopathic preparations containing such phytochemicals. Similarly, the invention also enables the skilled person to screen for additional structurally related agonists, or to screen for compounds that enhance a bitter response, such as might be useful in the food industry and in the production of animal repellents. Therefore, in one aspect the present invention provides a method for isolating an antagonist of hTAS2R14, hTAS2R10 or hTAS2R4 bitter taste receptor activity, wherein the bitter taste receptor is encoded by a polynucleotide selected from the group consisting of:

(a) polynucleotide encoding at least the mature form of the polypeptide having the amino acid sequence as shown in SEQ ID NO: 2, 4, or 6;
(b) polynucleotide having the coding nucleotide sequence as shown in SEQ ID NO: 1, 3, or 5 encoding at least the mature form of the polypeptide;
(c) polynucleotide encoding a fragment or derivative of a polypeptide encoded by a polynucleotide of any one of (a) to (b), wherein in said derivative one or more amino acid residues are conservatively substituted compared to said polypeptide, and said fragment or derivative has hTAS2R14, hTAS2R10 and hTAS2R4 bitter taste receptor activity, respectively;
(d) polynucleotide which is an ortholog of the polynucleotide sequences shown in SEQ ID NO: 1, 3, or 5 encoding at least the mature form of the corresponding bitter taste receptor;
(e) polynucleotide which encodes a polypeptide having hTAS2R14, hTAS2R10 or hTAS2R4 bitter taste receptor activity, and where said polypeptide is at least 80% identical to a polypeptide as shown in SEQ ID NO: 2, 4, and 6, respectively;

comprising the steps:
(1) contacting a bitter taste receptor encoded by said polynucleotide or a host cell genetically engineered with said polynucleotide or with a vector containing said polynucleotide to express said bitter taste receptor with a potential antagonist; and
(2) determining whether the potential antagonist inhibits the bitter taste receptor activity, wherein prior, concomitantly and/or after step (1) said bitter taste receptor or said host cell is contacted with an agonist selected from the group consisting of absinthin, artemorin, arglabin, azathioprine, azepinon, benzoin, brucine, camphor, chlorhexidine, N,N'-diethylthiourea, herbolid A, isohumulone, noscapine, parthenolid, or arborescin agonistic derivatives or structurally related agonists thereof for hTAS2R14; selected from the group consisting of absinthin, artemorin, amarogentin, arglabin, azathioprine, benzoin, camphor, cascarillin, papaverin, parthenolid, picrotoxinin, arborescin or (-)-a-thujon and agonistic derivatives or structurally related agonists thereof for hTAS2R10; or selected from the group consisting of artemorin, amarogentin, azathioprine or campor and agonistic derivatives or structurally related agonists thereof for hTAS2R4.

In a further aspect the present invention provides a method for isolating an agonist of hTAS2R14, hTAS2R10 or hTAS2R4 bitter taste receptor activity, wherein the bitter taste receptor is encoded by a polynucleotide selected from the group consisting of:

(a) polynucleotide encoding at least the mature form of the polypeptide having the amino acid sequence as shown in SEQ ID NO: 2, 4, or 6;
(b) polynucleotide having the coding nucleotide sequence as shown in SEQ ID NO: 1, 3, or 5 encoding at least the mature form of the polypeptide;
(d) polynucleotide encoding a fragment or derivative of a polypeptide encoded by a polynucleotide of any one of (a) to (b), wherein in said derivative one or more amino acid residues are conservatively substituted compared to said polypeptide, and said fragment or derivative has hTAS2R14, hTAS2R10 and hTAS2R4 bitter taste receptor activity, respectively;
(d) polynucleotide which is an ortholog of the polynucleotide sequences shown in SEQ ID NO: 1, 3, or 5 encoding at least the mature form of the corresponding bitter taste receptor;
(e) polynucleotide which encodes a polypeptide having hTAS2R14, hTAS2R10 or hTAS2R4 bitter taste receptor activity, and where said polypeptide is at least 80% identical to a polypeptide as shown in SEQ ID NO: 2, 4, and 6, respectively;

comprising the steps:
(1) contacting a bitter taste receptor encoded by said polynucleotide or a host cell genetically engineered with said polynucleotide or with a vector containing said polynucleotide to express said bitter taste receptor with a potential agonist that is structurally related to absinthin, artemorin, arglabin, azathioprine, azepinon, benzoin, brucine, camphor, chlorhexidine, N,N'-diethylthiourea, herbolid A, isohumulone, noscapine, parthenolid, or arborescin for hTAS2R14; that is structurally related to absinthin, artemorin, amarogentin, arglabin, azathioprine, benzoin, camphor, cascarillin, papaverin, parthenolid, picrotoxinin, arborescin or (-)-a-thujon for hTAS2R10; or that is structurally related to artemorin, amarogentin, azathioprine or campor for hTAS2R4; and
(2) determining whether the potential agonist induces bitter taste receptor activity.

The polynucleotide employed in both aspects of the present invention encodes a polypeptide that still exhibits essentially the same activity as the mature hTAS2R14, hTAS2R10 or hTAS2R4 bitter taste receptor, respectively, i.e. has "bitter taste receptor activity". Preferably the polypeptide has at least 20% (e.g., at least: 20%; 30%; 40%; 50%; 60%; 70%; 80%; 90%; 95%; 98%; 99%; 99.5%; or 100% or even more) of the activity of the full-length mature hTAS2R14, hTAS2R10 and hTAS2R4, respectively. One preferred way of measuring hTAS2R14, hTAS2R10 and hTAS2R4 activity, respectively, is the ability to release intracellular calcium in a heterologous cell expression system like, for example, (HEK293T/G16gust44) cells that stably expresses a chimeric G-protein consisting of Gα16 and 44 carboxylterminai amino acids of α-gustducin, in response to bitter tastants, which is dependent on the expression of polypeptides encoded by the polynucleotides of the present invention. The amount of intracellular calcium released can be monitored by, for example, the in vitro FLIPR assay described herein but also by the measurement of one of a variety of other parameters including, for example, $IP_3$ or cAMP. Additional ways of measuring G-protein coupled receptor activity are known in the art and comprise without limitation electrophysiological methods, transcription assays, which measure, e.g. activation or repression of reporter genes which are coupled to regulatory sequences regulated via the respective G-protein coupled signalling pathway, such reporter proteins comprise, e.g., CAT or LUC; assays measuring internalization of the receptor; or assays in frog melanophore systems, in which pigment movement in melanophores is used as a readout for the activity of adenylate cyclase or phospholipase C (PLC), which in turn are coupled via G-proteins to exogenously expressed receptors (see, for example, McClintock T. S. et al. (1993) Anal. Biochem. 209: 298-305; McClintock T. S. and Lerner M. R. (1997) Brain Res. Brain, Res. Protoc. 2: 59-68, Potenza M N (1992) Pigment Cell Res. 5: 372-328, and Potenza M. N. (1992) Anal. Biochem. 206: 315-322).

The term "potential antagonist", comprises any perceivable chemical substance or combination thereof in a non-purified, partially purified or purified state. The potential antagonist is selected on the basis of its antagonizing behaviour. An "identified antagonist" of hTAS2R14, hTAS2R10 and hTAS2R4 bitter taste receptor activity, respectively, is a substance which reduces the activity of hTAS2R14, hTAS2R10 or hTAS2R4 stimulated by absinthin, artemorin, arglabin, azathioprine, azepinon, benzoin, brucine, camphor, chlorhexidine, N,N'-diethylthiourea, herbolid A, isohumulone, noscapine, parthenolid, or arborescin or structurally related agonists thereof for hTAS2R14; absinthin, artemorin, amarogentin, arglabin, azathioprine, benzoin, camphor, cascarillin, papaverin, parthenolid, picrotoxinin, arborescin or (−)-a-thujon or structurally related agonists thereof for hTAS2R10; or artemorin, amarogentin, azathioprine or campor or structurally related agonists thereof for hTAS2R4 at least by 10% (e.g., at least: 10%, 15%; 20%; 30%; 40%; 50%; 60%; 70%; 80%; 90%; 95%; 98%; 99%; 99.5%; or 100%) at the same molar concentration. The extend of the lowering of the hTAS2R14, hTAS2R10 or hTAS2R4 bitter taste receptor activity, caused by the antagonist is determined in the presence of the respective agonist, e.g. absinthin, artemorin, arglabin, azathioprine, azepinon, benzoin, brucine, camphor, chlorhexidine, N,N'-diethylthiourea, herbolid A, isohumulone, noscapine, parthenolid, or arborescin or structurally related agonists thereof for hTAS2R14; absinthin, artemorin, amarogentin, arglabin, azathioprine, benzoin, camphor, cascarillin, papaverin, parthenolid, picrotoxinin, arborescin or (−)-a-thujon or structurally related agonists thereof for hTAS2R10; or artemorin, amarogentin, azathioprine or campor or structurally related agonists thereof for hTAS2R4, which may be added prior, concomitantly or after addition of the antagonist. Preferably, the identified antagonist exerts this activity, if present in the same molar concentration as absinthin, artemorin, amarogentin, arglabin, azathioprine, azepinon, benzoin, brucine, camphor, cascarillin, chlorhexidine, N,N'-diethylthiourea, herbolid A, isohumulone, noscapine, papaverin, parthenolid, picrotoxinin, arborescin or (−)-a-thujon or an agonist structurally related to artemorin. In a preferred embodiment, the "potential antagonist" is a compound structurally related to absinthin, artemorin, amarogentin, arglabin, azathioprine, azepinon, benzoin, brucine, camphor, cascarillin, chlorhexidine, N,N'-diethylthiourea, herbolid A, isohumulone, noscapine, papaverin, parthenolid, picrotoxinin, arborescin or (−)-a-thujon.

Preferably, the antagonist exerts its antagonizing action when it is contacted prior, concomitantly or after, preferably concomitantly, to contacting the hTAS2R14, hTAS2R10 and hTAS2R4 polypeptide, respectively, or the host cell genetically engineered with a polynucleotide encoding hTAS2R14, hTAS2R10 and hTAS2R4 polypeptide as defined above or with a vector containing a polynucleotide as defined above to express hTAS2R14, hTAS2R10 and hTAS2R4 polypeptide, respectively, with absinthin, artemorin, amarogentin, arglabin, azathioprine, azepinon, benzoin, brucine, camphor, cascarillin, chlorhexidine, N,N'-diethylthiourea, herbolid A, isohumulone, noscapine, papaverin, parthenolid, picrotoxinin, arborescin or (−)-a-thujon or an agonist structurally related to absinthin, artemorin, amarogentin, arglabin, azathioprine, azepinon, benzoin, brucine, camphor, cascarillin, chlorhexidine, N,N'-diethylthiourea, herbolid A, isohumulone, noscapine, papaverin, parthenolid, picrotoxinin, arborescin or (−)-a-thujon. Preferably, if contacted at the same molar concentration as absinthin, artemorin, amarogentin, arglabin, azathioprine, azepinon, benzoin, brucine, camphor, cascarillin, chlorhexidine, N,N'-diethylthiourea, herbolid A, isohumulone, noscapine, papaverin, parthenolid, picrotoxinin, arborescin or (−)-a-thujon or the structurally related agonist.

The term "potential agonist", comprises substances structurally related to absinthin, artemorin, amarogentin, arglabin, azathioprine, azepinon, benzoin, brucine, camphor, cascarillin, chlorhexidine, N,N'-diethylthiourea, herbolid A, isohumulone, noscapine, papaverin, parthenolid, picrotoxinin, arborescin or (−)-a-thujon in a non-purified, partially purified or purified state. The potential agonist is selected on the basis of its hTAS2R14, hTAS2R10 and hTAS2R4 bitter taste receptor activity stimulating behaviour. An "identified agonist" stimulates hTAS2R14, hTAS2R10 and hTAS2R4 bitter taste receptor activity, respectively, to at least 10% (e.g., at least: 10%, 30%, 50%, 80%, 100%, 200%, 300%, 500%, 1,000%, 10,000%) of the activity elicited by absinthin, artemorin, amarogentin, arglabin, azathioprine, azepinon, benzoin, brucine, camphor, cascarillin, chlorhexidine, N,N'-diethylthiourea, herbolid A, isohumulone, noscapine, papaverin, parthenolid, picrotoxinin, arborescin and (−)—a-thujon, respectively. Preferably, the identified agonist exerts this activity, if present at the same molar concentration as absinthin, artemorin, amarogentin, arglabin, azathioprine, azepinon, benzoin, brucine, camphor, cascarillin, chlorhexidine, N,N'-diethylthiourea, herbolid A, isohumulone, noscapine, papaverin, parthenolid, picrotoxinin, arborescin or (−)-a-thujon.

The hTAS2R14, hTAS2R10 and hTAS2R4 polynucleotide molecules, respectively, usable in the method of the present invention can be DNA, cDNA, genomic DNA, synthetic DNA, or RNA, and can be double-stranded or single-stranded, the sense and/or an antisense strand. Segments of these molecules are also considered within the scope of the invention, and can be produced by, for example, the polymerase chain reaction (PCR) or generated by treatment with one or more restriction endonucleases. A ribonucleic acid (RNA) molecule can be produced by in vitro transcription.

The polynucleotide molecules useable in the method of the present invention can contain naturally occurring sequences, or sequences that differ from those that occur naturally, but, due to the degeneracy of the genetic code, encode the same polypeptide (for example, the polypeptide with SEQ ID NO: 2, 4, or 6). In addition, these nucleic acid molecules are not limited to coding sequences, e.g., they can include some or all of the non-coding sequences that lie upstream or downstream from a coding sequence.

The polynucleotide molecules of the invention can be synthesized in vitro (for example, by phosphoramidite-based synthesis) or obtained from a cell, such as the cell of a bacteria or a mammal. The nucleic acids can be those of a human but also include orthologous polynucleotides derived from a non-human primate, mouse, rat, guinea pig, cow, sheep, horse, pig, rabbit, dog, or cat as long as they fulfil the criteria set out above. Combinations or modifications of the polynucleotides within these types of nucleic acids are also encompassed. Means to identify orthologous polynucleotide molecules of the invention are available to a person of skill and comprise the use of BLAST searches (see below) and database mining of databases such as the EMBL, NCBI and other databases comprising polynucleotides and amino acid sequences.

In addition, the polynucleotides useable in the method of the present invention can encompass segments that are not found as such in the natural state. Thus, the invention encompasses recombinant nucleic acid molecules incorporated into a vector (for example, a plasmid or viral vector) or into the genome of a heterologous cell (or the genome of a homologous cell, at a position other than the natural chromosomal location). Recombinant nucleic acid molecules and uses therefore are discussed further below.

In certain preferred embodiments the method of the present invention uses isolated nucleic acid molecules which are at least 50% (or 55%, 60%, 65%, 70%, 75%, 80%, 85%, 90%, 95%, or 98%) identical to: (a) a nucleic acid molecule that encodes the polypeptide of SEQ ID NO: 2, 4, or 6; (b) the polynucleotide sequence of SEQ ID NO: 1, 3, or 5 and (c) a nucleic acid molecule which includes a segment of at least 30 (e.g., at least 30, 40, 50, 60, 80, 100, 125, 150, 175, 200, 250, 300, 400, 500, 600, 700, 800, 850, and 900) contiguous polynucleotides of SEQ ID NO: 1, 3 and 5, respectively, in as long as these nucleic acid molecules encode a polypeptide having hTAS2R14, hTAS2R10 and hTAS2R4 bitter taste receptor activity, respectively The determination of percent identity between two sequences is accomplished using the mathematical algorithm of Karlin and Altschul (1993) Proc. Natl. Acad. ScI USA 90: 5873-5877. Such an algorithm is incorporated into the BLASTN and BLASTP programs of Altschul et al. (1990) J. MoI. Biol. 215: 403-410. BLAST polynucleotide searches are performed with the BLASTN program, score=100, word length=12, to obtain polynucleotide sequences homologous to hTAS2R14, hTAS2R10 or hTAS2R4 encoding nucleic acids. BLAST protein searches are performed with the BLASTP program, score=50, wordlength=3, to obtain amino acid sequences homologous to the hTAS2R14, hTAS2R10 and hTAS2R4 polypeptide, respectively. To obtain gapped alignments for comparative purposes, Gapped BLAST is utilized as described in Altschul et al. (1997) Nucleic Acids Res. 25: 3389-3402. When utilizing BLAST and Gapped BLAST programs, the default parameters of the respective programs are used.

Hybridization can also be used as a measure of homology between two nucleic acid sequences. A nucleic acid sequence encoding hTAS2R14, hTAS2R10 or hTAS2R4, or a portion thereof, can be used as a hybridization probe according to standard hybridization techniques. The hybridization of a hTAS2R14, hTAS2R10 or hTAS2R4 probe to DNA or RNA from a test source (e.g., a mammalian cell) is an indication of the presence of the hTAS2R14, hTAS2R10 or hTAS2R4 DNA or RNA in the test source. Hybridization conditions are known to those skilled in the art and can be found, for example, in Current Protocols in Molecular Biology, John Wiley & Sons, N.Y., 6.3.1-6.3.6, 1991. Moderate hybridization conditions are defined as equivalent to hybridization in 2× sodium chloride/sodium citrate (SSC) at 30° C., followed by a wash in 1×SSC, 0.1% SDS at 50° C. Highly stringent conditions are defined as equivalent to hybridization in 6× sodium chloride/sodium citrate (SSC) at 45° C., followed by a wash in 0.2×SSC, 0.1% SDS at 65° C.

The polynucleotides or proteins useable in the method of the present invention can be comprised in a vector containing the polynucleotide(s) or a protein encoded by above-mentioned polynucleotide. The term "vector" refers to a protein or a polynucleotide or a mixture thereof which is capable of being introduced or of introducing the proteins and/or nucleic acid comprised therein into a cell. It is preferred that the proteins encoded by the introduced polynucleotide are expressed within the cell upon introduction of the vector.

In a preferred embodiment a vector useable in the method of the present invention comprises plasmids, phagemids, phages, cosmids, artificial mammalian chromosomes, knock-out or knock-in constructs, viruses, in particular adenoviruses, vaccinia viruses, attenuated vaccinia viruses, canary pox viruses, lentivirus (Chang, U. and Gay, E. E. (2001) Curr. Gene Therap. 1: 237-251), herpes viruses, in particular Herpes simplex virus (HSV-I, Carlezon, W. A. et al. (2000) Crit. Rev. Neurobiol. 14: 47-67), baculovirus, retrovirus, adeno-associated-virus (AAV, Carter, P J. and Samulski, R J. (2000) J. MoI. Med. 6:17-27), rhinovirus, human immune deficiency virus (HIV), filovirus and engineered versions thereof (see, for example, Cobinger G. P. et al. (2001) Nat. Biotechnol. 19:225-30), virosomes, "naked" DNA liposomes, and nucleic acid coated particles, in particular gold spheres. Particularly preferred are viral vectors like adenoviral vectors or retroviral vectors (Lindemann et al. (1997) MoI. Med. 3: 466-76 and Springer et al. (1998) MoI. Cell. 2: 549-58). Liposomes are usually small unilamellar or multilamellar vesicles made of cationic, neutral and/or anionic lipids, for example, by ultrasound treatment of liposomal suspensions. The DNA can, for example, be ionically bound to the surface of the liposomes or internally enclosed in the liposome. Suitable lipid mixtures are known in the art and comprise, for example, DOTMA (1, 2-Dioleyloxypropyl-3-trimethylammoniumbromid) and DOPE (Dioleoyl-phosphatidylethanolamin) which both have been used on a variety of cell lines.

Nucleic acid coated particles are another means for the introduction of nucleic acids into cells using so called "gene guns", which allow the mechanical introduction of particles into cells. Preferably the particles itself are inert, and therefore, are in a preferred embodiment made out of gold spheres.

In a further aspect polynucleotides useable in the method of the present invention are operatively linked to expression control sequences allowing expression in prokaryotic and/or eukaryotic host cells. The transcriptional/translational regulatory elements referred to above include but are not limited to inducible and non-inducible, constitutive, cell cycle regulated, metabolically regulated promoters, enhancers, operators, silencers, repressors and other elements that are known to those skilled in the art and that drive or otherwise regulate gene expression. Such regulatory elements include but are not limited to regulatory elements directing constitutive expression like, for example, promoters transcribed by RNA polymerase III like, e.g. promoters for the snRNA U6 or scRNA 7SK gene, the cytomegalovirus hCMV immediate early gene, the early or late promoters of SV40 adenovirus, viral promoter and activator sequences derived from, e.g. NBV, HCV, HSV, HPV, EBV, HTLV, MMTV or HIV; which allow inducible expression like, for example, CUP-I promoter, the tet-repressor as employed, for example, in the tet-on or tet-off systems, the lac system, the trp, system; regulatory elements directing tissue specific expression, preferably taste bud specific expression, e.g. PLCB2 promoter or gustducin promoter, regulatory elements directing cell cycle specific expression like, for example, cdc2, cdc25C or cyclin A; or the TAC system, the TRC system, the major operator and promoter regions of phage A, the control regions of fd coat protein, the promoter for 3-phosphoglycerate kinase, the promoters of acid phosphatase, and the promoters of the yeast α- or a-mating factors.

As used herein, "genetically engineered" means that the host cell is transgenic for the polynucleotide or vector containing the polynucleotide.

A polypeptide encoding a "mature form" of a protein or polypeptide means that said protein or polypeptide contains all polypeptide elements that allow it to undergo some or all potential post- or cotranslational processes such as proteolytic processing, phosphorylation, lipidation and the like comprised in the state of the art such that said polypeptide or protein can correctly fold and carry out part or all of its wildtype function once it reaches its "mature form".

As used herein, "operatively linked" means incorporated into a genetic construct so that expression control sequences effectively control expression of a coding sequence of interest.

Similarly, the polynucleotides useable in the method of the present invention can form part of a hybrid gene encoding additional polypeptide sequences, for example, a sequence that functions as a marker or reporter. Examples of marker and reporter genes include β-lactamase, chloramphenicol acetyltransferase (CAT), adenosine deaminase (ADA), aminoglycoside phosphotransferase (neo$^r$, G418$^r$), dihydrofolate reductase (DHFR), hygromycin-B-phosphotransferase (HPH), thymidine kinase (TK), lacZ (encoding β-galactosidase), and xanthine guanine phosphoribosyl-transferase (XGPRT). As with many of the standard procedures associated with the practice of the method of the invention, skilled artisans will be aware of additional useful reagents, for example, additional sequences that can serve the function of a marker or reporter.

The method of the present invention may also use hybrid polypeptides or polynucleotides encoding them. In general a hybrid polypeptide will include a first portion and a second portion; the first portion being one or more hTAS2R14, hTAS2R10 or hTAS2R4 polypeptide and the second portion being, for example, the reporter(s) described above or an Ig constant region or part of an Ig constant region, e.g., the CH2 and CH3 domains of IgG2a heavy chain. Other hybrids could include an antigenic tag or His tag to facilitate purification and/or detection. Recombinant nucleic acid molecules can also contain a polynucleotide sequence encoding the hTAS2R14, hTAS2R10 or hTAS2R4 polypeptide operatively linked to a heterologous signal sequence. Such signal sequences can direct the protein to different compartments within the cell and are well known to someone of skill in the art. A preferred signal sequence is a sequence that facilitates secretion of the resulting protein.

Another aspect of the present invention is the use of a host cell genetically engineered with a polynucleotide or a vector as outlined above. The host cells that may be used in the method of the present invention include but are not limited to prokaryotic cells such as bacteria (for example, *E. coli* and *B. subtilis*), which can be transformed with, for example, recombinant bacteriophage DNA, plasmid DNA, or cosmid DNA expression vectors containing the polynucleotide molecules of the invention; simple eukaryotic cells like yeast (for example, *Saccharomyces* and *Pichia*), which can be transformed with, for example, recombinant yeast expression vectors containing the polynucleotide molecule of the invention; insect cell systems like, for example, Sf9 or Hi5 cells, which can be infected with, for example, recombinant virus expression vectors (for example, baculovirus) containing the polynucleotide molecules; amphibian cells, e.g. *Xenopus* oocytes, which can be injected with, for example, plasmids; plant cell systems, which can be infected with, for example, recombinant virus expression vectors (for example, cauliflower mosaic virus (CaMV) or tobacco mosaic virus (TMV)) or transformed with recombinant plasmid expression vectors (for example, Ti plasmid) containing a hTAS2R14, hTAS2R10 or hTAS2R4 polynucleotide sequence; or mammalian cell systems (for example, COS, CHO, BHK, HEK293, VERO, HeLa, MDCK, Wi38, and NIH 3T3 cells), which can be transformed with recombinant expression constructs containing, for example, promoters derived, for example, from the genome of mammalian cells (for example, the metallothionein promoter) from mammalian viruses (for example, the adenovirus late promoter and the vaccinia virus 7.5K promoter) or from bacterial cells (for example, the tet-repressor binding is employed in the tet-on and tet-off systems). Also useful as host cells are primary or secondary cells obtained directly from a mammal and transfected with a plasmid vector or infected with a viral vector. Depending on the host cell and the respective vector used to introduce the polynucleotide of the invention the polynucleotide can integrate, for example, into the chromosome or the mitochondrial DNA or can be maintained extrachromosomally like, for example, episomally or can be only transiently comprised in the cells.

In a preferred embodiment, the hTAS2R14, hTAS2R10 or hTAS2R4 expressed by such cells are functional and have bitter taste receptor activity, i.e., upon binding to one or more bitter molecules they trigger an activation pathway in the cell. The cells are preferably mammalian (e.g., human, non-human primate, horse, bovine, sheep, pig, dog, cat, goat, rabbit, mouse, rat, guinea pig, hamster, or gerbil) cells, insect cells, bacterial cells, or fungal (including yeast) cells. The polypeptides useable in the method of the invention include all those disclosed herein and functional fragments of these polypeptides. The terms "polypeptide" and "protein" are used interchangeably and mean any peptide-linked chain of amino acids, regardless of length or post-translational modification. As used herein, a functional fragment of the hTAS2R14, hTAS2R10 or hTAS2R4 is a fragment of the hTAS2R14, hTAS2R10 or hTAS2R4 that is shorter than the full-length hTAS2R14, hTAS2R10 or hTAS2R4 but that has at least 20% (e.g., at least: 20%, 30%, 40%, 50%, 60%, 70%, 80%, 90%, 95%, 98%, 99%, 99.5%, 100%, 150%, 200%, 500%, 1000%, 10000% or even more) of the ability of the full-length hTAS2R14, hTAS2R10 or hTAS2R4 to be stimulated by one of the bitter substances identified herein. Binding assays and bitter substances are described in more detail herein below. The polypeptides can also include fusion proteins that contain either a full-length hTAS2R14, hTAS2R10 or hTAS2R4 polypeptide or a functional fragment of it fused to an unrelated amino acid sequence. The unrelated sequences can add further functional domains or signal peptides.

The polypeptides can be any of those described above but with not more than 50 (e.g., not more than: 50, 45, 40, 35, 30, 25, 20, 15, 14, 13, 12, 11, 10, nine, eight, seven, six, five, four, three, two, or one) conservative substitutions. Conservative substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine. All that is required of a polypeptide having one or more conservative substitutions is that it has at least 20% (e.g., at least: 20%; 30%; 40%; 50%; 60%; 70%; 80%; 90%; 95%; 98%; 99%; 99.5%; 100%, 150%, 200%, 500%, 1000%, 10000% or even more) of the ability of the full-length hTAS2R14, hTAS2R10 or hTAS2R4 to be stimulated by the respective agonist.

Polypeptides and fragments of the polypeptides useable in the method of the present invention can be modified, for example, for in vivo use by the addition of blocking agents, at the amino- and/or carboxyl-terminal ends, to facilitate survival of the relevant polypeptide in vivo. This can be useful in those situations in which the peptide termini tend to be degraded by proteases prior to cellular uptake. Such blocking agents can include, without limitation, additional related or unrelated peptide sequences that can be attached to the amino and/or carboxyl terminal residues of the peptide to be administered. This can be done either chemically during the synthesis of the peptide or by recombinant DNA technology by methods familiar to artisans of average skill. The antagonists or agonists of the bitter taste receptors identified herein are of great importance for specific stimulation of a given bitter taste receptor and identification of substances that antagonize it, respectively.

The term "contacting" in the context of the present invention means any interaction between the antagonist and/or agonist with the polypeptide or the host cell, whereby any of the at least two components can be independently of each other in a liquid phase, for example in solution, or in suspension or can be bound to a solid phase, for example, in the form of an essentially planar surface or in the form of particles, beads or the like, in a preferred embodiment a multitude of different compounds are immobilized on a solid surface like, for example, on a compound library chip and the protein of the present invention is subsequently contacted with such a chip, in another preferred embodiment the host cells are genetically engineered with a polynucleotide encoding hTAS2R14, hTAS2R10 or hTAS2R4 or with a vector containing such a polynucleotide, express the hTAS2R$^{14}$, hTAS2R$^{10}$ or hTAS2R$^{4}$ bitter taste receptor at the cell surface and are contacted separately in small containers, e.g., microtitre plates, with various compounds.

As used herein, the term "isolating" an agonist or antagonist refers to the process of selecting, identifying, isolating or evolving an agonist or antagonist out of a group of at least two different potential agonists or potential antagonists whereby the said selected, identified, isolated or evolved agonist or antagonist exhibits preferred features compared with the other agonist or antagonists such as, for example, stronger modulation, e.g. activation or inhibition, of receptor activation and/or longer or shorter lasting modulation, e.g. activation or inhibition, of receptor activation.

As a further step after measuring the antagonizing effect of a potential antagonist and after having measured the decrease of bitter taste for at least two different potential antagonists at least one potential antagonist can be selected, for example, on grounds of the detected decrease of intracellular release of calcium, if compared to contacting with the known agonist alone.

In a preferred embodiment of either method of the present invention the potential agonist or potential antagonist that is employed in the identification process is structurally related to absinthin, arglabin, arborescin, artemorin, noscapine, or parthenolide and has a structure according to formula (I)

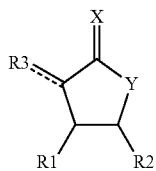

(I)

wherein

R$^1$ and R$^2$ together form a cycloalkyl, preferably C$_3$-C$_{14}$-cycloalkyl, e.g. C$_3$, C$_4$, C$_5$, C$_6$, C$_7$, C$_8$, C$_9$, C$_{10}$, C$_{11}$, C$_{12}$, C$_{13}$ or C$_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, bicyclo[5.3.0]decyl, octahydro-pentalenyl, octahydro-indenyl, decahydro-azulenyl, adamantly, or decahydro-naphthalenyl; heterocycloalkyl, preferably C$_3$-C$_{14}$-heterocycloalkyl, e.g. C$_3$, C$_4$, C$_5$, C$_6$, C$_7$, C$_8$, C$_9$, C$_{10}$, C$_{11}$, C$_{12}$, C$_{13}$ or C$_{1-4}$-heterocycloalkyl, in particular piperidinyl, morpholinyl, 1,3-diazacyclohexane, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7, 11-dioxo-spiro[5,5]undecyl, 1,4-diazabicyclo[2.2.2]oct-2-yl, tetrahydrofuran-2-yl, tetrahydrofuran-3-yl, tetrahydrothien-2-yl, tetrahydrothien-3-yl, piperazinyl, decahydroquinolinyl, decahydro-isoquinolinyl, decahydro-quinoxalinyl, or decahydro-quinazolinyl; an alicyclic system, preferably C$_3$-C$_{14}$-alicyclic system, e.g. C$_3$, C$_4$, C$_5$, C$_6$, C$_7$, C$_8$, C$_9$, C$_{10}$, C$_{11}$, C$_{12}$, C$_{13}$ or C$_{14}$-alicyclic system, in particular cyclopropenyl, cyclobutenyl, cyclopentenyl, cyclohexenyl, cycloheptenyl, cyclooctyl, cyclononenyl, cyclodecenyl, spiro[3,3]heptenyl, spiro[3,4]octenyl, spiro[4,3]octenyl, spiro[3,5]nonenyl, spiro[5,3]nonenyl, spiro[3,6]decenyl, spiro[6,3]decenyl, spiro[4,5]decenyl, spiro[5,4]decenyl, bicyclo[4.1.0]heptenyl, bicyclo[3.2.0]heptenyl, bicyclo[2.2.1]heptenyl, bicyclo[2.2.2]octenyl, bicyclo[5.1.0]octenyl, bicyclo[4.2.0]octenyl, bicyclo[5.3.0]decenyl, hexahydro-pentalenyl, hexahydro-indenyl, octahydro-azulenyl, or octahydro-naphthalenyl, or a derivative thereof, wherein 1, 2 or 3 carbon atoms are replaced by a heteroatom each independently selected from the group consisting of nitrogen, sulphur, or oxygen; aryl, in particular phenyl, naphthalenyl or anthracenyl; or heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; preferably decahydro-naphthalenyl, cyclodecyl, octahydro-naphthalenyl, or cyclodecenyl; optionally substituted;

R$^3$ is H, OH, alkyl, in particular C$_1$-C$_6$ alkyl, e.g. C$_1$, C$_2$, C$_3$, C$_4$, C$_5$, or C$_6$ alkyl, preferably methyl, ethyl, propyl, iso-propyl, butyl, iso-butyl, tert-butyl, pentyl, hexyl; alkenyl, in particular C$_1$-C$_6$ alkenyl, e.g. C$_1$, C$_2$, C$_3$, C$_4$, C$_5$, or C$_6$ alkenyl, preferably methenyl, ethenyl, 1-propenyl, 2-propenyl, 1-iso-propenyl, 2-iso-propenyl, 1-butenyl, 2-butenyl, 3-butenyl; alkoxy, in particular C$_1$-C$_6$ alkoxy, e.g. C$_1$, C$_2$, C$_3$, C$_4$, C$_5$, or C$_6$ alkoxy, preferably methoxy, ethoxy, propoxy, iso-propoxy, butoxy, iso-butoxy, tert-butoxy, pentoxy, or hexoxy; alkoxyalkyl, in particular C$_1$-C$_6$ alkoxy-C$_1$-C$_6$ alkyl, e.g. methoxymethyl, ethoxymethyl, propoxymethyl, methoxyethyl, ethoxyethyl, propoxyethyl, methoxypropyl, ethoxypropyl, or propoxypropyl; preferably C$_1$-C$_6$ alkyl, more preferably methyl; cycloalkyl, in particular C$_3$-C$_{14}$-cycloalkyl, e.g. C$_3$, C$_4$, C$_5$, C$_6$, C$_7$, C$_8$, C$_9$, C$_{10}$, C$_{11}$, C$_{12}$, C$_{13}$ or C$_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, bicyclo

[5.3.0]decyl, octahydro-pentalenyl, octahydro-indenyl, decahydro-azulenyl, adamantly, or decahydro-naphthalenyl; heterocycloalkyl, preferably $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuran-3-yl, tetrahydrothien-2-yl, tetrahydrothien-3-yl, piperazinyl, decahydroquinolinyl, decahydro-isoquinolinyl, decahydro-quinoxalinyl, or decahydroquinazolinyl; an alicyclic system, preferably $C_3$-$C_{14}$-alicyclic system, e.g. $C_3$, $C_4$, $C_5$, $C_6$, $C_7$, $C_8$, $C_9$, $C_{10}$, $C_{11}$, $C_{12}$, $C_{13}$ or $C_{14}$-alicyclic system, in particular cyclopropenyl, cyclobutenyl, cyclopentenyl, cyclohexenyl, cycloheptenyl, cyclooctenyl, cyclononenyl, cyclodecenyl, spiro[3,3]heptenyl, spiro[3,4]octenyl, spiro[4,3]octenyl, spiro[3,5]nonenyl, spiro[5,3]nonenyl, spiro[3,6]decenyl, spiro[6,3]decenyl, spiro[4,5]decenyl, spiro[5,4]decenyl, bicyclo[4.1.0]heptenyl, bicyclo[3.2.0]heptenyl, bicyclo[2.2.1]heptenyl, bicyclo[2.2.2]octenyl, bicyclo[5.1.0]octenyl, bicyclo[4.2.0]octenyl, bicyclo[5.3.0]decenyl, hexahydro-pentalenyl, hexahydro-indenyl, octahydro-azulenyl, or octahydro-naphthalenyl, or a derivative thereof, wherein 1, 2 or 3 carbon atoms are replaced by a heteroatom each independently selected from the group consisting of nitrogen, sulphur, or oxygen; aryl, in particular phenyl, naphthalenyl or anthracenyl; or heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; preferably decahydro-naphthalenyl, cyclodecyl, octahydro-naphthalenyl, or cyclodecenyl; optionally substituted;

X is O or S; preferably O;

Y is O or NH or S; preferably O; and the dashed bond may present or not, preferably the dashed bond is present.

In a preferred embodiment of the method of the present invention the ring system formed by $R^1$ and $R^2$ is (i) cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, bicyclo[5.3.0]decyl, octahydro-pentalenyl, octahydro-indenyl, decahydro-azulenyl, adamantly, or decahydro-naphthalenyl; optionally substituted 1 to 14 times, i.e. 1, 2, 3, 4, 5, 6, 7, 8, 9, 10, 11, 12, 13, or 14 times, depending on the number of available valences with a substituent which is in each instance independently selected from the group consisting of halogen, in particular F, Cl, Br or I; —$NO_2$; —CN; —$OR^6$; —$NR^6R^7$; —$COOR^6$; —$CONR^6R^7$; —$NR^8COR^9$; —$NR^8COR^9$; —$NR^8CONR^6R^7$; —$NR^9SO_2A$; —$COR^6$; —$SO_2NR^6R^7$; —$OOCR^8$; —$CR^8R^9OH$; $R^8OH$; and -A; or two substituents on adjacent carbon atoms form together with an oxygen atom an epoxy group or a cycloalkyl, cycloheteroalkyl, alicyclic system, aryl or heteroaryl;

$R^6$ and $R^7$ is each independently selected from the group consisting of hydrogen, alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_2$-$C_6$ alkenyl, e.g. $C_2$, $C_3$, $C_4$, $C_5$, or $C_6$ alkenyl, preferably ethenyl, 1-propenyl, 2-propenyl, 1-iso-propenyl, 2-iso-propenyl, 1-butenyl, 2-butenyl, 3-butenyl; alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantly, decahydro-naphthalenyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,1'-dioxo-spiro[5,5]undecyl, 1,4-diazabicyclo[2.2.2]oct-2-yl, tetrahydrofuran-2-yl, tetrahydrofuranyl, tetrahydrothienyl, tetrahydrothienyl, piperazinyl, decahydroquinolinyl, decahydro-isoquinolinyl, decahydro-quinoxalinyl, decahydro-quinazolinyl; aryl, in particular phenyl, naphthalenyl or anthracenyl; heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; and aralkyl, preferably $C_1$-$C_6$ aralkyl, e.g. $C_1$, $C_2$, $C_3$, $C_4$, $C_5$, or $C_6$ aralkyl; or together form a heteroaryl, in particular, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, indolyl, isoindolyl, 1H-indazolyl, benzimidazolyl, indoxazinyl, 2,1-benzisoxazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; optionally substituted;

$R^8$ and $R^9$ is each independently selected from the group consisting of hydrogen; alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_2$-$C_6$ alkenyl, e.g. $C_2$, $C_3$, $C_4$, $C_5$, or $C_6$ alkenyl, preferably ethenyl, 1-propenyl, 2-propenyl, 1-iso-propenyl, 2-iso-propenyl, 1-butenyl, 2-butenyl, 3-butenyl; alkynyl, in particular $C_2$-$C_6$ alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantly, decahydro-naphthalenyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuranyl, tetrahydrothienyl, tetrahydrothienyl, piperazinyl, decahydro-quinolinyl, decahydro-isoquinolinyl, decahydro-quinoxalinyl, decahydro-quinazolinyl; alkoxy, in particular $C_1$-$C_6$ alkoxy, e.g. $C_1$, $C_2$, $C_3$, $C_4$, $C_5$, or $C_6$ alkoxy, preferably methoxy, ethoxy, propoxy, iso-propoxy, butoxy, iso-butoxy, tert-butoxy, pentoxy, or hexoxy; aryl, in particular phenyl, naphthalenyl or anthracenyl; aralkyl; preferably $C_1$-$C_6$ aralkyl, e.g. $C_1$, $C_2$, $C_3$, $C_4$, $C_5$, or $C_6$ aralkyl; heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; and —NR$^6$R$^7$;

A is selected from the group consisting of alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_1$-$C_6$ alkenyl, e.g. $C_1$, $C_2$, $C_3$, $C_4$, $C_5$, or $C_6$ alkenyl, preferably methenyl, ethenyl, 1-propenyl, 2-propenyl, 1-iso-propenyl, 2-iso-propenyl, 1-butenyl, 2-butenyl, 3-butenyl; alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantly, decahydro-naphthalenyl; alkoxy, in particular $C_1$-$C_6$ alkoxy, e.g. $C_1$, $C_2$, $C_3$, $C_4$, $C_5$, or $C_6$ alkoxy, preferably methoxy, ethoxy, propoxy, iso-propoxy, butoxy, iso-butoxy, tert-butoxy, pentoxy, or hexoxy; alkoxyalkyl, in particular $C_1$-$C_6$-alkoxy-$C_1$-$C_6$-alkyl, e.g. methoxymethyl, ethoxymethyl, propoxymethyl, methoxyethyl, ethoxyethyl, propoxyethyl, methoxypropyl, ethoxypropyl, or propoxypropyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuranyl, tetrahydrothienyl, tetrahydrothienyl, piperazinyl, decahydroquinolinyl, decahydro-isoquinolinyl, decahydro-quinoxalinyl, decahydro-quinazolinyl; an alicyclic system, which may comprise one or more heteroatoms, e.g. 1, 2, 3, or 4, preferably selected from the group consisting of O, S, or N; in particular 1,2-dihydropyridinyl, 1,2,5,6-tetrahydropyridinyl, 1,2,3,4-tetrahydropyridyl, 1,2-dihydropyrazyl, 1,2,3,4-tetrahydropyrazyl, cyclopropenyl, cyclobutenyl, cyclopentenyl, cyclohexenyl, cycloheptenyl; aryl, in particular phenyl, naphthalenyl or anthracenyl; and heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2, 4-benzotriazinyl; optionally substituted;

(ii) piperidinyl, morpholinyl, 1,3-diazacyclohexane, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuranyl, tetrahydrothienyl, tetrahydrothienyl, piperazinyl, decahydroquinolinyl, decahydro-isoquinolinyl, decahydroquinoxalinyl, or decahydro-quinazolinyl;

optionally substituted 1 to 14 times, i.e. 1, 2, 3, 4, 5, 6, 7, 8, 9, 10, 11, 12, 13, or 14 times, depending on the number of available valences with a substituent which is in each instance independently selected from the group consisting of halogen, in particular F, Cl, Br or I; —NO$_2$; —CN; —OR$^6$; —NR$^6$R$^7$; —COOR$^6$; —CONR$^6$R$^7$; —NR$^8$COR$^9$; —NR$^8$COR$^9$; —NR$^8$CONR$^6$R$^7$; —NR$^9$SO$_2$A; —COR$^6$; —SO$_2$NR$^6$R$^7$; —OOCR$^8$; —CR$^8$R$^9$OH; R$^8$OH; and -A or two substituents on adjacent carbon or heteroatoms atoms—as the case may be—form together a cycloalkyl, cycloheteroalkyl, alicyclic system, aryl or heteroaryl;

$R^6$ and $R^7$ is each independently selected from the group consisting of hydrogen, alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_2$-$C_6$ alkenyl, e.g. $C_2$, $C_3$, $C_4$, $C_5$, or $C_6$ alkenyl, preferably ethenyl, 1-propenyl, 2-propenyl, 1-iso-propenyl, 2-iso-propenyl, 1-butenyl, 2-butenyl, 3-butenyl; alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantly, decahydro-naphthalenyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuranyl, tetrahydrothienyl, tetrahydrothienyl, piperazinyl, decahydroquinolinyl, decahydro-isoquinolinyl, decahydro-quinoxalinyl, decahydro-quinazolinyl; alkoxy, in particular $C_1$-$C_6$ alkoxy, e.g. $C_1$, $C_2$, $C_3$, $C_4$, $C_5$, or $C_6$ alkoxy, preferably methoxy, ethoxy, propoxy, iso-propoxy, butoxy, iso-butoxy, tert-butoxy, pentoxy, or hexoxy; aryl, in particular phenyl, naphthalenyl or anthracenyl; aralkyl; preferably $C_1$-$C_6$ aralkyl, e.g. $C_1$, $C_2$, $C_3$, $C_4$, $C_5$, or $C_6$ aralkyl; heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; and —$NR^6R^7$;

A is selected from the group consisting of alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_1$-$C_6$ alkenyl, e.g. $C_1$, $C_2$, $C_3$, $C_4$, $C_5$, or $C_6$ alkenyl, preferably methenyl, ethenyl, 1-propenyl, 2-propenyl, 1-iso-propenyl, 2-iso-propenyl, 1-butenyl, 2-butenyl, 3-butenyl; alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantly, decahydro-naphthalenyl; alkoxy, in particular $C_1$-$C_6$ alkoxy, e.g. $C_1$, $C_2$, $C_3$, ticular phenyl, naphthalenyl or anthracenyl; heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; and aralkyl, preferably $C_1$-$C_6$ aralkyl, e.g. $C_1$, $C_2$, $C_3$, $C_4$, $C_5$, or $C_6$ aralkyl; or together form a heteroaryl, in particular, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, indolyl, isoindolyl, 1H-indazolyl, benzimidazolyl, indoxazinyl, 2,1-benzisoxazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; optionally substituted;

$R^8$ and $R^9$ is each independently selected from the group consisting of hydrogen; alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_2$-$C_6$ alkenyl, e.g. $C_2$, $C_3$, $C_4$, $C_5$, or $C_6$ alkenyl, preferably ethenyl, 1-pro- $C_4$, $C_5$, or $C_6$ alkoxy, preferably methoxy, ethoxy, propoxy, iso-propoxy, butoxy, iso-butoxy, tert-butoxy, pentoxy, or hexoxy; alkoxyalkyl, in particular $C_1$-$C_6$-alkoxy-$C_1$-$C_6$-alkyl, e.g. methoxymethyl, ethoxymethyl, propoxymethyl, methoxyethyl, ethoxyethyl, propoxyethyl, methoxypropyl, ethoxypropyl, or propoxypropyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuranyl, tetrahydrothienyl, tetrahydrothienyl, piperazinyl, decahydroquinolinyl, decahydro-isoquinolinyl, decahydro-quinoxalinyl, decahydro-quinazolinyl; an alicyclic system, which may comprise one or more heteroatoms, e.g. 1, 2, 3, or 4, preferably selected from the group consisting of O, S, or N; in particular 1,2-dihydropyridinyl, 1,2,5,6-tetrahydropyridinyl, 1,2,3,4-tetrahydropyridyl, 1,2-dihydropyrazyl, 1,2,3,4-tetrahydropyrazyl, cyclopropenyl, cyclobutenyl, cyclopentenyl, cyclohexenyl, cycloheptenyl; aryl, in particular phenyl, naphthalenyl or anthracenyl; and heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; optionally substituted;

(iii) cyclopropenyl, cyclobutenyl, cyclopentenyl, cyclohexenyl, cycloheptenyl, cyclooctyl, cyclononenyl, cyclodecenyl, cyclodecdienyl, spiro[3,3]heptenyl, spiro[3,4]octenyl, spiro[4,3]octenyl, spiro[3,5]nonenyl, spiro[5,3]nonenyl, spiro[3,6]decenyl, spiro[6,3]decenyl, spiro[4,5]decenyl, spiro[5,4]decenyl, bicyclo[4.1.0]heptenyl, bicyclo[3.2.0]heptenyl, bicyclo[2.2.1]heptenyl, bicyclo[2.2.2]octenyl, bicyclo[5.1.0]octenyl, bicyclo[4.2.0]octenyl, bicyclo[5.3.0]decenyl, hexahydro-pentalenyl, hexahydro-indenyl, octahydro-azulenyl, or octahydro-naphthalenyl, or a derivative thereof, wherein 1, 2 or 3 carbon atoms are replaced by a heteroatom each independently selected from the group consisting of nitrogen, sulphur, or oxygen; optionally substituted 1 to 14 times, i.e. 1, 2, 3, 4, 5, 6, 7, 8, 9, 10, 11, 12, 13, or 14 times, depending on the number of available valences with a substituent which is in each instance independently selected from the group consisting of halogen, in particular F, Cl, Br or I; —$NO_2$; —CN; —$OR^6$; —$NR^6R^7$; —$COOR^6$; —$CONR^6R^7$; —$NR^8COR^9$; —$NR^8COR^9$; —$NR^8CONR^6R^7$; —$NR^9SO_2A$; —$COR^6$; —$SO_2NR^6R^7$; —$OOCR^8$; —$CR^8R^9OH$; $R^8OH$; and -A or two substituents on adjacent carbon or heteroatoms atoms—as the case may be—form together with an oxygen atom an epoxy group or a cycloalkyl, cycloheteroalkyl, alicyclic system, aryl or heteroaryl;

$R^6$ and $R^7$ is each independently selected from the group consisting of hydrogen, alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_2$-$C_6$ alkenyl, e.g. $C_2$, $C_3$, $C_4$, $C_5$, or $C_6$ alkenyl, preferably ethenyl, 1-propenyl, 2-propenyl, 1-iso-propenyl, 2-iso-propenyl, 1-butenyl, 2-butenyl, 3-butenyl; alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydropentalenyl, octahydro-indenyl, decahydro-azulenyl, adamantly, decahydro-naphthalenyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5]decyl, 1,7 diaza-spiro-[4,5]decyl, 1,6 diaza-spiro[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuranyl, tetrahydrothienyl, tetrahydrothienyl, piperazinyl, decahydroquinolinyl, decahydro-isoquinolinyl, decahydro-quinoxalinyl, decahydro-quinazolinyl; aryl, in particular phenyl, naphthalenyl or anthracenyl; heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; and aralkyl, preferably $C_1$-$C_6$ aralkyl, e.g. $C_1$, $C_2$, $C_3$, $C_4$, $C_5$, or $C_6$ aralkyl; or together form a heteroaryl, in particular, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, indolyl, isoindolyl, 1H-indazolyl, benzimidazolyl, indoxazinyl, 2,1-benzisoxazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; optionally substituted;

$R^8$ and $R^9$ is each independently selected from the group consisting of hydrogen; alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_2$-$C_6$ alkenyl, e.g. $C_2$, $C_3$, $C_4$, $C_5$, or $C_6$ alkenyl, preferably ethenyl, 1-propenyl, 2-propenyl, 1-iso-propenyl, 2-iso-propenyl, 1-butenyl, 2-butenyl, 3-butenyl; alkynyl, in particular $C_2$-$C_6$ alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantly, decahydro-naphthalenyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuranyl, tetrahydrothienyl, tetrahydrothienyl, piperazinyl, decahydro-quinolinyl, decahydro-isoquinolinyl, decahydro-quinoxalinyl, decahydro-quinazolinyl; alkoxy, in particular $C_1$-$C_6$ alkoxy, e.g. $C_1$, $C_2$, $C_3$, $C_4$, $C_5$, or $C_6$ alkoxy, preferably methoxy, ethoxy, propoxy, iso-propoxy, butoxy, iso-butoxy, tert-butoxy, pentoxy, or hexoxy; aryl, in particular phenyl, naphthalenyl or anthracenyl; aralkyl; preferably $C_1$-$C_6$ aralkyl, e.g. $C_1$, $C_2$, $C_3$, $C_4$, $C_5$, or $C_6$ aralkyl; heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; and —$NR^6R^7$;

A is selected from the group consisting of alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_1$-$C_6$ alkenyl, e.g. $C_1$, $C_2$, $C_3$, $C_4$, $C_5$, or $C_6$ alkenyl, preferably methenyl, ethenyl, 1-propenyl, 2-propenyl, 1-iso-propenyl, 2-iso-propenyl, 1-butenyl, 2-butenyl, 3-butenyl; alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantly, decahydro-naphthalenyl; alkoxy, in particular $C_1$-$C_6$ alkoxy, e.g. $C_1$, $C_2$, $C_3$, $C_4$, $C_5$, or $C_6$ alkoxy, preferably methoxy, ethoxy, propoxy, iso-propoxy, butoxy, iso-butoxy, tert-butoxy, pentoxy, or hexoxy; alkoxyalkyl, in particular $C_1$-$C_6$-alkoxy-$C_1$-$C_6$-alkyl, e.g. methoxymethyl, ethoxymethyl, propoxymethyl, methoxyethyl, ethoxyethyl, propoxyethyl, methoxypropyl, ethoxypropyl, or propoxypropyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuranyl, tetrahydrothienyl, tetrahydrothienyl, piperazinyl, decahydroquinolinyl, decahydro-isoquinolinyl, decahydro-quinoxalinyl, decahydro-quinazolinyl; an alicyclic system, which may comprise one or more heteroatoms, e.g. 1, 2, 3, or 4, preferably selected from the group consisting of O, S, or N; in particular 1,2-dihydropyridinyl, 1,2,5,6-tetrahydropyridinyl, 1,2,3,4-tetrahydropyridyl, 1,2-dihydropyrazyl, 1,2,3,4-tetrahydropyrazyl, cyclopropenyl, cyclobutenyl, cyclopentenyl, cyclohexenyl, cycloheptenyl; aryl, in particular phenyl, naphthalenyl or anthracenyl; and heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; optionally substituted;

(iv) phenyl, naphthalenyl or anthracenyl;

optionally substituted 1 to 9 times, i.e. 1, 2, 3, 4, 5, 6, 7, 8, or 9 times, depending on the number of available valences with a substituent which is in each instance independently selected from the group consisting of halogen, in particular F, Cl, Br or I; —$NO_2$; —CN; —$OR^6$; —$NR^6R^7$; —$COOR^6$; —$CONR^6R^7$; —$NR^8COR^9$; —$NR^8COR^9$; —$NR^8CONR^6R^7$; —$NR^9SO_2A$; —$COR^6$—$SO_2NR^6R^7$; —$OOCR^8$; —$CR^8R^9OH$; $R^8OH$; and -A or two substituents on adjacent carbon atoms together form an alicyclic system, aryl or heteroaryl;

$R^6$ and $R^7$ is each independently selected from the group consisting of hydrogen, alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_2$-$C_6$ alkenyl, e.g. $C_2$, $C_3$, $C_4$, $C_5$, or $C_6$ alkenyl, preferably ethenyl, 1-propenyl, 2-propenyl, 1-iso-propenyl, 2-iso-propenyl, 1-butenyl, 2-butenyl, 3-butenyl; alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo

[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantly, decahydro-naphthalenyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuranyl, tetrahydrothienyl, tetrahydrothienyl, piperazinyl, decahydroquinolinyl, decahydro-isoquinolinyl, decahydro-quinoxalinyl, decahydro-quinazolinyl; aryl, in particular phenyl, naphthalenyl or anthracenyl; heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, indolyl, isoindolyl, 1H-indazolyl, benzimidazolyl, indoxazinyl, 2,1-benzisoxazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; and aralkyl, preferably $C_1$-$C_6$ aralkyl, e.g. $C_1$, $C_2$, $C_3$, $C_4$, $C_5$, or $C_6$ aralkyl; or together form a heteroaryl, in particular, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, indolyl, isoindolyl, 1H-indazolyl, benzimidazolyl, indoxazinyl, 2,1-benzisoxazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; optionally substituted;

$R^8$ and $R^9$ is each independently selected from the group consisting of hydrogen; alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_2$-$C_6$ alkenyl, e.g. $C_2$, $C_3$, $C_4$, $C_5$, or $C_6$ alkenyl, preferably ethenyl, 1-propenyl, 2-propenyl, 1-iso-propenyl, 2-iso-propenyl, 1-butenyl, 2-butenyl, 3-butenyl; alkynyl, in particular $C_2$-$C_6$ alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantly, decahydro-naphthalenyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuranyl, tetrahydrothienyl, tetrahydrothienyl, piperazinyl, decahydro-quinolinyl, decahydro-isoquinolinyl, decahydro-quinoxalinyl, decahydro-quinazolinyl; alkoxy, in particular $C_1$-$C_6$ alkoxy, e.g. $C_1$, $C_2$, $C_3$, $C_4$, $C_5$, or $C_6$ alkoxy, preferably methoxy, ethoxy, propoxy, iso-propoxy, butoxy, iso-butoxy, tert-butoxy, pentoxy, or hexoxy; aryl, in particular phenyl, naphthalenyl or anthracenyl; aralkyl; preferably $C_1$-$C_6$ aralkyl, e.g. $C_1$, $C_2$, $C_3$, $C_4$, $C_5$, or $C_6$ aralkyl; heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; and —$NR^6R^7$;

A is selected from the group consisting of alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_1$-$C_6$ alkenyl, e.g. $C_1$, $C_2$, $C_3$, $C_4$, $C_5$, or $C_6$ alkenyl, preferably methenyl, ethenyl, 1-propenyl, 2-propenyl, 1-iso-propenyl, 2-iso-propenyl, 1-butenyl, 2-butenyl, 3-butenyl; alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantly, decahydro-naphthalenyl; alkoxy, in particular $C_1$-$C_6$ alkoxy, e.g. $C_1$, $C_2$, $C_3$, $C_4$, $C_5$, or $C_6$ alkoxy, preferably methoxy, ethoxy, propoxy, iso-propoxy, butoxy, iso-butoxy, tert-butoxy, pentoxy, or hexoxy; alkoxyalkyl, in particular $C_1$-$C_6$-alkoxy-$C_1$-$C_6$-alkyl, e.g. methoxymethyl, ethoxymethyl, propoxymethyl, methoxyethyl, ethoxyethyl, propoxyethyl, methoxypropyl, ethoxypropyl, or propoxypropyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuranyl, tetrahydrothienyl, tetrahydrothienyl, piperazinyl, decahydroquinolinyl, decahydro-isoquinolinyl, decahydro-quinoxalinyl, decahydro-quinazolinyl; an alicyclic system, which may comprise one or more heteroatoms, e.g. 1, 2, 3, or 4, preferably selected from the group consisting of O, S, or N; in particular 1,2-dihydropyridinyl, 1,2,5,6-tetrahydropyridinyl, 1,2,3,4-tetrahydropyridyl, 1,2-dihydropyrazyl, 1,2,3,4-tetrahydropyrazyl, cyclopropenyl, cyclobutenyl, cyclopentenyl, cyclohexenyl, cycloheptenyl; aryl, in particular phenyl, naphthalenyl or anthracenyl; and heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; optionally substituted;

or (v) furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, and 1,2,4-benzotriazinyl; optionally substituted 1 to 14 times, i.e. 1, 2, 3, 4, 5, 6, 7, 8, 9, 10, 11, 12, 13, or 14 times, depending on the number of available valences with a substituent which is in each instance independently selected from the group consisting of halogen, in particular F, Cl, Br or I; —$NO_2$; —CN; —$OR^6$; —$NR^6R^7$; —$COOR^6$; —$CONR^6R^7$; —$NR^8COR^9$; —$NR^8COR^9$; —$NR^8CONR^6R^7$; —$NR^9SO_2A$; —$COR^6$; —$OOCR^8$; —$CR^8R^9OH$; $R^8OH$; and -A or two substituents on adjacent carbon or heteroatoms—as the case may be—form together with an oxygen atom an epoxy group or an alicyclic system, aryl or heteroaryl;

$R^6$ and $R^7$ is each independently selected from the group consisting of hydrogen, alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_2$-$C_6$ alkenyl, e.g. $C_2$, $C_3$, $C_4$, $C_5$, or $C_6$ alkenyl, preferably ethenyl, 1-propenyl, 2-propenyl, 1-iso-propenyl, 2-iso-propenyl, 1-butenyl, 2-butenyl, 3-butenyl; alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantly, decahydro-naphthalenyl; heterocycloalkyl, e.g. $C_3$-$C_{14}$-heterocycloalkyl, e.g. $C_3$, $C_4$, $C_5$, $C_6$, $C_2$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuranyl, tetrahydrothienyl, tetrahydrothienyl, piperazinyl, decahydroquinolinyl, decahydro-isoquinolinyl, decahydro-quinoxalinyl, decahydro-quinazolinyl; aryl, in particular phenyl, naphthalenyl or anthracenyl; heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; and aralkyl, preferably $C_1$-$C_6$ aralkyl, e.g. $C_1$, $C_2$, $C_3$, $C_4$, $C_5$, or $C_6$ aralkyl; or together form a heteroaryl, in particular, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, indolyl, isoindolyl, 1H-indazolyl, benzimidazolyl, indoxazinyl, 2,1-benzisoxazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; optionally substituted;

$R^8$ and $R^9$ is each independently selected from the group consisting of hydrogen; alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_2$-$C_6$ alkenyl, e.g. $C_2$, $C_3$, $C_4$, $C_5$, or $C_6$ alkenyl, preferably ethenyl, 1-propenyl, 2-propenyl, 1-iso-propenyl, 2-iso-propenyl, 1-butenyl, 2-butenyl, 3-butenyl; alkynyl, in particular $C_2$-$C_6$ alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantly, decahydro-naphthalenyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuranyl, tetrahydrothienyl, tetrahydrothienyl, piperazinyl, decahydro-quinolinyl, decahydro-isoquinolinyl, decahydro-quinoxalinyl, decahydro-quinazolinyl; alkoxy, in particular $C_1$-$C_6$ alkoxy, e.g. $C_1$, $C_2$, $C_3$, $C_4$, $C_5$, or $C_6$ alkoxy, preferably methoxy, ethoxy, propoxy, iso-propoxy, butoxy, iso-butoxy, tert-butoxy, pentoxy, or hexoxy; aryl, in particular phenyl, naphthalenyl or anthracenyl; aralkyl; preferably $C_1$-$C_6$ aralkyl, e.g. $C_1$, $C_2$, $C_3$, $C_4$, $C_5$, or $C_6$ aralkyl; heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; and —$NR^6R^7$;

A is selected from the group consisting of alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, isobutyl, tert-butyl, pentyl, hexyl; alkenyl, in particular $C_1$-$C_6$ alkenyl, e.g. $C_1$, $C_2$, $C_3$, $C_4$, $C_5$, or $C_6$ alkenyl, preferably methenyl, ethenyl, 1-propenyl, 2-propenyl, 1-iso-propenyl, 2-iso-propenyl, 1-butenyl, 2-butenyl, 3-butenyl; alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantly, decahydro-naphthalenyl; alkoxy, in particular $C_1$-$C_6$ alkoxy, e.g. $C_1$, $C_2$, $C_3$, $C_4$, $C_5$, or $C_6$ alkoxy, preferably methoxy, ethoxy, propoxy, iso-propoxy, butoxy, iso-butoxy, tert-butoxy, pentoxy, or hexoxy; alkoxyalkyl, in particular $C_1$-$C_6$-alkoxy-$C_1$-$C_6$-alkyl, e.g. methoxymethyl, ethoxymethyl, propoxymethyl, methoxyethyl, ethoxyethyl, propoxyethyl, methoxypropyl, ethoxypropyl, or propoxypropyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuranyl, tetrahydrothienyl, tetrahydrothienyl, piperazinyl, decahydroquinolinyl, decahydro-isoquinolinyl, decahydro-quinoxalinyl, decahydro-quinazolinyl; an alicyclic system, which may comprise one or more heteroatoms, e.g. 1, 2, 3, or 4, preferably selected from the group consisting of O, S, or N; in particular 1,2-dihydropyridinyl, 1,2,5,6-tetrahydropyridinyl, 1,2,3,4-tetrahydropyridyl, 1,2-dihydropyrazyl, 1,2,3,4-tetrahydropyrazyl, cyclopropenyl, cyclobutenyl, cyclopentenyl, cyclohexenyl, cycloheptenyl; aryl, in particular phenyl, naphthalenyl or anthracenyl; and heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; optionally substituted.

In a preferred method of the present invention the potential agonist or potential antagonist structurally related to artemorin or parthenolide has a structure according to formula (II)

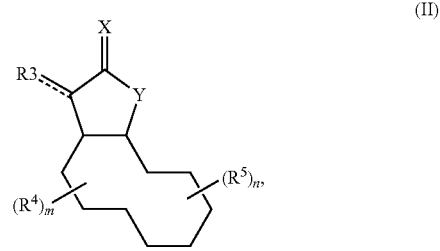

(II)

wherein
$R^3$ is H, OH, alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_1$-$C_6$ alkenyl, e.g. $C_1$, $C_2$, $C_3$, $C_4$, $C_5$, or $C_6$ alkenyl, preferably methenyl, ethenyl, 1-propenyl, 2-propenyl, 1-iso-propenyl, 2-iso-propenyl, 1-butenyl, 2-butenyl, 3-butenyl; alkoxy, in particular $C_1$-$C_6$ alkoxy, e.g. $C_1$, $C_2$, $C_3$, $C_4$, $C_5$, or $C_6$ alkoxy, preferably methoxy, ethoxy, propoxy, iso-propoxy, butoxy, iso-butoxy, tert-butoxy, pentoxy, or hexoxy; alkoxyalkyl, in particular $C_1$-$C_6$ alkoxy-$C_1$-$C_6$ alkyl, e.g. methoxymethyl, ethoxymethyl, propoxymethyl, methoxyethyl, ethoxyethyl, propoxyethyl, methoxypropyl, ethoxypropyl, or propoxypropyl; preferably $C_1$-$C_6$ alkyl, more preferably methyl; optionally substituted;

$R^4$ is in each instance independently selected from the group consisting of halogen, —$NO_2$, —$CN$, —$OR^6$, —$NR^6R^7$, —$COOR^6$, —$CONR^6R^7$, —$NR^8COR^9$, —$NR^8COR^9$, —$NR^8CONR^6R^7$, —$NR^9SO_2A$, —$COR^E$, —$SO_2NR^6R^7$, —$OOCR^8$, —$CR^8R^9OH$, $R^8OH$, and -A or two substituents on adjacent carbon atoms form together with an oxygen atom an epoxy group or a cycloalkyl, cycloheteroalkyl, alicyclic system, aryl or heteroaryl;

$R^5$ is in each instance independently selected from the group consisting of halogen, —$NO_2$, —$CN$, —$OR^6$, —$NR^6R^7$, —$COOR^6$, —$CONR^6R^7$, —$NR^8COR^9$, —$NR^8COR^9$, —$NR^8CONR^6R^7$, —$NR^9SO_2A$, —$COR^E$, —$SO_2NR^6R^7$, —$OOCR^8$, —$CR^8R^9OH$, $R^8OH$, and -A;

$R^6$ and $R^7$ is each independently selected from the group consisting of hydrogen, alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_2$-$C_6$ alkenyl, e.g. $C_2$, $C_3$, $C_4$, $C_5$, or $C_6$ alkenyl, preferably ethenyl, 1-propenyl, 2-propenyl, 1-iso-propenyl, 2-iso-propenyl, 1-butenyl, 2-butenyl, 3-butenyl; alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantly, decahydro-naphthalenyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro-[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuranyl, tetrahydrothienyl, tetrahydrothienyl, piperazinyl, decahydroquinolinyl, decahydro-isoquinolinyl, decahydro-quinoxalinyl, decahydro-quinazolinyl; aryl, in particular phenyl, naphthalenyl or anthracenyl; heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; and aralkyl, preferably $C_1$-$C_6$ aralkyl, e.g. $C_1$, $C_2$, $C_3$, $C_4$, $C_5$, or $C_6$ aralkyl; or together form a heteroaryl, in particular, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, indolyl, isoindolyl, 1H-indazolyl, benzimidazolyl, indoxazinyl, 2,1-benzisoxazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; optionally substituted;

$R^8$ and $R^9$ is each independently selected from the group consisting of hydrogen; alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_2$-$C_6$ alkenyl, e.g. $C_2$, $C_3$, $C_4$, $C_5$, or $C_6$ alkenyl, preferably ethenyl, 1-propenyl, 2-propenyl, 1-iso-propenyl, 2-iso-propenyl, 1-butenyl, 2-butenyl, 3-butenyl; alkynyl, in particular $C_2$-$C_6$ alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantly, decahydro-naphthalenyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuranyl, tetrahydrothienyl, tetrahydrothienyl, piperazinyl, decahydro-quinolinyl, decahydro-isoquinolinyl, decahydro-quinoxalinyl, decahydro-quinazolinyl; alkoxy, in particular $C_1$-$C_6$ alkoxy, e.g. $C_1$, $C_2$, $C_3$, $C_4$, $C_5$, or $C_6$ alkoxy, preferably methoxy, ethoxy, propoxy, iso-propoxy, butoxy, iso-butoxy, tert-butoxy, pentoxy, or hexoxy; aryl, in particular phenyl, naphthalenyl or anthracenyl; aralkyl; preferably $C_1$-$C_6$ aralkyl, e.g. $C_1$, $C_2$, $C_3$, $C_4$, $C_5$, or $C_6$ aralkyl; heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; and —$NR^6R^7$;

A is selected from the group consisting of alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_1$-$C_6$ alkenyl, e.g. $C_1$, $C_2$, $C_3$, $C_4$, $C_5$, or $C_6$ alkenyl, preferably methenyl, ethenyl, 1-propenyl, 2-propenyl, 1-iso-propenyl, 2-iso-propenyl, 1-butenyl, 2-butenyl, 3-butenyl; alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantly, decahydro-naphthalenyl; alkoxy, in particular $C_1$-$C_6$ alkoxy, e.g. $C_1$, $C_2$, $C_3$, $C_4$, $C_5$, or $C_6$ alkoxy, preferably methoxy, ethoxy, propoxy, iso-propoxy, butoxy, iso-butoxy, tert-butoxy, pentoxy, or hexoxy; alkoxyalkyl, in particular $C_1$-$C_6$-alkoxy-$C_1$-$C_6$-alkyl, e.g. methoxymethyl, ethoxymethyl, propoxymethyl, methoxyethyl, ethoxyethyl, propoxyethyl, methoxypropyl, ethoxypropyl, or propoxypropyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuranyl, tetrahydrothienyl, tetrahydrothienyl, piperazinyl, decahydroquinolinyl, decahydro-isoquinolinyl, decahydro-quinoxalinyl, decahydro-quinazolinyl; an alicyclic system, which may comprise one or more heteroatoms, e.g. 1, 2, 3, or 4, preferably selected from the group consisting of O, S, or N; in particular 1,2-dihydropyridinyl, 1,2,5,6-tetrahydropyridinyl, 1,2,3,4-tetrahydropyridyl, 1,2-dihydropyrazyl, 1,2,3,4-tetrahydropyrazyl, cyclopropenyl, cyclobutenyl, cyclopentenyl, cyclohexenyl, cycloheptenyl; aryl, in particular phenyl, naphthalenyl or anthracenyl; and heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; optionally substituted;

m is an integer from 0 to 6, i.e. 0, 1, 2, 3, 4, 5, or 6; preferably 1;

n is an integer from 0 to 8, i.e. 0, 1, 2, 3, 4, 5, 6, 7, or 8, preferably 2;

X is O or S; preferably O;

Y is O or NH or S; preferably O; and the cyclodecyl may contain one, two or three double bonds, preferably one double bond and the dashed bond may be present or not, preferably the dashed bond is present.

It is further preferred that at least two substituents $R^4$ and/or $R^5$ have the meaning -A.

In a further preferred embodiment the potential agonist or potential antagonist structurally related to artemorin has a structure according to formula (III)

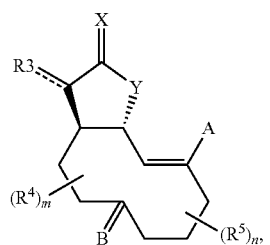

(III)

wherein $R^3$ is H, OH, alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_1$-$C_6$ alkenyl, e.g. $C_1$, $C_2$, $C_3$, $C_4$, $C_5$, or $C_6$ alkenyl, preferably methenyl, ethenyl, 1-propenyl, 2-propenyl, 1-iso-propenyl, 2-iso-propenyl, 1-butenyl, 2-butenyl, 3-butenyl; alkoxy, in particular $C_1$-$C_6$ alkoxy, e.g. $C_1$, $C_2$, $C_3$, $C_4$, $C_5$, or $C_6$ alkoxy, preferably methoxy, ethoxy, propoxy, iso-propoxy, butoxy, iso-butoxy, tert-butoxy, pentoxy, or hexoxy; alkoxyalkyl, in particular $C_1$-$C_6$ alkoxy-$C_1$-$C_6$ alkyl, e.g. methoxymethyl, ethoxymethyl, propoxymethyl, methoxyethyl, ethoxyethyl, propoxyethyl, methoxypropyl, ethoxypropyl, or propoxypropyl; preferably $C_1$-$C_6$ alkyl, more preferably methyl; optionally substituted;

$R^4$ is in each instance independently selected from the group consisting of halogen, —$NO_2$, —CN, —$OR^6$, —$NR^6R^7$, —$COOR^6$, —$CONR^6R^7$, —$NR^8COR^9$, —$NR^8COR^9$, —$NR^8CONR^6R^7$, —$NR^9SO_2A$, —$COR^E$, —$SO_2NR^6R^7$, —$OOCR^8$, —$CR^8R^9OH$, $R^8OH$, and -A;

$R^5$ is in each instance independently selected from the group consisting of halogen, —$NO_2$, —CN, —$OR^6$, —$NR^6R^7$, —$COOR^6$, —$CONR^6R^7$, —$NR^8COR^9$, —$NR^8COR^9$, —$NR^8CONR^6R^7$, —$NR^9SO_2A$, —$COR^E$, —$SO_2NR^6R^7$, —$OOCR^8$, —$CR^8R^9OH$, $R^8OH$, and -A;

$R^6$ and $R^7$ is each independently selected from the group consisting of hydrogen, alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_2$-$C_6$ alkenyl, e.g. $C_2$, $C_3$, $C_4$, $C_5$, or $C_6$ alkenyl, preferably ethenyl, 1-propenyl, 2-propenyl, 1-iso-propenyl, 2-iso-propenyl, 1-butenyl, 2-butenyl, 3-butenyl; alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantly, decahydro-naphthalenyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuranyl, tetrahydrothienyl, tetrahydrothienyl, piperazinyl, decahydroquinolinyl, decahydro-isoquinolinyl, decahydro-quinoxalinyl, decahydro-quinazolinyl; aryl, in particular phenyl, naphthalenyl or anthracenyl; heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; and aralkyl, preferably $C_1$-$C_6$ aralkyl, e.g. $C_1$, $C_2$, $C_3$, $C_4$, $C_5$, or $C_6$ aralkyl; or together form a heteroaryl, in particular, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, indolyl, isoindolyl, 1H-indazolyl, benzimidazolyl, indoxazinyl, 2,1-benzisoxazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; optionally substituted;

$R^8$ and $R^9$ is each independently selected from the group consisting of hydrogen; alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_2$-$C_6$ alkenyl, e.g. $C_2$, $C_3$, $C_4$, $C_5$, or $C_6$ alkenyl, preferably ethenyl, 1-propenyl, 2-propenyl, 1-iso-propenyl, 2-iso-propenyl, 1-butenyl, 2-butenyl, 3-butenyl; alkynyl, in particular $C_2$-$C_6$ alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantly, decahydro-naphthalenyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuranyl, tetrahydrothienyl, tetrahydrothienyl, piperazinyl, decahydro-quinolinyl, decahydro-isoquinolinyl, decahydro-quinoxalinyl, decahydro-quinazolinyl; alkoxy, in particular $C_1$-$C_6$ alkoxy, e.g. $C_1$, $C_2$, $C_3$, $C_4$, $C_5$, or $C_6$ alkoxy, preferably methoxy, ethoxy, propoxy, iso-propoxy, butoxy, iso-butoxy, tert-butoxy, pentoxy, or hexoxy; aryl, in particular phenyl, naphthalenyl or anthracenyl; aralkyl; preferably $C_1$-$C_6$ aralkyl, e.g. $C_1$, $C_2$, $C_3$, $C_4$, $C_5$, or $C_6$ aralkyl; heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; and —$NR^6R^7$;

A is selected from the group consisting of alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_1$-$C_6$ alkenyl, e.g. $C_1$, $C_2$, $C_3$, $C_4$, $C_5$, or $C_6$ alkenyl, preferably methenyl, ethenyl, 1-propenyl, 2-propenyl, 1-iso-propenyl, 2-iso-propenyl, 1-butenyl, 2-butenyl, 3-butenyl; alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantly, decahydro-naphthalenyl; alkoxy, in particular $C_1$-$C_6$ alkoxy, e.g. $C_1$, $C_2$, $C_3$, $C_4$, $C_5$, or $C_6$ alkoxy, preferably methoxy, ethoxy, propoxy, iso-propoxy, butoxy, iso-butoxy, tert-butoxy, pentoxy, or hexoxy; alkoxyalkyl, in particular $C_1$-$C_6$-alkoxy-$C_1$-$C_6$-alkyl, e.g. methoxymethyl, ethoxymethyl, propoxymethyl, methoxyethyl, ethoxyethyl, propoxyethyl, methoxypropyl, ethoxypropyl, or propoxypropyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuranyl, tetrahydrothienyl, tetrahydrothienyl, piperazinyl, decahydroquinolinyl, decahydro-isoquinolinyl, decahydro-quinoxalinyl, decahydro-quinazolinyl; an alicyclic system, which may comprise one or more heteroatoms, e.g. 1, 2, 3, or 4, preferably selected from the group consisting of O, S, or N; in particular 1,2-dihydropyridinyl, 1,2,5,6-tetrahydropyridinyl, 1,2,3,4-tetrahydropyridyl, 1,2-dihydropyrazyl, 1,2,3,4-tetrahydropyrazyl, cyclopropenyl, cyclobutenyl, cyclopentenyl, cyclohexenyl, cycloheptenyl; aryl, in particular phenyl, naphthalenyl or anthracenyl; and heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_1$-$C_6$ alkenyl, e.g. $C_1$, $C_2$, $C_3$, $C_4$, $C_5$, or $C_6$ alkenyl, preferably methenyl, ethenyl, 1-propenyl, 2-propenyl, 1-iso-propenyl, 2-iso-propenyl, 1-butenyl, 2-butenyl, 3-butenyl; more preferably methyl; optionally substituted;

B is selected from the group consisting of alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_1$-$C_6$ alkenyl, e.g. $C_1$, $C_2$, $C_3$, $C_4$, $C_5$, or $C_6$ alkenyl, preferably methenyl, ethenyl, 1-propenyl, 2-propenyl, 1-iso-propenyl, 2-iso-propenyl, 1-butenyl, 2-butenyl, 3-butenyl; alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3, 6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantly, decahydro-naphthalenyl; alkoxy, in particular $C_1$-$C_6$ alkoxy, e.g. $C_1$, $C_2$, $C_3$, $C_4$, $C_5$, or $C_6$ alkoxy, preferably methoxy, ethoxy, propoxy, iso-propoxy, butoxy, iso-butoxy, tert-butoxy, pentoxy, or hexoxy; alkoxyalkyl, in particular $C_1$-$C_6$-alkoxy-$C_1$-$C_6$-alkyl, e.g. methoxymethyl, ethoxymethyl, propoxymethyl, methoxyethyl, ethoxyethyl, propoxyethyl, methoxypropyl, ethoxypropyl, or propoxypropyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuranyl, tetrahydrothienyl, tetrahydrothienyl, piperazinyl, decahydroquinolinyl, decahydro-isoquinolinyl, decahydro-quinoxalinyl, decahydro-quinazolinyl; an alicyclic system, which may comprise one or more heteroatoms, e.g. 1, 2, 3, or 4, preferably selected from the group consisting of O, S, or N; in particular 1,2-dihydropyridinyl, 1,2,5,6-tetrahydropyridinyl, 1,2,3,4-tetrahydropyridyl, 1,2-dihydropyrazyl, 1,2,3,4-tetrahydropyrazyl, cyclopropenyl, cyclobutenyl, cyclopentenyl, cyclohexenyl, cycloheptenyl; aryl, in particular phenyl, naphthalenyl or anthracenyl; and heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; preferably alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_1$-$C_6$ alkenyl, e.g. $C_1$, $C_2$, $C_3$, $C_4$, $C_5$, or $C_6$ alkenyl, preferably methenyl, ethenyl, 1-propenyl, 2-propenyl, 1-iso-propenyl, 2-iso-propenyl, 1-butenyl, 2-butenyl, 3-butenyl; more preferably methenyl; optionally substituted;

m is an integer from 0 to 4, i.e. 0, 1, 2, 3 or 4, preferably 1;

n is an integer from 0 to 6, i.e. 0, 1, 2, 3, 4, 5 or 6, preferably 0 or 1;

X is O or S; preferably O;

Y is O or NH or S; preferably O; and the dashed bond may be present or not, preferably the dashed bond is present.

In a preferred method of the present invention the potential agonist or potential antagonist structurally related to aborescin, absinthin, or arglabin has a structure according to formula (IV)

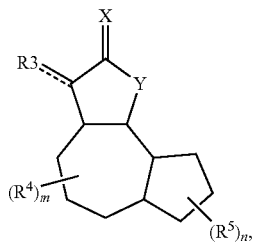

(IV)

wherein $R^3$ is H, OH, alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_1$-$C_6$ alkenyl, e.g. $C_1$, $C_2$, $C_3$, $C_4$, $C_5$, or $C_6$ alkenyl, preferably methenyl, ethenyl, 1-propenyl, 2-propenyl, 1-iso-propenyl, 2-iso-propenyl, 1-butenyl, 2-butenyl, 3-butenyl; alkoxy, in particular $C_1$-$C_6$ alkoxy, e.g. $C_1$, $C_2$, $C_3$, $C_4$, $C_5$, or $C_6$ alkoxy, preferably methoxy, ethoxy, propoxy, iso-propoxy, butoxy, iso-butoxy, tert-butoxy, pentoxy, or hexoxy; alkoxyalkyl, in particular $C_1$-$C_6$ alkoxy-$C_1$-$C_6$ alkyl, e.g. methoxymethyl, ethoxymethyl, propoxymethyl, methoxyethyl, ethoxyethyl, propoxyethyl, methoxypropyl, ethoxypropyl, or propoxypropyl; preferably $C_1$-$C_6$ alkyl, more preferably methyl; optionally substituted;

$R^4$ is in each instance independently selected from the group consisting of halogen, $-NO_2$, $-CN$, $-OR^6$, $-NR^6R^7$, $-COOR^6$, $-CONR^6R^7$, $-NR^8COR^9$, $-NR^8COR^9$, $-NR^8CONR^6R^7$, $-NR^9SO_2A$, $-COR^E$, $-SO_2NR^6R^7$, $-OOCR^8$, $-CR^8R^9OH$, $R^8OH$, and -A or two substituents on adjacent carbon atoms form together with a oxygen atom an epoxy group or a cycloalkyl, cycloheteroalkyl, alicyclic system, aryl or heteroaryl;

$R^5$ is in each instance independently selected from the group consisting of halogen, $-NO_2$, $-CN$, $-OR^6$, $-NR^6R^7$, $-COOR^6$, $-CONR^6R^7$, $-NR^8COR^9$, $-NR^8COR^9$, $-NR^8CONR^6R^7$, $-NR^9SO_2A$, $-COR^6$, $-SO_2NR^6R^7$, $-OOCR^8$, $-CR^8R^9OH$, $R^8OH$, and -A or two substituents on adjacent carbon atoms together with a oxygen atom form an epoxy group or a cycloalkyl, cycloheteroalkyl, alicyclic system, aryl or heteroaryl, optionally substituted;

$R^6$ and $R^7$ is each independently selected from the group consisting of hydrogen, alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_2$-$C_6$ alkenyl, e.g. $C_2$, $C_3$, $C_4$, $C_5$, or $C_6$ alkenyl, preferably ethenyl, 1-propenyl, 2-propenyl, 1-iso-propenyl, 2-iso-propenyl, 1-butenyl, 2-butenyl, 3-butenyl; alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantly, decahydro-naphthalenyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuranyl, tetrahydrothienyl, tetrahydrothienyl, piperazinyl, decahydroquinolinyl, decahydro-isoquinolinyl, decahydro-quinoxalinyl, decahydro-quinazolinyl; aryl, in particular phenyl, naphthalenyl or anthracenyl; heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; and aralkyl, preferably $C_1$-$C_6$ aralkyl, e.g. $C_1$, $C_2$, $C_3$, $C_4$, $C_5$, or $C_6$ aralkyl; or together form a heteroaryl, in particular, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, indolyl, isoindolyl, 1H-indazolyl, benzimidazolyl, indoxazinyl, 2,1-benzisoxazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; optionally substituted; $R^8$ and $R^9$ is each independently selected from the group consisting of hydrogen; alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_2$-$C_6$ alkenyl, e.g. $C_2$, $C_3$, $C_4$, $C_5$, or $C_6$ alkenyl, preferably ethenyl, 1-propenyl, 2-propenyl, 1-iso-propenyl, 2-iso-propenyl, 1-butenyl, 2-butenyl, 3-butenyl; alkynyl, in particular $C_2$-$C_6$ alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantly, decahydro-naphthalenyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuranyl, tetrahydrothienyl, tetrahydrothienyl, piperazinyl, decahydro-quinolinyl, decahydro-isoquinolinyl, decahydro-quinoxalinyl, decahydro-quinazolinyl; alkoxy, in particular $C_1$-$C_6$ alkoxy, e.g. $C_1$, $C_2$, $C_3$, $C_4$, $C_5$, or $C_6$ alkoxy, preferably methoxy, ethoxy, propoxy, iso-propoxy, butoxy, iso-butoxy, tert-butoxy, pentoxy, or hexoxy; aryl, in particular phenyl, naphthalenyl or anthracenyl; aralkyl; preferably $C_1$-$C_6$ aralkyl, e.g. $C_1$, $C_2$, $C_3$, $C_4$, $C_5$, or $C_6$ aralkyl; heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; and —$NR^6R^7$;

A is selected from the group consisting of alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_1$-$C_6$ alkenyl, e.g. $C_1$, $C_2$, $C_3$, $C_4$, $C_5$, or $C_6$ alkenyl, preferably methenyl, ethenyl, 1-propenyl, 2-propenyl, 1-iso-propenyl, 2-iso-propenyl, 1-butenyl, 2-butenyl, 3-butenyl; alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantly, decahydro-naphthalenyl; alkoxy, in particular $C_1$-$C_6$ alkoxy, e.g. $C_1$, $C_2$, $C_3$, $C_4$, $C_5$, or $C_6$ alkoxy, preferably methoxy, ethoxy, propoxy, iso-propoxy, butoxy, iso-butoxy, tert-butoxy, pentoxy, or hexoxy; alkoxyalkyl, in particular $C_1$-$C_6$-alkoxy-$C_1$-$C_6$-alkyl, e.g. methoxymethyl, ethoxymethyl, propoxymethyl, methoxyethyl, ethoxyethyl, propoxyethyl, methoxypropyl, ethoxypropyl, or propoxypropyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuranyl, tetrahydrothienyl, tetrahydrothienyl, piperazinyl, decahydro-quinolinyl, decahydro-isoquinolinyl, decahydro-quinoxalinyl, decahydro-quinazolinyl; an alicyclic system, which may comprise one or more heteroatoms, e.g. 1, 2, 3, or 4, preferably selected from the group consisting of O, S, or N; in particular 1,2-dihydropyridinyl, 1,2,5,6-tetrahydropyridinyl, 1,2,3,4-tetrahydropyridyl, 1,2-dihydropyrazyl, 1,2,3,4-tetrahydropyrazyl, cyclopropenyl, cyclobutenyl, cyclopentenyl, cyclohexenyl, cycloheptenyl; aryl, in particular phenyl, naphthalenyl or anthracenyl; and heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; optionally substituted;

m is an integer from 0 to 8, i.e. 0, 1, 2, 3, 4, 5, 6, 7, or 8, preferably 3;

n is an integer from 0 to 6, i.e. 0, 1, 2, 3, 4, 5, or 6; preferably 1;

X is O or S; preferably O;

Y is O or NH or S; preferably O; and the bicyclo[5.3.0]decyl moiety (formed of $R^1$ and $R^2$) may contain one, two or three double bonds, preferably one double bond and the dashed bond is present or not, preferably the dashed bond is present.

In a preferred method of the present invention the potential agonist or potential antagonist structurally related to arglabin or arborsecin has a structure according to formula (V)

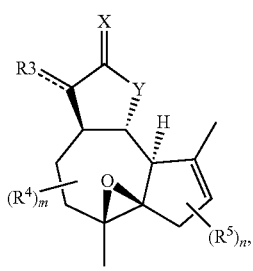

(V)

wherein $R^3$ is H, OH, alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_1$-$C_6$ alkenyl, e.g. $C_1$, $C_2$, $C_3$, $C_4$, $C_5$, or $C_6$ alkenyl, preferably methenyl, ethenyl, 1-propenyl, 2-propenyl, 1-iso-propenyl, 2-iso-propenyl, 1-butenyl, 2-butenyl, 3-butenyl; alkoxy, in particular $C_1$-$C_6$ alkoxy, e.g. $C_1$, $C_2$, $C_3$, $C_4$, $C_5$, or $C_6$ alkoxy, preferably methoxy, ethoxy, propoxy, iso-propoxy, butoxy, iso-butoxy, tert-butoxy, pentoxy, or hexoxy; alkoxyalkyl, in particular $C_1$-$C_6$ alkoxy-$C_1$-$C_6$ alkyl, e.g. methoxymethyl, ethoxymethyl, propoxymethyl, methoxyethyl, ethoxyethyl, propoxyethyl, methoxypropyl, ethoxypropyl, or propoxypropyl; preferably $C_1$-$C_6$ alkyl, more preferably methyl; optionally substituted;

$R^4$ is in each instance independently selected from the group consisting of halogen, —$NO_2$, —CN, —$OR^6$, —$NR^6R^7$, —$COOR^6$, —$CONR^6R^7$, —$NR^8COR^9$, —$NR^8COR^9$, —$NR^8CONR^6R^7$, —$NR^9SO_2A$, —$COR^E$, —$SO_2NR^6R^7$, —$OOCR^8$, —$CR^8R^9OH$, $R^8OH$, and -A or two substituents on adjacent carbon atoms form together with a oxygen atom an epoxy group;

$R^5$ is in each instance independently selected from the group consisting of halogen, —$NO_2$, —CN, —$OR^6$, —$NR^6R^7$, —$COOR^6$, —$CONR^6R^7$, —$NR^8COR^9$, —$NR^8COR^9$, —$NR^8CONR^6R^7$, —$NR^9SO_2A$, —$COR^E$, —$SO_2NR^6R^7$, —$OOCR^8$, —$CR^8R^9OH$, $R^8OH$, and -A;

$R^6$ and $R^7$ is each independently selected from the group consisting of hydrogen, alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_2$-$C_6$ alkenyl, e.g. $C_2$, $C_3$, $C_4$, $C_5$, or $C_6$ alkenyl, preferably ethenyl, 1-propenyl, 2-propenyl, 1-iso-propenyl, 2-iso-propenyl, 1-butenyl, 2-butenyl, 3-butenyl; alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydroazulenyl, adamantly, decahydro-naphthalenyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuranyl, tetrahydrothienyl, tetrahydrothienyl, piperazinyl, decahydroquinolinyl, decahydro-isoquinolinyl, decahydro-quinoxalinyl, decahydro-quinazolinyl; aryl, in particular phenyl, naphthalenyl or anthracenyl; heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; and aralkyl, preferably $C_1$-$C_6$ aralkyl, e.g. $C_1$, $C_2$, $C_3$, $C_4$, $C_5$, or $C_6$ aralkyl; or together form a heteroaryl, in particular, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, indolyl, isoindolyl, 1H-indazolyl, benzimidazolyl, indoxazinyl, 2,1-benzisoxazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; optionally substituted;

$R^8$ and $R^9$ is each independently selected from the group consisting of hydrogen; alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_2$-$C_6$ alkenyl, e.g. $C_2$, $C_3$, $C_4$, $C_5$, or $C_6$ alkenyl, preferably ethenyl, 1-propenyl, 2-propenyl, 1-iso-propenyl, 2-iso-propenyl, 1-butenyl, 2-butenyl, 3-butenyl; alkynyl, in particular $C_2$-$C_6$ alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_2$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro

[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantly, decahydro-naphthalenyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuranyl, tetrahydrothienyl, tetrahydrothienyl, piperazinyl, decahydro-quinolinyl, decahydro-isoquinolinyl, decahydro-quinoxalinyl, decahydro-quinazolinyl; alkoxy, in particular $C_1$-$C_6$ alkoxy, e.g. $C_1$, $C_2$, $C_3$, $C_4$, $C_5$, or $C_6$ alkoxy, preferably methoxy, ethoxy, propoxy, isopropoxy, butoxy, iso-butoxy, tert-butoxy, pentoxy, or hexoxy; aryl, in particular phenyl, naphthalenyl or anthracenyl; aralkyl; preferably $C_1$-$C_6$ aralkyl, e.g. $C_1$, $C_2$, $C_3$, $C_4$, $C_5$, or $C_6$ aralkyl; heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; and —$NR^6R^7$;

A is selected from the group consisting of alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_1$-$C_6$ alkenyl, e.g. $C_1$, $C_2$, $C_3$, $C_4$, $C_5$, or $C_6$ alkenyl, preferably methenyl, ethenyl, 1-propenyl, 2-propenyl, 1-iso-propenyl, 2-iso-propenyl, 1-butenyl, 2-butenyl, 3-butenyl; alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantly, decahydro-naphthalenyl; alkoxy, in particular $C_1$-$C_6$ alkoxy, e.g. $C_1$, $C_2$, $C_3$, $C_4$, $C_5$, or $C_6$ alkoxy, preferably methoxy, ethoxy, propoxy, iso-propoxy, butoxy, iso-butoxy, tert-butoxy, pentoxy, or hexoxy; alkoxyalkyl, in particular $C_1$-$C_6$-alkoxy-$C_1$-$C_6$-alkyl, e.g. methoxymethyl, ethoxymethyl, propoxymethyl, methoxyethyl, ethoxyethyl, propoxyethyl, methoxypropyl, ethoxypropyl, or propoxypropyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuranyl, tetrahydrothienyl, tetrahydrothienyl, piperazinyl, decahydroquinolinyl, decahydro-isoquinolinyl, decahydro-quinoxalinyl, decahydro-quinazolinyl; an alicyclic system, which may comprise one or more heteroatoms, e.g. 1, 2, 3, or 4, preferably selected from the group consisting of O, S, or N; in particular 1,2-dihydropyridinyl, 1,2,5,6-tetrahydropyridinyl, 1,2,3,4-tetrahydropyridyl, 1,2-dihydropyrazyl, 1,2,3,4-tetrahydropyrazyl, cyclopropenyl, cyclobutenyl, cyclopentenyl, cyclohexenyl, cycloheptenyl; aryl, in particular phenyl, naphthalenyl or anthracenyl; and heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; optionally substituted;

m is an integer from 0 to 4, i.e. 0, 1, 2, 3, or 4; preferably 0;
n is an integer from 0 to 3, i.e. 0, 1, 2, or 3; preferably 0;
X is O or S; preferably O;
Y is O or NH or S; preferably O; and
the bicycle[5.3.0]decyl may contain one, two further double bonds, preferably one double bond and the dashed bond may be present or not, preferably the dashed bond is present.

In a preferred method of the present invention the potential agonist or potential antagonist structurally related to absinthin has a structure according to formula (VI)

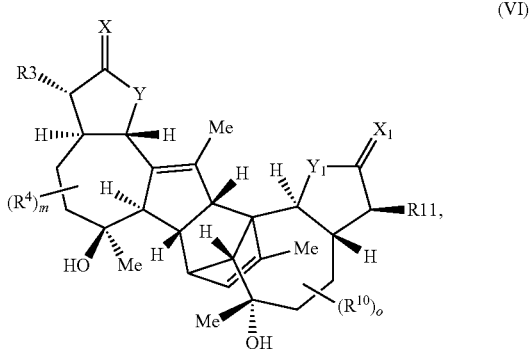

(VI)

wherein
$R^3$ is H, OH, alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_1$-$C_6$ alkenyl, e.g. $C_1$, $C_2$, $C_3$, $C_4$, $C_5$, or $C_6$ alkenyl, preferably methenyl, ethenyl, 1-propenyl, 2-propenyl, 1-iso-propenyl, 2-iso-propenyl, 1-butenyl, 2-butenyl, 3-butenyl; alkoxy, in particular $C_1$-$C_6$ alkoxy, e.g. $C_1$, $C_2$, $C_3$, $C_4$, $C_5$, or $C_6$ alkoxy, preferably methoxy, ethoxy, propoxy, iso-propoxy, butoxy, iso-butoxy, tert-butoxy, pentoxy, or hexoxy; alkoxyalkyl, in particular $C_1$-$C_6$ alkoxy-$C_1$-$C_6$ alkyl, e.g. methoxymethyl, ethoxymethyl, propoxymethyl, methoxyethyl, ethoxyethyl, propoxyethyl, methoxypropyl, ethoxypropyl, or propoxypropyl; preferably $C_1$-$C_6$ alkyl, more preferably methyl; optionally substituted;

$R^4$ is in each instance independently selected from the group consisting of halogen, —$NO_2$, —CN, —$OR^6$, —$NR^6R^7$, —$COOR^6$, —$CONR^6R^7$, —$NR^8COR^9$, —$NR^8COR^9$, —$NR^8CONR^6R^7$, —$NR^9SO_2A$, —$COR^E$, —$SO_2NR^6R^7$, —$OOCR^8$, —$CR^8R^9OH$, $R^8OH$, and -A or two substituents on adjacent carbon atoms form together with a oxygen atom an epoxy group or a cycloalkyl, cycloheteroalkyl, alicyclic system, aryl or heteroaryl, optionally substituted;

$R^{10}$ is in each instance independently selected from the group consisting of halogen, —$NO_2$, —CN, —$OR^6$, —$NR^6R^7$, —$COOR^6$, —$CONR^6R^7$, —$NR^8COR^9$, —$NR^8COR^9$, —$NR^8CONR^6R^7$, —$NR^9SO_2A$, —$COR^E$, —$SO_2NR^6R^7$, —$OOCR^8$, —$CR^8R^9OH$, $R^8OH$, and -A or two substituents on adjacent carbon atoms together with a oxygen atom form an epoxy group or a cycloalkyl, cycloheteroalkyl, alicyclic system, aryl or heteroaryl, optionally substituted;

$R^{11}$ is H, OH, alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_1$-$C_6$ alkenyl, e.g. $C_1$, $C_2$, $C_3$, $C_4$, $C_5$, or $C_6$ alkenyl, preferably methenyl, ethenyl, 1-propenyl, 2-propenyl, 1-iso-propenyl, 2-iso-propenyl, 1-butenyl, 2-butenyl, 3-butenyl; alkoxy, in particular $C_1$-$C_6$ alkoxy, e.g. $C_1$, $C_2$, $C_3$, $C_4$, $C_5$, or $C_6$ alkoxy, preferably methoxy, ethoxy, propoxy, iso-propoxy, butoxy, iso-butoxy, tert-butoxy, pentoxy, or hexoxy; alkoxyalkyl, in particular $C_1$-$C_6$ alkoxy-$C_1$-$C_6$ alkyl, e.g. methoxymethyl, ethoxymethyl, propoxymethyl, methoxyethyl, ethoxyethyl, propoxyethyl, methoxypropyl, ethoxypropyl, or propoxypropyl; preferably $C_1$-$C_6$ alkyl, more preferably methyl; optionally substituted;

$R^6$ and $R^7$ is each independently selected from the group consisting of hydrogen, alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_2$-$C_6$ alkenyl, e.g. $C_2$, $C_3$, $C_4$, $C_5$, or $C_6$ alkenyl, preferably ethenyl, 1-propenyl, 2-propenyl, 1-iso-propenyl, 2-iso-propenyl, 1-butenyl, 2-butenyl, 3-butenyl; alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantly, decahydro-naphthalenyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuranyl, tetrahydrothienyl, tetrahydrothienyl, piperazinyl, decahydroquinolinyl, decahydro-isoquinolinyl, decahydro-quinoxalinyl, decahydro-quinazolinyl; aryl, in particular phenyl, naphthalenyl or anthracenyl; heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; and aralkyl, preferably $C_1$-$C_6$ aralkyl, e.g. $C_1$, $C_2$, $C_3$, $C_4$, $C_5$, or $C_6$ aralkyl; or together form a heteroaryl, in particular, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, indolyl, isoindolyl, 1H-indazolyl, benzimidazolyl, indoxazinyl, 2,1-benzisoxazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; optionally substituted;

$R^8$ and $R^9$ is each independently selected from the group consisting of hydrogen; alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_2$-$C_6$ alkenyl, e.g. $C_2$, $C_3$, $C_4$, $C_5$, or $C_6$ alkenyl, preferably ethenyl, 1-propenyl, 2-propenyl, 1-iso-propenyl, 2-iso-propenyl, 1-butenyl, 2-butenyl, 3-butenyl; alkynyl, in particular $C_2$-$C_6$ alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantly, decahydro-naphthalenyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuranyl, tetrahydrothienyl, tetrahydrothienyl, piperazinyl, decahydro-quinolinyl, decahydro-isoquinolinyl, decahydro-quinoxalinyl, decahydro-quinazolinyl; alkoxy, in particular $C_1$-$C_6$ alkoxy, e.g. $C_1$, $C_2$, $C_3$, $C_4$, $C_5$, or $C_6$ alkoxy, preferably methoxy, ethoxy, propoxy, iso-propoxy, butoxy, iso-butoxy, tert-butoxy, pentoxy, or hexoxy; aryl, in particular phenyl, naphthalenyl or anthracenyl; aralkyl; preferably $C_1$-$C_6$ aralkyl, e.g. $C_1$, $C_2$, $C_3$, $C_4$, $C_5$, or $C_6$ aralkyl; heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; and —NR$^6$R$^7$;

A is selected from the group consisting of alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_1$-$C_6$ alkenyl, e.g. $C_1$, $C_2$, $C_3$, $C_4$, $C_5$, or $C_6$ alkenyl, preferably methenyl, ethenyl, 1-propenyl, 2-propenyl, 1-iso-propenyl, 2-iso-propenyl, 1-butenyl, 2-butenyl, 3-butenyl; alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_2$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantly, decahydro-naphthalenyl; alkoxy, in particular $C_1$-$C_6$ alkoxy, e.g. $C_1$, $C_2$, $C_3$, $C_4$, $C_5$, or $C_6$ alkoxy, preferably methoxy, ethoxy, propoxy, iso-propoxy, butoxy, iso-butoxy, tert-butoxy, pentoxy, or hexoxy; alkoxyalkyl, in particular $C_1$-$C_6$-alkoxy-$C_1$-$C_6$-alkyl, e.g. methoxymethyl, ethoxymethyl, propoxymethyl, methoxyethyl, ethoxyethyl, propoxyethyl, methoxypropyl, ethoxypropyl, or propoxypropyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuranyl, tetrahydrothienyl, tetrahydrothienyl, piperazinyl, decahydroquinolinyl, decahydro-isoquinolinyl, decahydro-quinoxalinyl, decahydro-quinazolinyl; an alicyclic system, which may comprise one or more heteroatoms, e.g. 1, 2, 3, or 4, preferably selected from the group consisting of O, S, or N; in particular 1,2-dihydropyridinyl, 1,2,5,6-tetrahydropyridinyl, 1,2,3,4-tetrahydropyridyl, 1,2-dihydropyrazyl, 1,2,3,4-tetrahydropyrazyl, cyclopropenyl, cyclobutenyl, cyclopentenyl, cyclohexenyl, cycloheptenyl; aryl, in particular phenyl, naphthalenyl or anthracenyl; and heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; optionally substituted;

m is an integer from 0 to 4, i.e. 0, 1, 2, 3, or 4, preferably 1;

o is an integer from 0 to 4, i.e. 0, 1, 2, 3, or 4; preferably 1;

X and $X^1$ is in each instance selected from O or S; preferably is in both instances O;

Y and $Y^1$ is in each instance selected from O or NH or S; preferably is in both instances O; and either of the bicycle[5.3.0]decyl moieties may contain one or two double bonds, preferably one double bond.

In a preferred method of the present invention the potential agonist or potential antagonist structurally related to noscapine has a structure according to formula (VII)

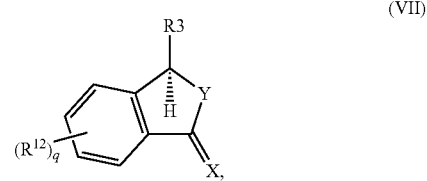

(VII)

wherein $R^3$ is cycloalkyl, in particular $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, bicyclo[5.3.0]decyl, octahydro-pentalenyl, octahydro-indenyl, decahydro-azulenyl, adamantly, or decahydro-naphthalenyl; heterocycloalkyl, preferably $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{1-4}$-heterocycloalkyl, in particular piperidinyl, morpholinyl, 1,3-diazacyclohexane, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuran-3-yl, tetrahydrothien-2-yl, tetrahydrothien-3-yl, piperazinyl, decahydroquinolinyl, decahydro-isoquinolinyl, decahydro-quinoxalinyl, or decahydro-quinazolinyl; an alicyclic system, preferably $C_3$-$C_{14}$-alicyclic system, e.g. $C_3$, $C_4$, $C_5$, $C_6$, $C_7$, $C_8$, $C_9$, $C_{10}$, $C_{11}$, $C_{12}$, $C_{13}$ or $C_{14}$-alicyclic system, in particular cyclopropenyl, cyclobutenyl, cyclopentenyl, cyclohexenyl, cycloheptenyl, cyclooctenyl, cyclononenyl, cyclodecenyl, spiro[3,3]heptenyl, spiro[3,4]octenyl, spiro[4,3]octenyl, spiro[3,5]nonenyl, spiro[5,3]nonenyl, spiro[3,6]decenyl, spiro[6,3]decenyl, spiro[4,5]decenyl, spiro[5,4]decenyl, bicyclo[4.1.0]heptenyl, bicyclo[3.2.0]heptenyl, bicyclo[2.2.1]heptenyl, bicyclo[2.2.2]octenyl, bicyclo[5.1.0]octenyl, bicyclo[4.2.0]octenyl, bicyclo[5.3.0]decenyl, hexahydro-pentalenyl, hexahydro-indenyl, octahydro-azulenyl, or octahydro-naphthalenyl, or a derivative thereof, wherein 1, 2 or 3 carbon atoms are replaced by a heteroatom each independently selected from the group consisting of nitrogen, sulphur, or oxygen; aryl, in particular phenyl, naphthalenyl or anthracenyl; or heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; preferably decahydro-naphthalenyl, cyclodecyl, octahydro-naphthalenyl, or cyclodecenyl; optionally substituted;

$R^{12}$ is in each instance independently selected from the group consisting of halogen, —$NO_2$, —CN, —$OR^6$, —$NR^6R^7$, —$COOR^6$, —$CONR^6R^7$, —$NR^8COR^9$, —$NR^8COR^9$, —$NR^8CONR^6R^7$, —$NR^9SO_2A$, —$COR^E$, —$SO_2NR^6R^7$, —$OOCR^8$, —$CR^8R^9OH$, $R^8OH$, and -A or two substituents on adjacent carbon atoms form together an alicyclic system, aryl or heteroaryl, optionally substituted;

$R^6$ and $R^7$ is each independently selected from the group consisting of hydrogen, alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_2$-$C_6$ alkenyl, e.g. $C_2$, $C_3$, $C_4$, $C_5$, or $C_6$ alkenyl, preferably ethenyl, 1-propenyl, 2-propenyl, 1-iso-propenyl, 2-iso-propenyl, 1-butenyl, 2-butenyl, 3-butenyl; alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantly, decahydro-naphthalenyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuranyl, tetrahydrothienyl, tetrahydrothienyl, piperazinyl, decahydroquinolinyl, decahydro-isoquinolinyl, decahydro-quinoxalinyl, decahydro-quinazolinyl; aryl, in particular phenyl, naphthalenyl or anthracenyl; heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; and aralkyl, preferably $C_1$-$C_6$ aralkyl, e.g. $C_1$, $C_2$, $C_3$, $C_4$, $C_5$, or $C_6$ aralkyl; or together form a heteroaryl, in particular, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, indolyl, isoindolyl, 1H-indazolyl, benzimidazolyl, indoxazinyl, 2,1-benzisoxazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; optionally substituted;

$R^8$ and $R^9$ is each independently selected from the group consisting of hydrogen; alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_2$-$C_6$ alkenyl, e.g. $C_2$, $C_3$, $C_4$, $C_5$, or $C_6$ alkenyl, preferably ethenyl, 1-propenyl, 2-propenyl, 1-iso-propenyl, 2-iso-propenyl, 1-butenyl, 2-butenyl, 3-butenyl; alkynyl, in particular $C_2$-$C_6$ alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantly, decahydro-naphthalenyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuranyl, tetrahydrothienyl, tetrahydrothienyl, piperazinyl, decahydro-quinolinyl, decahydro-isoquinolinyl, decahydro-quinoxalinyl, decahydro-quinazolinyl; alkoxy, in particular $C_1$-$C_6$ alkoxy, e.g. $C_1$, $C_2$, $C_3$, $C_4$, $C_5$, or $C_6$ alkoxy, preferably methoxy, ethoxy, propoxy, iso-propoxy, butoxy, iso-butoxy, tert-butoxy, pentoxy, or hexoxy; aryl, in particular phenyl, naphthalenyl or anthracenyl; aralkyl; preferably $C_1$-$C_6$ aralkyl, e.g. $C_1$, $C_2$, $C_3$, $C_4$, $C_5$, or $C_6$ aralkyl; heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; and —NR⁶R⁷;

A is selected from the group consisting of alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_1$-$C_6$ alkenyl, e.g. $C_1$, $C_2$, $C_3$, $C_4$, $C_5$, or $C_6$ alkenyl, preferably methenyl, ethenyl, 1-propenyl, 2-propenyl, 1-iso-propenyl, 2-iso-propenyl, 1-butenyl, 2-butenyl, 3-butenyl; alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantly, decahydro-naphthalenyl; alkoxy, in particular $C_1$-$C_6$ alkoxy, e.g. $C_1$, $C_2$, $C_3$, $C_4$, $C_5$, or $C_6$ alkoxy, preferably methoxy, ethoxy, propoxy, iso-propoxy, butoxy, iso-butoxy, tert-butoxy, pentoxy, or hexoxy; alkoxyalkyl, in particular $C_1$-$C_6$-alkoxy-$C_1$-$C_6$-alkyl, e.g. methoxymethyl, ethoxymethyl, propoxymethyl, methoxyethyl, ethoxyethyl, propoxyethyl, methoxypropyl, ethoxypropyl, or propoxypropyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuranyl, tetrahydrothienyl, tetrahydrothienyl, piperazinyl, decahydroquinolinyl, decahydro-isoquinolinyl, decahydro-quinoxalinyl, decahydro-quinazolinyl; an alicyclic system, which may comprise one or more heteroatoms, e.g. 1, 2, 3, or 4, preferably selected from the group consisting of O, S, or N; in particular 1,2-dihydropyridinyl, 1,2,5,6-tetrahydropyridinyl, 1,2,3,4-tetrahydropyridyl, 1,2-dihydropyrazyl, 1,2,3,4-tetrahydropyrazyl, cyclopropenyl, cyclobutenyl, cyclopentenyl, cyclohexenyl, cycloheptenyl; aryl, in particular phenyl, naphthalenyl or anthracenyl; and heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; optionally substituted;

q is an integer from 0 to 4, i.e. 0, 1, 2, 3, or 4, preferably 1;
X is selected from O or S; preferably O;
Y is selected from O or NH or S; preferably O.

In a preferred method of the present invention the potential agonist or potential antagonist structurally related to noscapine has a structure according to formula (VIII)

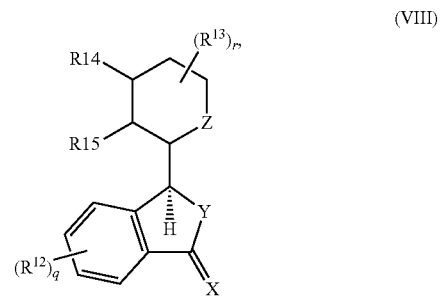

(VIII)

wherein
$R^{12}$ is in each instance independently selected from the group consisting of halogen, —NO₂, —CN, —OR⁶, —NR⁶R⁷, —COOR⁶, —CONR⁶R⁷, —NR⁸COR⁹, —NR⁸COR⁹, —NR⁸CONR⁶R⁷, —NR⁹SO₂A, —COR^E, —SO₂NR⁶R⁷, —OOCR⁸, —CR⁸R⁹OH, R⁸OH, and -A or two substituents on adjacent carbon atoms form together with a oxygen atom an epoxy group or a cycloalkyl, cycloheteroalkyl, alicyclic system, aryl or heteroaryl, optionally substituted;
$R^{13}$ is in each instance independently selected from the group consisting of halogen, —NO₂, —CN, —OR⁶, —NR⁶R⁷, —COOR⁶, —CONR⁶R⁷, —NR⁸COR⁹, —NR⁸COR⁹, —NR⁸CONR⁶R⁷, —NR⁹SO₂A, —COR^E, —SO₂NR⁶R⁷, —OOCR⁸, —CR⁸R⁹OH, R⁸OH, and -A or two substituents on adjacent carbon atoms form together an alicyclic system, aryl or heteroaryl, optionally substituted;
$R^{14}$ and $R^{15}$ together form a cycloalkyl, preferably $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, bicyclo[5.3.0]decyl, octahydro-pentalenyl, octahydro-indenyl, decahydro-azulenyl, adamantly, or decahydro-naphthalenyl; heterocycloalkyl, preferably $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{1-4}$-heterocycloalkyl, in particular piperidinyl, morpholinyl, 1,3-diazacyclohexane, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuran-3-yl, tetrahydrothien-2-yl, tetrahydrothien-3-yl, piperazinyl, decahydroquinolinyl, decahydro-isoquinolinyl, decahydro-quinoxalinyl, or decahydro-quinazolinyl; an alicyclic system, preferably $C_3$-$C_{14}$-alicyclic system, e.g. $C_3$, $C_4$, $C_5$, $C_6$, $C_7$, $C_8$, $C_9$, $C_{10}$, $C_{11}$, $C_{12}$, $C_{13}$ or $C_{14}$-alicyclic system, in particular cyclopropenyl, cyclobutenyl, cyclopentenyl, cyclohexenyl, cycloheptenyl, cyclooctyl, cyclononenyl, cyclodecenyl, spiro[3,3]heptenyl, spiro[3,4]octenyl, spiro[4,3]octenyl, spiro[3,5]nonenyl, spiro[5,3]nonenyl, spiro[3,6]decenyl, spiro[6,3]decenyl, spiro[4,5]decenyl, spiro[5,4]decenyl, bicyclo[4.1.0]heptenyl, or bicyclo[3.2.0]heptenyl, bicyclo[2.2.1]heptenyl, bicyclo[2.2.2]octenyl, bicyclo[5.1.0]octenyl, bicyclo[4.2.0]octenyl, bicyclo[5.3.0]decenyl, hexahydro-pentalenyl, hexahydro-indenyl, octahydro-azulenyl, or octahydronaphthalenyl, or a derivative thereof, wherein 1, 2 or 3 carbon atoms are replaced by a heteroatom each independently selected from the group consisting of nitrogen, sulphur, or oxygen; aryl, in particular phenyl, naphthalenyl or anthracenyl; or heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; preferably decahydro-naphthalenyl, cyclodecyl, octahydro-naphthalenyl, or cyclodecenyl; optionally substituted;

$R^6$ and $R^7$ is each independently selected from the group consisting of hydrogen; alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_2$-$C_6$ alkenyl, e.g. $C_2$, $C_3$, $C_4$, $C_5$, or $C_6$ alkenyl, preferably ethenyl, 1-propenyl, 2-propenyl, 1-iso-propenyl, 2-iso-propenyl, 1-butenyl, 2-butenyl, 3-butenyl; alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantly, decahydro-naphthalenyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuranyl, tetrahydrothienyl, tetrahydrothienyl, piperazinyl, decahydroquinolinyl, decahydro-isoquinolinyl, decahydro-quinoxalinyl, decahydro-quinazolinyl; aryl, in particular phenyl, naphthalenyl or anthracenyl; heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; and aralkyl, preferably $C_1$-$C_6$ aralkyl, e.g. $C_1$, $C_2$, $C_3$, $C_4$, $C_5$, or $C_6$ aralkyl; or together form a heteroaryl, in particular, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, indolyl, isoindolyl, 1H-indazolyl, benzimidazolyl, indoxazinyl, 2,1-benzisoxazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; optionally substituted;

$R^8$ and $R^9$ is each independently selected from the group consisting of hydrogen; alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_2$-$C_6$ alkenyl, e.g. $C_2$, $C_3$, $C_4$, $C_5$, or $C_6$ alkenyl, preferably ethenyl, 1-propenyl, 2-propenyl, 1-iso-propenyl, 2-iso-propenyl, 1-butenyl, 2-butenyl, 3-butenyl; alkynyl, in particular $C_2$-$C_6$ alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantly, decahydro-naphthalenyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuranyl, tetrahydrothienyl, tetrahydrothienyl, piperazinyl, decahydro-quinolinyl, decahydro-isoquinolinyl, decahydro-quinoxalinyl, decahydro-quinazolinyl; alkoxy, in particular $C_1$-$C_6$ alkoxy, e.g. $C_1$, $C_2$, $C_3$, $C_4$, $C_5$, or $C_6$ alkoxy, preferably methoxy, ethoxy, propoxy, iso-propoxy, butoxy, iso-butoxy, tert-butoxy, pentoxy, or hexoxy; aryl, in particular phenyl, naphthalenyl or anthracenyl; aralkyl; preferably $C_1$-$C_6$ aralkyl, e.g. $C_1$, $C_2$, $C_3$, $C_4$, $C_5$, or $C_6$ aralkyl; heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; and —$NR^6R^7$;

A is selected from the group consisting of alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_1$-$C_6$ alkenyl, e.g. $C_1$, $C_2$, $C_3$, $C_4$, $C_5$, or $C_6$ alkenyl, preferably methenyl, ethenyl, 1-propenyl, 2-propenyl, 1-iso-propenyl, 2-iso-propenyl, 1-butenyl, 2-butenyl, 3-butenyl; alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantly, decahydro-naphthalenyl; alkoxy, in particular $C_1$-$C_6$ alkoxy, e.g. $C_1$, $C_2$, $C_3$, $C_4$, $C_5$, or $C_6$ alkoxy, preferably methoxy, ethoxy, propoxy, iso-propoxy, butoxy, iso-butoxy, tert-butoxy, pentoxy, or hexoxy; alkoxyalkyl, in particular $C_1$-$C_6$-alkoxy-$C_1$-$C_6$-alkyl, e.g. methoxymethyl, ethoxymethyl, propoxymethyl, methoxyethyl, ethoxyethyl, propoxyethyl, methoxypropyl, ethoxypropyl, or propoxypropyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7, 11-dioxo-spiro[5,5]undecyl, 1,4-diazabicyclo[2.2.2]oct-2-yl, tetrahydrofuran-2-yl, tetrahydrofuranyl, tetrahydrothienyl, tetrahydrothienyl, piperazinyl, decahydroquinolinyl, decahydro-isoquinolinyl, decahydro-quinoxalinyl, decahydro-quinazolinyl; an alicyclic system, which may comprise one or more heteroatoms, e.g. 1, 2, 3, or 4, preferably selected from the group consisting of O, S, or N; in particular 1,2-dihydropyridinyl, 1,2,5,6-tetrahydropyridinyl, 1,2,3,4-tetrahydropyridyl, 1,2-dihydropyrazyl, 1,2,3,4-tetrahydropyrazyl, cyclopropenyl, cyclobutenyl, cyclopentenyl, cyclohexenyl, cycloheptenyl; aryl, in particular phenyl, naphthalenyl or anthracenyl; and heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; optionally substituted;

q is an integer from 0 to 4, i.e. 0, 1, 2, 3, or 4, preferably 1;

r is an integer from 0 to 7, i.e. 0, 1, 2, 3, 4, 5, 6, or 7, preferably 1

X is selected from O or S; preferably O;

Y is selected from O or NH or S; preferably O; and

Z. is selected from O or NR' or S; preferably NR', wherein R' is H or alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, or hexyl.

In a further preferred embodiment of either method of the present invention the potential agonist or potential antagonist that is employed in the identification process is structurally related to amarogentin and has a structure according to formula (IX)

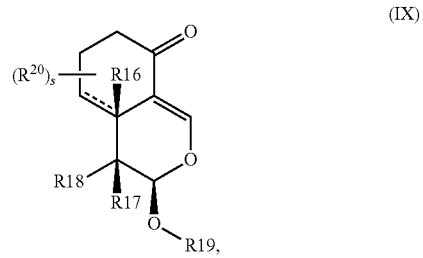

wherein $R^{16}$ is H; OH; halogen, in particular F, Cl, Br or I; alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_2$-$C_6$ alkenyl, e.g. $C_2$, $C_3$, $C_4$, $C_5$, or $C_6$ alkenyl, preferably ethenyl, 1-propenyl, 2-propenyl, 1-iso-propenyl, 2-iso-propenyl, 1-butenyl, 2-butenyl, 3-butenyl; alkoxy, in particular $C_1$-$C_6$ alkoxy, e.g. $C_1$, $C_2$, $C_3$, $C_4$, $C_5$, or $C_6$ alkoxy, preferably methoxy, ethoxy, propoxy, iso-propoxy, butoxy, iso-butoxy, tert-butoxy, pentoxy, hexoxy; alkoxyalkyl, in particular $C_1$-$C_6$-alkoxy-$C_1$-$C_6$-alkyl, e.g. methoxymethyl, ethoxymethyl, propoxymethyl, methoxyethyl, ethoxyethyl, propoxyethyl, methoxypropyl, ethoxypropyl, or propoxypropyl; optionally substituted or is not present, if the dashed line is a bond;

$R^{17}$ is in each instance independently selected from the group consisting of H, OH, halogen, —$NO_2$, —CN, —$OR^6$, —$NR^6R^7$, —$COOR^6$, —$CONR^6R^7$, —$NR^8COR^9$, —$NR^8COR^9$, —$NR^8CONR^6R^7$, —$NR^9SO_2A$, —$COR^E$, —$SO_2NR^6R^7$, —$OOCR^8$, —$CR^8R^9OH$, $R^8OH$, and -A;

$R^{18}$ is H; OH; halogen, in particular F, Cl, Br or I; alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_2$-$C_6$ alkenyl, e.g. $C_2$, $C_3$, $C_4$, $C_5$, or $C_6$ alkenyl, preferably ethenyl, 1-propenyl, 2-propenyl, 1-iso-propenyl, 2-iso-propenyl, 1-butenyl, 2-butenyl, 3-butenyl; alkoxy, in particular $C_1$-$C_6$ alkoxy, e.g. $C_1$, $C_2$, $C_3$, $C_4$, $C_5$, or $C_6$ alkoxy, preferably methoxy, ethoxy, propoxy, iso-propoxy, butoxy, iso-butoxy, tert-butoxy, pentoxy, hexoxy; alkoxyalkyl, in particular $C_1$-$C_6$-alkoxy-$C_1$-$C_6$-alkyl, e.g. methoxymethyl, ethoxymethyl, propoxymethyl, methoxyethyl, ethoxyethyl, propoxyethyl, methoxypropyl, ethoxypropyl, or propoxypropyl; optionally substituted $R^{19}$ sugar moiety, in particular mono or disaccharide, preferably fructose, glucose, galactose, saccharose, ribose, desoxyribose, most preferably glucose; optionally substituted;

$R^{20}$ is in each instance independently selected from the group consisting of halogen, —$NO_2$, —CN, —$OR^6$, —$NR^6R^7$, —$COOR^6$, —$CONR^6R^7$, —$NR^8COR^9$, —$NR^8COR^9$, —$NR^8CONR^6R^7$, —$NR^9SO_2A$, —$COR^E$, —$SO_2NR^6R^7$, —$OOCR^8$, —$CR^8R^9OH$, $R^8OH$, and -A or two substituents on adjacent carbon atoms form together with a oxygen atom an epoxy group or a cycloalkyl, cycloheteroalkyl, alicyclic system, aryl or heteroaryl, optionally substituted;

$R^6$ and $R^7$ is each independently selected from the group consisting of hydrogen, alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_2$-$C_6$ alkenyl, e.g. $C_2$, $C_3$, $C_4$, $C_5$, or $C_6$ alkenyl, preferably ethenyl, 1-propenyl, 2-propenyl, 1-iso-propenyl, 2-iso-propenyl, 1-butenyl, 2-butenyl, 3-butenyl; alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantly, decahydro-naphthalenyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro-[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuranyl, tetrahydrothienyl, tetrahydrothienyl, piperazinyl, decahydroquinolinyl, decahydro-isoquinolinyl, decahydro-quinoxalinyl, decahydro-quinazolinyl; aryl, in particular phenyl, naphthalenyl or anthracenyl; heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; and aralkyl, preferably $C_1$-$C_6$ aralkyl, e.g. $C_1$, $C_2$, $C_3$, $C_4$, $C_5$, or $C_6$ aralkyl; or together form a heteroaryl, in particular, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, indolyl, isoindolyl, 1H-indazolyl, benzimidazolyl, indoxazinyl, 2,1-benzisoxazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; optionally substituted;

$R^8$ and $R^9$ is each independently selected from the group consisting of hydrogen; alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_2$-$C_6$ alkenyl, e.g. $C_2$, $C_3$, $C_4$, $C_5$, or $C_6$ alkenyl, preferably ethenyl, 1-propenyl, 2-propenyl, 1-iso-propenyl, 2-iso-propenyl, 1-butenyl, 2-butenyl, 3-butenyl; alkynyl, in particular $C_2$-$C_6$ alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantly, decahydro-naphthalenyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro-[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuranyl, tetrahydrothienyl, tetrahydrothienyl, piperazinyl, decahydro-quinolinyl, decahydro-isoquinolinyl, decahydro-quinoxalinyl, decahydro-quinazolinyl; alkoxy, in particular $C_1$-$C_6$ alkoxy, e.g. $C_1$, $C_2$, $C_3$, $C_4$, $C_5$, or $C_6$ alkoxy, preferably methoxy, ethoxy, propoxy, iso-propoxy, butoxy, iso-butoxy, tert-butoxy, pentoxy, or hexoxy; aryl, in particular phenyl, naphthalenyl or anthracenyl; aralkyl; preferably $C_1$-$C_6$ aralkyl, e.g. $C_1$, $C_2$, $C_3$, $C_4$, $C_5$, or $C_6$ aralkyl; heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; and —$NR^6R^7$;

A is selected from the group consisting of alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_1$-$C_6$ alkenyl, e.g. $C_1$, $C_2$, $C_3$, $C_4$, $C_5$, or $C_6$ alkenyl, preferably methenyl, ethenyl, 1-propenyl, 2-propenyl, 1-iso-propenyl, 2-iso-propenyl, 1-butenyl, 2-butenyl, 3-butenyl; alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantly, decahydro-naphthalenyl; alkoxy, in particular $C_1$-$C_6$ alkoxy, e.g. $C_1$, $C_2$, $C_3$, $C_4$, $C_5$, or $C_6$ alkoxy, preferably methoxy, ethoxy, propoxy, iso-propoxy, butoxy, iso-butoxy, tert-butoxy, pentoxy, or hexoxy; alkoxyalkyl, in particular $C_1$-$C_6$-alkoxy-$C_1$-$C_6$-alkyl, e.g. methoxymethyl, ethoxymethyl, propoxymethyl, methoxyethyl, ethoxyethyl, propoxyethyl, methoxypropyl, ethoxypropyl, or propoxypropyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuranyl, tetrahydrothienyl, tetrahydrothienyl, piperazinyl, decahydroquinolinyl, decahydro-isoquinolinyl, decahydro-quinoxalinyl, decahydro-quinazolinyl; an alicyclic system, which may comprise one or more heteroatoms, e.g. 1, 2, 3, or 4, preferably selected from the group consisting of O, S, or N; in particular 1,2-dihydropyridinyl, 1,2,5,6-tetrahydropyridinyl, 1,2,3,4-tetrahydropyridyl, 1,2-dihydropyrazyl, 1,2,3,4-tetrahydropyrazyl, cyclopropenyl, cyclobutenyl, cyclopentenyl, cyclohexenyl, cycloheptenyl; aryl, in particular phenyl, naphthalenyl or anthracenyl; and heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_1$-$C_6$ alkenyl, e.g. $C_1$, $C_2$, $C_3$, $C_4$, $C_5$, or $C_6$ alkenyl, preferably methenyl, ethenyl, 1-propenyl, 2-propenyl, 1-iso-propenyl, 2-iso-propenyl, 1-butenyl, 2-butenyl, 3-butenyl; more preferably methyl; optionally substituted; and s is an integer from 0 to 3, i.e. 0, 1, 2, or 3, preferably 1.

In a more preferred embodiment the potential agonist or potential antagonist structurally related to amarogentin and has a structure according to formula (X)

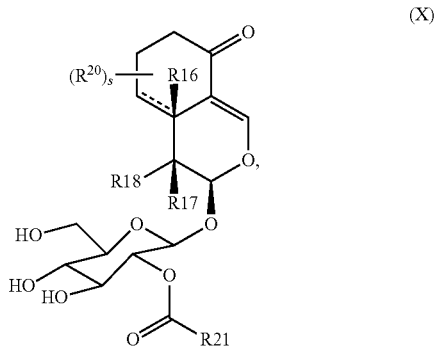

(X)

wherein $R^{16}$, $R^{17}$, $R^{18}$, $R^{20}$, and s have the meanings and preferred meanings outlined above and $R^{21}$ is selected from the group consisting of alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_1$-$C_6$ alkenyl, e.g. $C_1$, $C_2$, $C_3$, $C_4$, $C_5$, or $C_6$ alkenyl, preferably methenyl, ethenyl, 1-propenyl, 2-propenyl, 1-iso-propenyl, 2-iso-propenyl, 1-butenyl, 2-butenyl, 3-butenyl; alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantly, decahydro-naphthalenyl; alkoxyalkyl, in particular $C_1$-$C_6$-alkoxy-$C_1$-$C_6$-alkyl, e.g. methoxymethyl, ethoxymethyl, propoxymethyl, methoxyethyl, ethoxyethyl, propoxyethyl, methoxypropyl, ethoxypropyl, or propoxypropyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diaza-cyclohexane, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuranyl, tetrahydrothienyl, tetrahydrothienyl, piperazinyl, decahydroquinolinyl, decahydro-isoquinolinyl, decahydro-quinoxalinyl, decahydro-quinazolinyl; an alicyclic system, which may comprise one or more heteroatoms, e.g. 1, 2, 3, or 4, preferably selected from the group consisting of O, S, or N; in particular 1,2-dihydropyridinyl, 1,2,5,6-tetrahydropyridinyl, 1,2,3,4-tetrahydropyridyl, 1,2-dihydropyrazyl, 1,2,3,4-tetrahydropyrazyl, cyclopropenyl, cyclobutenyl, cyclopentenyl, cyclohexenyl, cycloheptenyl; aryl, in particular phenyl, naphthalenyl or anthracenyl; and heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; preferably alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_1$-$C_6$ alkenyl, e.g. $C_1$, $C_2$, $C_3$, $C_4$, $C_5$, or $C_6$ alkenyl, preferably methenyl, ethenyl, 1-propenyl, 2-propenyl, 1-iso-propenyl, 2-iso-propenyl, 1-butenyl, 2-butenyl, 3-butenyl; more preferably methenyl; optionally substituted 1, 2, 3, 4 or 5 times. In the most preferred embodiment $R^{21}$ is phenyl, optionally substituted.

In a further preferred embodiment of either method of the present invention the potential agonist or potential antagonist that is employed in the identification process is structurally related to humulon and has a structure according to formula (XI)

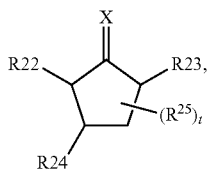

(XI)

wherein

R²² is H, OH, halogen, in particular F, Br, or Cl; alkyl, in particular $C_1$-$C_{10}$ alkyl, e.g. $C_1$, $C_2$, $C_3$, $C_4$, $C_5$, $C_6$ $C_7$, $C_8$, $C_9$ or $C_{10}$ alkyl, preferably methyl, ethyl, propyl, iso-propyl, butyl, iso-butyl, tert-butyl, pentyl, hexyl; alkenyl, in particular $C_1$-$C_{10}$ alkenyl, e.g. $C_1$, $C_2$, $C_3$, $C_4$, $C_5$, $C_6$ $C_7$, $C_8$, $C_9$ or $C_{10}$ alkenyl, preferably methenyl, ethenyl, 1-propenyl, 2-propenyl, 1-iso-propenyl, 2-iso-propenyl, 1-butenyl, 2-butenyl, 3-butenyl; 3-methyl-but-2-enyl 4-methyl-pent-3-enyl; alkoxy, in particular $C_1$-$C_6$ alkoxy, e.g. $C_1$, $C_2$, $C_3$, $C_4$, $C_5$, or $C_6$ alkoxy, preferably methoxy, ethoxy, propoxy, iso-propoxy, butoxy, iso-butoxy, tert-butoxy, pentoxy, or hexoxy; alkoxyalkyl, in particular $C_1$-$C_6$ alkoxy-$C_1$-$C_6$ alkyl, e.g. methoxymethyl, ethoxymethyl, propoxymethyl, methoxyethyl, ethoxyethyl, propoxyethyl, methoxypropyl, ethoxypropyl, or propoxypropyl; preferably $C_1$-$C_6$ alkyl, more preferably methyl; cycloalkyl, in particular $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, bicyclo[5.3.0]decyl, octahydro-pentalenyl, octahydro-indenyl, decahydro-azulenyl, adamantly, or decahydro-naphthalenyl; heterocycloalkyl, preferably $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuran-3-yl, tetrahydrothien-2-yl, tetrahydrothien-3-yl, piperazinyl, decahydroquinolinyl, decahydro-isoquinolinyl, decahydro-quinoxalinyl, or decahydroquinazolinyl; an alicyclic system, preferably $C_3$-$C_{14}$-alicyclic system, e.g. $C_3$, $C_4$, $C_5$, $C_6$, $C_7$, $C_8$, $C_9$, $C_{10}$, $C_{11}$, $C_{12}$, $C_{13}$ or $C_{14}$-alicyclic system, in particular cyclopropenyl, cyclobutenyl, cyclopentenyl, cyclohexenyl, cycloheptenyl, cyclooctenyl, cyclononenyl, cyclodecenyl, spiro[3,3]heptenyl, spiro[3,4]octenyl, spiro[4,3]octenyl, spiro[3,5]nonenyl, spiro[5,3]nonenyl, spiro[3,6]decenyl, spiro[6,3]decenyl, spiro[4,5]decenyl, spiro[5,4]decenyl, bicyclo[4.1.0]heptenyl, bicyclo[3.2.0]heptenyl, bicyclo[2.2.1]heptenyl, bicyclo[2.2.2]octenyl, bicyclo[5.1.0]octenyl, bicyclo[4.2.0]octenyl, bicyclo[5.3.0]decenyl, hexahydro-pentalenyl, hexahydro-indenyl, octahydro-azulenyl, or octahydro-naphthalenyl, or a derivative thereof, wherein 1, 2 or 3 carbon atoms are replaced by a heteroatom each independently selected from the group consisting of nitrogen, sulphur, or oxygen; aryl, in particular phenyl, naphthalenyl or anthracenyl; or heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; preferably decahydro-naphthalenyl, cyclodecyl, octahydro-naphthalenyl, or cyclodecenyl; optionally substituted;

R²³ is H, OH, halogen, in particular F, Br, or Cl; alkyl, in particular $C_1$-$C_{10}$ alkyl, e.g. $C_1$, $C_2$, $C_3$, $C_4$, $C_5$, $C_6$ $C_7$, $C_8$, $C_9$ or $C_{10}$ alkyl, preferably methyl, ethyl, propyl, iso-propyl, butyl, iso-butyl, tert-butyl, pentyl, hexyl; alkenyl, in particular $C_1$-$C_{10}$ alkenyl, e.g. $C_1$, $C_2$, $C_3$, $C_4$, $C_5$, $C_6$ $C_7$, $C_8$, $C_9$ or $C_{10}$ alkenyl, preferably methenyl, ethenyl, 1-propenyl, 2-propenyl, 1-iso-propenyl, 2-iso-propenyl, 1-butenyl, 2-butenyl, 3-butenyl; 3-methyl-but-2-enyl 4-methyl-pent-3-enyl; optionally substituted, preferably with an oxo-group;

R²⁴ is H, OH, halogen, in particular F, Br, or Cl; alkyl, in particular $C_1$-$C_{10}$ alkyl, e.g. $C_1$, $C_2$, $C_3$, $C_4$, $C_5$, $C_6$ $C_7$, $C_8$, $C_9$ or $C_{10}$ alkyl, preferably methyl, ethyl, propyl, iso-propyl, butyl, iso-butyl, tert-butyl, pentyl, hexyl; alkenyl, in particular $C_1$-$C_{10}$ alkenyl, e.g. $C_1$, $C_2$, $C_3$, $C_4$, $C_5$, $C_6$ $C_7$, $C_8$, $C_9$ or $C_{10}$ alkenyl, preferably methenyl, ethenyl, 1-propenyl, 2-propenyl, 1-iso-propenyl, 2-iso-propenyl, 1-butenyl, 2-butenyl, 3-butenyl; 3-methyl-but-2-enyl 4-methyl-pent-3-enyl; alkoxy, in particular $C_1$-$C_6$ alkoxy, e.g. $C_1$, $C_2$, $C_3$, $C_4$, $C_5$, or $C_6$ alkoxy, preferably methoxy, ethoxy, propoxy, iso-propoxy, butoxy, iso-butoxy, tert-butoxy, pentoxy, or hexoxy; alkoxyalkyl, in particular $C_1$-$C_6$ alkoxy-$C_1$-$C_6$ alkyl, e.g. methoxymethyl, ethoxymethyl, propoxymethyl, methoxyethyl, ethoxyethyl, propoxyethyl, methoxypropyl, ethoxypropyl, or propoxypropyl; preferably $C_1$-$C_6$ alkyl, more preferably methyl; cycloalkyl, in particular $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, bicyclo[5.3.0]decyl, octahydro-pentalenyl, octahydro-indenyl, decahydro-azulenyl, adamantly, or decahydro-naphthalenyl; heterocycloalkyl, preferably $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuran-3-yl, tetrahydrothien-2-yl, tetrahydrothien-3-yl, piperazinyl, decahydroquinolinyl, decahydro-isoquinolinyl, decahydro-quinoxalinyl, or decahydroquinazolinyl; an alicyclic system, preferably $C_3$-$C_{14}$- alicyclic system, e.g. $C_3$, $C_4$, $C_5$, $C_6$, $C_7$, $C_8$, $C_9$, $C_{10}$, $C_{11}$, $C_{12}$, $C_{13}$ or $C_{14}$-alicyclic system, in particular cyclopropenyl, cyclobutenyl, cyclopentenyl, cyclohexenyl, cycloheptenyl, cyclooctyl, cyclononenyl, cyclodecenyl, spiro[3,3]heptenyl, spiro[3,4]octenyl, spiro[4,3]octenyl, spiro[3,5]nonenyl, spiro[5,3]nonenyl, spiro[3,6]decenyl, spiro[6,3]decenyl, spiro[4,5]decenyl, spiro[5,4]decenyl, bicyclo[4.1.0]heptenyl, bicyclo[3.2.0]heptenyl, bicyclo[2.2.1]heptenyl, bicyclo[2.2.2]octenyl, bicyclo[5.1.0]octenyl, bicyclo[4.2.0]octenyl, bicyclo[5.3.0]decenyl, hexahydro-pentalenyl, hexahydro-indenyl, octahydro-azulenyl, or octahydro-naphthalenyl, or a derivative thereof, wherein 1, 2 or 3 carbon atoms are replaced by a heteroatom each independently selected from the group consisting of nitrogen, sulphur, or oxygen; aryl, in particular phenyl, naphthalenyl or anthracenyl; or heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; preferably decahydro-naphthalenyl, cyclodecyl, octahydro-naphthalenyl, or cyclodecenyl; optionally substituted;

$R^{25}$ is in each instance independently selected from the group consisting of halogen, —$NO_2$, —CN, —$OR^6$, —$NR^6R^7$, —$COOR^6$, —$CONR^6R^7$, —$NR^8COR^9$, —$NR^8COR^9$, —$NR^8CONR^6R^7$, —$NR^9SO_2A$, —$COR^E$, —$SO_2NR^6R^7$, —$OOCR^8$, —$CR^8R^9OH$, $R^8OH$, and -A or two substituents on adjacent carbon atoms form together with a oxygen atom an epoxy group or a cycloalkyl, cycloheteroalkyl, alicyclic system, aryl or heteroaryl, optionally substituted;

$R^6$ and $R^7$ is each independently selected from the group consisting of hydrogen, alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_2$-$C_6$ alkenyl, e.g. $C_2$, $C_3$, $C_4$, $C_5$, or $C_6$ alkenyl, preferably ethenyl, 1-propenyl, 2-propenyl, 1-iso-propenyl, 2-iso-propenyl, 1-butenyl, 2-butenyl, 3-butenyl; alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantly, decahydro-naphthalenyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuranyl, tetrahydrothienyl, tetrahydrothienyl, piperazinyl, decahydroquinolinyl, decahydro-isoquinolinyl, decahydro-quinoxalinyl, decahydro-quinazolinyl; aryl, in particular phenyl, naphthalenyl or anthracenyl; heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; and aralkyl, preferably $C_1$-$C_6$ aralkyl, e.g. $C_1$, $C_2$, $C_3$, $C_4$, $C_5$, or $C_6$ aralkyl; or together form a heteroaryl, in particular, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, indolyl, isoindolyl, 1H-indazolyl, benzimidazolyl, indoxazinyl, 2,1-benzisoxazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; optionally substituted;

$R^8$ and $R^9$ is each independently selected from the group consisting of hydrogen; alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_2$-$C_6$ alkenyl, e.g. $C_2$, $C_3$, $C_4$, $C_5$, or $C_6$ alkenyl, preferably ethenyl, 1-propenyl, 2-propenyl, 1-iso-propenyl, 2-iso-propenyl, 1-butenyl, 2-butenyl, 3-butenyl; alkynyl, in particular $C_2$-$C_6$ alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantly, decahydro-naphthalenyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuranyl, tetrahydrothienyl, tetrahydrothienyl, piperazinyl, decahydro-quinolinyl, decahydro-isoquinolinyl, decahydro-quinoxalinyl, decahydro-quinazolinyl; alkoxy, in particular $C_1$-$C_6$ alkoxy, e.g. $C_1$, $C_2$, $C_3$, $C_4$, $C_5$, or $C_6$ alkoxy, preferably methoxy, ethoxy, propoxy, iso-propoxy, butoxy, iso-butoxy, tert-butoxy, pentoxy, or hexoxy; aryl, in particular phenyl, naphthalenyl or anthracenyl; aralkyl; preferably $C_1$-$C_6$ aralkyl, e.g. $C_1$, $C_2$, $C_3$, $C_4$, $C_5$, or $C_6$ aralkyl; heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; and —$NR^6R^7$;

A is selected from the group consisting of alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_1$-$C_6$ alkenyl, e.g. $C_1$, $C_2$, $C_3$, $C_4$, $C_5$, or $C_6$ alkenyl, preferably methenyl, ethenyl, 1-propenyl, 2-propenyl, 1-iso-propenyl, 2-iso-propenyl, 1-butenyl, 2-butenyl, 3-butenyl; alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_2$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantly, decahydro-naphthalenyl; alkoxy, in particular $C_1$-$C_6$ alkoxy, e.g. $C_1$, $C_2$, $C_3$, $C_4$, $C_5$, or $C_6$ alkoxy, preferably methoxy, ethoxy, propoxy, iso-propoxy, butoxy, iso-butoxy, tert-butoxy, pentoxy, or hexoxy; alkoxyalkyl, in particular $C_1$-$C_6$-alkoxy-$C_1$-$C_6$-alkyl, e.g. methoxymethyl, ethoxymethyl, propoxymethyl, methoxyethyl, ethoxyethyl, propoxyethyl, methoxypropyl, ethoxypropyl, or propoxypropyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuranyl, tetrahydrothienyl, tetrahydrothienyl, piperazinyl, decahydroquinolinyl, decahydro-isoquinolinyl, decahydro-quinoxalinyl, decahydro-quinazolinyl; an alicyclic system, which may comprise one or more heteroatoms, e.g. 1, 2, 3, or 4, preferably selected from the group consisting of O, S, or N; in particular 1,2-dihydropyridinyl, 1,2,5,6-tetrahydropyridinyl, 1,2,3,4-tetrahydropyridyl, 1,2-dihydropyrazyl, 1,2,3,4-tetrahydropyrazyl, cyclopropenyl, cyclobutenyl, cyclopentenyl, cyclohexenyl, cycloheptenyl; aryl, in particular phenyl, naphthalenyl or anthracenyl; and heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; optionally substituted;

t is an integer from 0 to 5, i.e. 0, 1, 2, 3, 4 or 5, preferably 1; and

X is selected from O or S; preferably O.

In a further preferred embodiment of either method of the present invention the potential agonist or potential antagonist is structurally related to humulon and has a structure according to formula (XII)

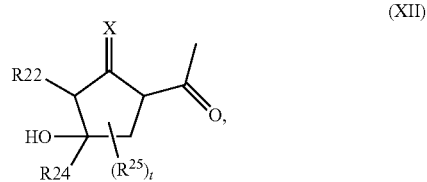

(XII)

wherein $R^{22}$, $R^{24}$ and $R^{25}$ have their above indicated meaning and preferred meanings and t is an integer from 0 to 4, i.e. 0, 1, 2, 3, or 4, preferably 1; and X is selected from O or S; preferably O.

In a further preferred embodiment of either method of the present invention the potential agonist or potential antagonist is structurally related to N,N'-diethylurea and has a structure according to formula (XIII)

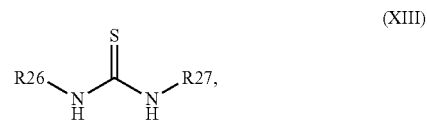

(XIII)

wherein $R^{26}$ is selected from the group consisting of alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_1$-$C_6$ alkenyl, e.g. $C_1$, $C_2$, $C_3$, $C_4$, $C_5$, or $C_6$ alkenyl, preferably methenyl, ethenyl, 1-propenyl, 2-propenyl, 1-iso-propenyl, 2-iso-propenyl, 1-butenyl, 2-butenyl, 3-butenyl; alkynyl, in particular $C_2$-$C_6$ alkynyl, e.g. $C_2$, $C_3$, $C_4$, $C_5$, or $C_6$ alkynyl; cycloalkyl, e.g. $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantly, decahydro-naphthalenyl, 2-methylene-decahydro-naphthalenyl, or 2-methylene-decahydro-naphthalen-1-yl; alkoxy, in particular $C_1$-$C_6$ alkoxy, e.g. $C_1$, $C_2$, $C_3$, $C_4$, $C_5$, or $C_6$ alkoxy, preferably methoxy, ethoxy, propoxy, iso-propoxy, butoxy, iso-butoxy, tert-butoxy, pentoxy, or hexoxy; alkoxyalkyl, in particular $C_1$-$C_6$ alkoxy-$C_1$-$C_6$ alkyl, e.g. methoxymethyl, ethoxymethyl, propoxymethyl, methoxyethyl, ethoxyethyl, propoxyethyl, methoxypropyl, ethoxypropyl, or propoxypropyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexanyl, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuran-3-yl, tetrahydrothien-2-yl, tetrahydrothien-3-yl, piperazinyl, decahydroquinolinyl, decahydro-isoquinolinyl, decahydro-quinoxalinyl, or decahydro-quinazolinyl; an alicyclic system, which may comprise one or more heteroatoms preferably selected from the group consisting of O, S, or N; in particular 1,2-dihydropyridinyl, 1,2,5,6-tetrahydropyridinyl, 1,2,3,4-tetrahydropyridyl, 1,2-dihydropyrazyl, 1,2,3,4-tetrahydropyrazyl, cyclopropenyl, cyclobutenyl, cyclopentenyl, cyclohexenyl, cycloheptenyl; aryl, in particular phenyl, naphthalenyl or anthracenyl; or heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; optionally substituted;

$R^{27}$ is selected from the group consisting of alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_1$-$C_6$ alkenyl, e.g. $C_1$, $C_2$, $C_3$, $C_4$, $C_5$, or $C_6$ alkenyl, preferably methenyl, ethenyl, 1-propenyl, 2-propenyl, 1-iso-propenyl, 2-iso-propenyl, 1-butenyl, 2-butenyl, 3-butenyl; alkynyl, in particular $C_2$-$C_6$ alkynyl, e.g. $C_2$, $C_3$, $C_4$, $C_5$, or $C_6$ alkynyl; cycloalkyl, e.g. $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydropentalenyl, octahydro-indenyl, decahydro-azulenyl, adamantly, decahydro-naphthalenyl, 2-methylene-decahydro-naphthalenyl, or 2-methylene-decahydro-naphthalen-1-yl; alkoxy, in particular $C_1$-$C_6$ alkoxy, e.g. $C_1$, $C_2$, $C_3$, $C_4$, $C_5$, or $C_6$ alkoxy, preferably methoxy, ethoxy, propoxy, iso-propoxy, butoxy, iso-butoxy, tert-butoxy, pentoxy, or hexoxy; alkoxyalkyl, in particular $C_1$-$C_6$ alkoxy-$C_1$-$C_6$ alkyl, e.g. methoxymethyl, ethoxymethyl, propoxymethyl, methoxyethyl, ethoxyethyl, propoxyethyl, methoxypropyl, ethoxypropyl, or propoxypropyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexanyl, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuran-3-yl, tetrahydrothien-2-yl, tetrahydrothien-3-yl, piperazinyl, decahydroquinolinyl, decahydro-isoquinolinyl, decahydro-quinoxalinyl, or decahydro-quinazolinyl; an alicyclic system, which may comprise one or more heteroatoms preferably selected from the group consisting of O, S, or N; in particular 1,2-dihydropyridinyl, 1,2,5,6-tetrahydropyridinyl, 1,2,3,4-tetrahydropyridyl, 1,2-dihydropyrazyl, 1,2,3,4-tetrahydropyrazyl, cyclopropenyl, cyclobutenyl, cyclopentenyl, cyclohexenyl, cycloheptenyl; aryl, in particular phenyl, naphthalenyl or anthracenyl; or heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; optionally substituted or $R^{26}$ and $R^{27}$ together form a heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular, imidazolidinyl, 1,3-diazacyclohexanyl, 1,3-diazacycloheptanyl, or decahydro-quinazolinyl; an alicyclic system comprising two nitrogen atoms indicated in formula (I) and which may comprise one or more further heteroatoms preferably selected from the group consisting of O, S, or N; in particular dihydro-imidazolyl, e.g. 1,2-dihydro-imidazolyl, dihydro-pyrimidinyl, e.g. 4,5, dihydro-pyrimidinyl, 1,2-dihydropyrimidinyl, 2,3-dihydro-1H-benzoimidazolyl, 2,3-dihydro-1H-imidazo[4,5-c]pyridinyl, 2,3-dihydro-1H-imidazo[4,5-d]pyridinyl, or 6,7-dihydro-5H-imidazo[4,5-c]pyridazinyl; or heteroaryl, in particular imidazolyl, 1,2,4-triazolyl, pyrimidinyl, 1,2,4-triazinyl, 1,3,5-triazinyl, benzimidazolyl, quinazolinyl, 1,2,4-benzotriazinyl, 3H-imidazo[4,5-b]pyridinyl, 3H-imidazo[4,5-c]pyridinyl, 1H-imidazo[4,5-b]pyrazinyl, 7H-purine, or 7H-Imidazo[4,5-c]pyridazinyl; optionally substituted.

In a further preferred embodiment of either method of the present invention the potential agonist or potential antagonist structurally related to azathioprine, azepinon, benzoin, brucine, camphor, cascarillin, chlorhexidine, herbolid A, papaverin, picrotoxinin, or (−)-a-thujon are based on the known structure of this compounds (see FIG. 1) and are derived by introducing and/or exchanging one or more, preferably two, three or four substituents. Preferably, the introduction or exchange of one or two substituents in each instance independently selected from the group consisting of halogen, in particular F, Cl, Br or I; —$NO_2$; —CN; —$OR^c$; —$NR^cR^d$; —CO-$OR^c$; —$CONR^cR^d$; —$NR^aCOR^b$; —$NR^aCOR^b$; —$NR^aCONR^cR^d$; —$NR^bSO_2D$; —$COR^c$, —$SO_2NR^cR^d$; —$OOCR^a$; —$CR^aR^bOH$; $R^aOH$; and -D;

$R^a$ and $R^b$ is each independently selected from the group consisting of hydrogen; alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_2$-$C_6$ alkenyl, e.g. $C_2$, $C_3$, $C_4$, $C_5$, or $C_6$ alkenyl, preferably ethenyl, 1-propenyl, 2-propenyl, 1-iso-propenyl, 2-iso-propenyl, 1-butenyl, 2-butenyl, 3-butenyl; alkynyl, in particular $C_2$-$C_6$ alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantly, decahydro-naphthalenyl; heterocycloalkyl, e.g. $C_3$-$C_{14}$— heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuranyl, tetrahydrothienyl, tetrahydrothienyl, piperazinyl, decahydro-quinolinyl, decahydro-isoquinolinyl, decahydro-quinoxalinyl, decahydro-quinazolinyl; alkoxy, in particular $C_1$-$C_6$ alkoxy, e.g. $C_1$, $C_2$, $C_3$, $C_4$, $C_5$, or $C_6$ alkoxy, preferably methoxy, ethoxy, propoxy, iso-propoxy, butoxy, iso-butoxy, tert-butoxy, pentoxy, or hexoxy; aryl, in particular phenyl, naphthalenyl or anthracenyl; aralkyl; preferably $C_1$-$C_6$ aralkyl, e.g. $C_1$, $C_2$, $C_3$, $C_4$, $C_5$, or $C_6$ aralkyl; heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; and -NR$^e$R$^e$;

R$^c$ and R$^d$ is each independently selected from the group consisting of hydrogen, alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_2$-$C_6$ alkenyl, e.g. $C_2$, $C_3$, $C_4$, $C_5$, or $C_6$ alkenyl, preferably ethenyl, 1-propenyl, 2-propenyl, 1-iso-propenyl, 2-iso-propenyl, 1-butenyl, 2-butenyl, 3-butenyl; alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantly, decahydro-naphthalenyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuranyl, tetrahydrothienyl, tetrahydrothienyl, piperazinyl, decahydroquinolinyl, decahydro-isoquinolinyl, decahydro-quinoxalinyl, decahydro-quinazolinyl; aryl, in particular phenyl, naphthalenyl or anthracenyl; heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; and aralkyl, preferably $C_1$-$C_6$ aralkyl, e.g. $C_1$, $C_2$, $C_3$, $C_4$, $C_5$, or $C_6$ aralkyl; or together form a heteroaryl, in particular, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, indolyl, isoindolyl, 1H-indazolyl, benzimidazolyl, indoxazinyl, 2,1-benzisoxazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; optionally substituted; and D is selected from the group consisting of alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_1$-$C_6$ alkenyl, e.g. $C_1$, $C_2$, $C_3$, $C_4$, $C_5$, or $C_6$ alkenyl, preferably methenyl, ethenyl, 1-propenyl, 2-propenyl, 1-iso-propenyl, 2-iso-propenyl, 1-butenyl, 2-butenyl, 3-butenyl; alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_2$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantly, decahydro-naphthalenyl; alkoxy, in particular $C_1$-$C_6$ alkoxy, e.g. $C_1$, $C_2$, $C_3$, $C_4$, $C_5$, or $C_6$ alkoxy, preferably methoxy, ethoxy, propoxy, iso-propoxy, butoxy, iso-butoxy, tert-butoxy, pentoxy, or hexoxy; alkoxyalkyl, in particular $C_1$-$C_6$-alkoxy-$C_1$-$C_6$-alkyl, e.g. methoxymethyl, ethoxymethyl, propoxymethyl, methoxyethyl, ethoxyethyl, propoxyethyl, methoxypropyl, ethoxypropyl, or propoxypropyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct- 2-yl, tetrahydrofuran-2-yl, tetrahydrofuranyl, tetrahydrothienyl, tetrahydrothienyl, piperazinyl, decahydroquinolinyl, decahydro-isoquinolinyl, decahydro-quinoxalinyl, decahydro-quinazolinyl; an alicyclic system, which may comprise one or more heteroatoms, e.g. 1, 2, 3, or 4, preferably selected from the group consisting of O, S, or N; in particular 1,2-dihydropyridinyl, 1,2,5,6-tetrahydropyridinyl, 1,2,3,4-tetrahydropyridyl, 1,2-dihydropyrazyl, 1,2,3,4-tetrahydropyrazyl, cyclopropenyl, cyclobutenyl, cyclopentenyl, cyclohexenyl, cycloheptenyl; aryl, in particular phenyl, naphthalenyl or anthracenyl; and heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; optionally substituted.

The potential agonists or potential antagonists, which are employed in the methods of the present invention can be synthesized by methods and standard procedures known to those skilled in the art, i.e. as described in the literature (for example in the standard works, such as Houben-Weyl, Methoden der organischen Chemie [Methods of Organic Chemistry], Georg-Thieme-Verlag, Stuttgart), under reaction conditions which are known to those skilled in the art and suitable for the said reactions.

The selected, e.g. isolated, antagonist or agonist is in a preferred embodiment chemical modified in a further step. Again this chemical modification can be effected by a variety of methods known in the art, which include without limitation the introduction of one or more, preferably two, three or four substituents or the exchange of one or more substituents. Preferably, the introduction or exchange of one or two substituents in each instance independently selected from the group consisting of halogen, in particular F, Cl, Br or I; $NO_2$; —CN; —$OR^c$; —$NR^cR^d$; —$COOR^c$; —$CONR^cR^d$; —$NR^aCOR^b$; —$NR^aCOR^b$; —$NR^aCONR^cR^d$; —$NR^bSO_2D$; —$COR^c$—$SO_2NR^cR^d$; —$OOCR^a$; —$CR^aR^b$OH; $R^aOH$; and -D;

$R^a$ and $R^b$ is each independently selected from the group consisting of hydrogen; alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_2$-$C_6$ alkenyl, e.g. $C_2$, $C_3$, $C_4$, $C_5$, or $C_6$ alkenyl, preferably ethenyl, 1-propenyl, 2-propenyl, 1-iso-propenyl, 2-iso-propenyl, 1-butenyl, 2-butenyl, 3-butenyl; alkynyl, in particular $C_2$-$C_6$ alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantly, decahydro-naphthalenyl; heterocycloalkyl, e.g. $C_3$-$C_{14}$— heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuranyl, tetrahydrothienyl, tetrahydrothienyl, piperazinyl, decahydro-quinolinyl, decahydro-isoquinolinyl, decahydro-quinoxalinyl, decahydro-quinazolinyl; alkoxy, in particular $C_1$-$C_6$ alkoxy, e.g. $C_1$, $C_2$, $C_3$, $C_4$, $C_5$, or $C_6$ alkoxy, preferably methoxy, ethoxy, propoxy, isopropoxy, butoxy, iso-butoxy, tert-butoxy, pentoxy, or hexoxy; aryl, in particular phenyl, naphthalenyl or anthracenyl; aralkyl; preferably $C_1$-$C_6$ aralkyl, e.g. $C_1$, $C_2$, $C_3$, $C_4$, $C_5$, or $C_6$ aralkyl; heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; and —$NR^cR^c$;

$R^c$ and $R^d$ is each independently selected from the group consisting of hydrogen, alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_2$-$C_6$ alkenyl, e.g. $C_2$, $C_3$, $C_4$, $C_5$, or $C_6$ alkenyl, preferably ethenyl, 1-propenyl, 2-propenyl, 1-iso-propenyl, 2-iso-propenyl, 1-butenyl, 2-butenyl, 3-butenyl; alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantly, decahydro-naphthalenyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuranyl, tetrahydrothienyl, tetrahydrothienyl, piperazinyl, decahydroquinolinyl, decahydro-isoquinolinyl, decahydro-quinoxalinyl, decahydro-quinazolinyl; aryl, in particular phenyl, naphthalenyl or anthracenyl; heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; and aralkyl, preferably $C_1$-$C_6$ aralkyl, e.g. $C_1$, $C_2$, $C_3$, $C_4$, $C_5$, or $C_6$ aralkyl; or together form a heteroaryl, in particular, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, indolyl, isoindolyl, 1H-indazolyl, benzimidazolyl, indoxazinyl, 2,1-benzisoxazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; optionally substituted; and D is selected from the group consisting of alkyl, in particular $C_1$-$C_6$ alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; alkenyl, in particular $C_1$-$C_6$ alkenyl, e.g. $C_1$, $C_2$, $C_3$, $C_4$, $C_5$, or $C_6$ alkenyl, preferably methenyl, ethenyl, 1-propenyl, 2-propenyl, 1-iso-propenyl, 2-iso-propenyl, 1-butenyl, 2-butenyl, 3-butenyl; alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_2$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantly, decahydro-naphthalenyl; alkoxy, in particular $C_1$-$C_6$ alkoxy, e.g. $C_1$, $C_2$, $C_3$, $C_4$, $C_5$, or $C_6$ alkoxy, preferably methoxy, ethoxy, propoxy, iso-propoxy, butoxy, iso-butoxy, tert-butoxy, pentoxy, or hexoxy; alkoxyalkyl, in particular $C_1$-$C_6$-alkoxy-$C_1$-$C_6$-alkyl, e.g. methoxymethyl, ethoxymethyl, propoxymethyl, methoxyethyl, ethoxyethyl, propoxyethyl, methoxypropyl, ethoxypropyl, or propoxypropyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7, 11-dioxo-spiro[5,5]undecyl, 1,4-diazabicyclo[2.2.2]oct-2-yl, tetrahydrofuran-2-yl, tetrahydrofuranyl, tetrahydrothienyl, tetrahydrothienyl, piperazinyl, decahydroquinolinyl, decahydro-isoquinolinyl, decahydro-quinoxalinyl, decahydro-quinazolinyl; an alicyclic system, which may comprise one or more heteroatoms, e.g. 1, 2, 3, or 4, preferably selected from the group consisting of O, S, or N; in particular 1,2-dihydropyridinyl, 1,2,5,6-tetrahydropyridinyl, 1,2,3,4-tetrahydropyridyl, 1,2-dihydropyrazyl, 1,2,3,4-tetrahydropyrazyl, cyclopropenyl, cyclobutenyl, cyclopentenyl, cyclohexenyl, cycloheptenyl; aryl, in particular phenyl, naphthalenyl or anthracenyl; and heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; optionally substituted.

The thus modified antagonist is then tested with the first embodiment of the method of the present invention. The modified antagonist is contacted with the hTAS2R$^{14}$, hTAS2R$^{10}$ or hTAS2R$^{4}$ polypeptide as such or with the polypeptide expressed in a host cell, which has been contacted prior, concomitantly or after step (1) with absinthin, artemorin, amarogentin, arglabin, azathioprine, azepinon, benzoin, brucine, camphor, cascarillin, chlorhexidine, N,N'-diethylthiourea, herbolid A, isohumulone, noscapine, papaverin, parthenolid, picrotoxinin, arborescin or (−)-a-thujon or an agonistic compound structurally related to absinthin, artemorin, amarogentin, arglabin, azathioprine, azepinon, benzoin, brucine, camphor, cascarillin, chlorhexidine, N,N'-diethylthiourea, herbolid A, isohumulone, noscapine, papaverin, parthenolid, picrotoxinin, arborescin or (−)-a-thujon and subsequently inhibition of the bitter taste receptor activity by the modified antagonist is measured. The activation and, thus, also the inhibition of activation of the hTAS2R14, hTAS2R10 or hTAS2R4 protein can be measured, e.g. by the intracellular calcium release mediated. If needed the steps of selecting the antagonist, modifying the compound, contacting the antagonist with a polypeptide or a host cell and measuring of the activation of the bitter taste receptor activity can be repeated a further or any given number of times as required. The above described method is also termed "directed evolution" of an antagonist since it involves a multitude of steps including modification and selection, whereby antagonizing compounds are selected in an "evolutionary" process optimizing their capabilities with respect to a particular property, e.g. their ability to inhibit or modulate the activity of hTAS2R14, hTAS2R10 or hTAS2R4, in particular inhibit or stimulate the intracellular release of calcium. Preferably, a modified antagonist is selected that reduces the activity of hTAS2R14, hTAS2R10 or hTAS2R4 stimulated by absinthin, artemorin, arglabin, azathioprine, azepinon, benzoin, brucine, camphor, chlorhexidine, N,N'-diethylthiourea, herbolid A, isohumulone, noscapine, parthenolid, or arborsecin for hTAS2R14; absinthin, artemorin, amarogentin, arglabin, azathioprine, benzoin, camphor, cascarillin, papaverin, parthenolid, picrotoxinin, arborescin or (−)-a-thujon for hTAS2R10; or artemorin, amarogentin, azathioprine or campor for hTAS2R4 at least as good as the identified antagonist used as basis for the modified antagonist at the same molar concentration. More preferably, the modified antagonist shows a stronger reduction at the same molar concentration, preferably at least a 10% stronger reduction, 20%, 30%, 40%, 50%, 60, or 70% stronger reduction.

The above stated process of directed evolution also can be applied to optimize the capability of an isolated agonist. This method comprises the modification of the identified agonist as indicated above and testing the activating activity of this modified agonist in a method according to the second aspect of this invention. Optionally, further rounds of chemical modification are carried out. Preferably, a modified agonist is selected that increases the activity of hTAS2R14, hTAS2R10 or hTAS2R4 at least as good as the identified agonist at the same molar concentration. More preferably, the modified antagonist shows a stronger activation at the same molar concentration, preferably at least a 10% stronger activation, 20%, 30%, 40%, 50%, 60, 70%, 100%, 200%, 1000% stronger activation.

In a preferred embodiment, compounds structurally related to absinthin, artemorin, amarogentin, arglabin, azathioprine, azepinon, benzoin, brucine, camphor, cascarillin, chlorhexidine, N,N'-diethylthiourea, herbolid A, isohumulone, noscapine, papaverin, parthenolid, picrotoxinin, arborescin or (−)-a-thujon are used in the first round of above stated directed evolution methods.

The term "structurally related agonist" refers to agonists, which are derived from absinthin, artemorin, amarogentin, arglabin, azathioprine, azepinon, benzoin, brucine, camphor, cascarillin, chlorhexidine, N,N'-diethylthiourea, herbolid A, isohumulone, noscapine, papaverin, parthenolid, picrotoxinin, arborescin and (−)-a-thujon, respectively, by chemical modification and which elicit at least 20% (e.g., at least: 20%; 30%; 40%; 50%; 60%; 70%; 80%; 90%; 95%; 98%; 99%; 99.5%; or 100%, 150%, 200%, 300%, 500%, 1,000%, 10,000% or more) of the bitter taste receptor activity, if compared to the respective unmodified agonist at the same molar concentration. Preferably, the assay system used is the cellular assay system described in more detail in the Examples. Preferred structurally related agonists have a structure as described above under formulas (I) to (XIII).

The term "structurally related antagonist" of absinthin, artemorin, amarogentin, arglabin, azathioprine, azepinon, benzoin, brucine, camphor, cascarillin, chlorhexidine, N,N'-diethylthiourea, herbolid A, isohumulone, noscapine, papaverin, parthenolid, picrotoxinin, arborescin and (−)-a-thujon, respectively, is a substance, which is derived from absinthin, artemorin, amarogentin, arglabin, azathioprine, azepinon, benzoin, brucine, camphor, cascarillin, chlorhexidine, N,N'-diethylthiourea, herbolid A, isohumulone, noscapine, papaverin, parthenolid, picrotoxinin, arborescin and (−)-a-thujon by chemical modification and which lowers the hTAS2R14, hTAS2R10 and hTAS2R4 bitter taste receptor activity, respectively, determined in the presence of absinthin, artemorin, amarogentin, arglabin, azathioprine, azepinon, benzoin, brucine, camphor, cascarillin, chlorhexidine, N,N'-diethylthiourea, herbolid A, isohumulone, noscapine, papaverin, parthenolid, picrotoxinin, arborescin and (−)-a-thujon, respectively, by at least 10% (e.g. at least 10%, 15%, 20%, 30%, 40%, 50%, 60%, 70%, 80%, 90%, 95%, 98%, 99%, 99,5% or 100%) Preferably, the antagonistic derivative exerts this action, when it is contacted prior, concomitantly or after, preferably concomitantly, to the contacting of the hTAS2R14, hTAS2R10 and hTAS2R4 polypeptide, respectively, the host cell expressing the hTAS2R14, hTAS2R10 and hTAS2R4 polypeptide, respectively, or the vector comprising the hTAS2R14, hTAS2R10 and hTAS2R4 polypeptide, respectively, with the agonist. Preferred structurally related antagonists have a structure as described above under formulas (I) to (XIII).

In order to express cDNAs encoding the receptors, one typically subclones receptor cDNA into an expression vector that contains a strong promoter to direct transcription, a transcription/translation terminator, and a ribosome-binding site for translational initiation. Suitable bacterial promoters are well known in the art, e.g., *E. coli, Bacillus* sp., and *Salmonella*, and kits for such expression systems are commercially available. Similarly eukaryotic expression systems for mammalian cells, yeast, and insect cells are well known in the art and are also commercially available. The eukaryotic expression vector may be, for example an adenoviral vector, an adeno-associated vector, or a retroviral vector.

In addition to the promoter, the expression vector typically contains a transcription unit or expression cassette that contains all the additional elements required for the expression of the receptor-encoding nucleic acid in host cells. A typical expression cassette thus contains a promoter operatively linked to the nucleic acid sequence encoding the receptor and signals required for efficient polyadenylation of the transcript, ribosome binding sites, and translation termination. The nucleic acid sequence encoding the receptor may typically be linked to a membrane-targeting signal such as the N-terminal 45 amino acids of the rat somatostatin receptor 3 sequence to promote efficient cell-surface expression of the recombinant receptor. Additional elements of the cassette may include, for example enhancers.

An expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ, but there are many more known in the art to the skilled person that can be usefully employed.

Expression vectors containing regulatory elements from eukaryotic viruses are typically used in eukaryotic expression vectors, e.g. SV40 vectors, papilloma virus vectors, and vectors derived from Epstein-Barr virus. Other exemplary eukaryotic vectors include pMSG, pAV009/A.sup.+, pMT010/A.sup.+, pMAMneo-5, baculovirus pDSVE, pcDNA3.1, pIRES and any other vector allowing expression of proteins under the direction of the SV40 early promoter, SV40 late promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable.

The elements that are typically included in expression vectors also include a replicon that functions in *E. coli*, a gene encoding drug resistance to permit selection of bacteria that harbor recombinant plasmids, and unique restriction sites in nonessential regions of the plasmid to allow insertion of eukaryotic sequences. The particular drug resistance gene chosen is not critical, any of the many drug resistance genes known in the art are suitable. The prokaryotic sequences are optionally chosen such that they do not interfere with the replication of the DNA in eukaryotic cells, if necessary.

Standard transfection methods can be used to produce bacterial, mammalian, yeast or insect cell lines that express large quantities of the receptor, which are then purified using standard techniques. Any of the well-known procedures for introducing foreign polynucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell. It is only necessary that the particular genetic engineering procedure used be capable of successfully introducing at least one gene into the host cell capable of expressing the receptor.

After the expression vector is introduced into the cells, the transfected cells may be cultured under conditions favouring expression of the receptor, which is recovered from the culture using standard techniques. For example the cells may be burst open either mechanically or by osmotic shock before being subject to precipitation and chromatography steps, the nature and sequence of which will depend on the particular recombinant material to be recovered. Alternatively, the recombinant protein may be recovered from the culture medium in which the recombinant cells had been cultured.

The activity of the receptor described herein can be assessed using a variety of in vitro and in vivo assays to determine functional, chemical, and physical effects, e.g., measuring ligand binding, secondary messengers (e.g., cAMP, cGMP, IP$_3$, DAG, or Ca$^{2+}$) ion flux, phosphorylation levels, transcription levels, of reporter constructs neurotransmitter levels, and the like. Such assays are used in the method of the present invention to test for the activity of the receptors.

Samples or assays that are treated with a potential receptor agonist or antagonist may be compared to control samples which are untreated (agonist control) or which are untreated or have been treated with an agonist (antagonist control), to examine the extent of modulation. Control samples are assigned a relative receptor activity value of 100. Inhibition of receptor activity is achieved when the receptor activity value relative to the control is lower, and conversely receptor activity is enhanced when activity relative to the control is higher in the presence of identical amounts of the respective agonist or antagonist, respectively.

The effects of the test compounds upon the function of the receptors can be measured by examining any of the parameters described above. Any suitable physiological change that affects receptor activity can be used to assess the influence of a test compound on the receptors usable in the methods of this invention. When the functional consequences are determined using intact cells or animals, these consequences can be measured by any means known to those skilled in the art, e.g., patch clamping, voltage-sensitive dyes, whole cell currents, radioisotope efflux, inducible markers, oocyte bitter taste receptor gene expression; tissue culture cell bitter taste receptor expression; transcriptional activation of bitter taste receptor genes; ligand binding assays; voltage, membrane potential and conductance changes; ion, preferably sodium or calcium ion flux assays, for example measuring calcium levels using calcium sensitive dyes such as Fluo-3, Fluo-4 or Fura-2; changes in intracellular second messengers such as cAMP, cGMP, and inositol triphosphate (IP$_3$); changes in intracellular calcium levels; neurotransmitter release, and the like. These assays may be performed on intact cells expressing a bitter taste receptor polypeptide, on permeabilized cells, or on membrane fractions produced by standard methods.

Preferred assays for G-protein coupled receptors include cells that are loaded with ion sensitive dyes to report receptor activity. In assays for identifying modulatory compounds, changes in the level of ions in the cytoplasm or membrane voltage will be monitored using an ion sensitive or membrane voltage fluorescent indicator, respectively. For G-protein coupled receptors, promiscuous G-proteins such as G$\alpha$15 and G$\alpha$i6 and chimeric G-proteins can be used in the assay of choice (see, for example, Wilkie et al. (1991) Proc. Nat. Acad. Sci. USA 88: 10049-10053). Such promiscuous G-proteins allow coupling of a wide range of receptors to G-protein dependent signal pathways.

Receptor activation typically initiates subsequent intracellular events, e.g. increases in second messengers such as IP$_3$, which releases intracellular stores of calcium ions. Activation of some G-protein coupled receptors stimulates the formation of inositol trisphosphate through phospholipase C-mediated hydrolysis of phosphatidylinositol bisphosphate (Berridge & Irvine (1984) Nature 312: 315-21). IP$_3$ in turn stimulates the release of intracellular calcium ion stores. Thus, a change in cytoplasmic calcium ion levels, or a change in second messenger levels such as IP$_3$ can be used to assess G-protein coupled receptor function. Cells expressing such G-protein coupled receptors may exhibit increased cytoplasmic calcium levels as a result of contribution from both intracellular stores and via activation of ion channels, in which case it may be desirable, although not necessary, to conduct such assays in calcium-free buffer, optionally supplemented with a chelating agent such as EGTA, to distinguish fluorescence response resulting from calcium release from internal stores.

In a preferred embodiment, receptor activity is measured by expressing the hTAS2R14, hTAS2R10 or hTAS2R4 bitter taste receptors in a heterologous cell with a G-protein, such as G$\alpha$15, G$\alpha$16, transducin, gustducin, or a chimeric G-protein that links the receptor to a phospholipase C signal transduction pathway. In another aspect of the invention, only the extracellular domain of the respective bitter taste receptor is expressed as a chimeric transmembrane fusion protein. A preferred cell line is HEK-293, although other mammalian cell lines are also preferred such as CHO and COS cells. Modulation of taste transduction is assayed by measuring changes in intracellular Ca$^{2+}$ levels, which change in response to modulation of the receptor signal transduction pathway via administration of a molecule that associates with the receptor. Changes in Ca$^{2+}$ levels are optionally measured using fluorescent Ca$^{2+}$ indicator dyes and fluorometric imaging. The activity of the signalling molecule and the increase or decrease of that activity in response to the potential agonist or antagonist can be determined as outlined above with respect to the identification of bitter taste receptor taste activity. The respectively indicated percent increases or decreases of the activity, which are required to qualify as antagonist or agonist do apply mutatis mutandis. Additionally the term "contacting" has the meaning as outlined above. Preferably the signalling molecule and/or the promiscuous G-protein has been introduced into the cell. The types of cell lines, which are preferred are those indicated above.

In yet another embodiment, the ligand-binding domains of the receptors can be employed in vitro in soluble or solid-state reactions to assay for ligand binding. Ligand binding to a bitter taste receptor, or a domain of a bitter taste receptor, such as e.g. the extracellular domain, can be tested in solution, in a bilayer membrane attached to a solid phase, in a lipid monolayer or vesicles. Thereby, the binding of a modulator to the receptor, or domain, can be observed using changes in spectroscopic characteristics, e.g. fluorescence, fluorescence polarization, plasmon resonance, absorbance or refractive index; or hydrodynamic (e.g. shape), chromatographic, or solubility properties, as is generally known in the art.

The compounds tested as modulators, i.e. potential agonists and antagonists, of the receptors can be any small chemical compound, or a biological entity, such as a protein, sugar, nucleic acid or lipid. Typically, test compounds will be small chemical molecules. Essentially any chemical compound can be used as a potential modulator or ligand in the assays of the invention, although knowledge of the ligand specificity of an individual receptor would enable the skilled person to make an intelligent selection of interesting compounds. The assays may be designed to screen large chemical libraries by automating the assay steps and providing compounds from any convenient source to assays, which are typically run in parallel (e.g., in microtiter formats on microtiter plates in robotic assays). The skilled person will understand that there are many suppliers of libraries of chemical compounds.

Assays may be run in high throughput screening methods that involve providing a combinatorial chemical or peptide library containing a large number of potential therapeutic, or tastant compounds (that are potential ligand compounds). Such libraries are then screened in one or more assays, as described herein, to identify those library members (particular chemical species or subclasses) that display a desired characteristic activity. The compounds thus identified can serve as lead compounds to further develop modulators for final products, or can themselves be used as actual modulators. A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art and no more needs to be stated here.

In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100 to about 1500 different compounds. It is possible to assay several different plates per day; assay screens for up to about 6,000-20,000 different compounds is possible using the integrated systems of the invention.

Antagonists identified by method described herein above, or development compounds formed from such antagonists can be administered directly to a human subject to modulate, e.g. inhibit, bitter taste. Alternatively, such compounds can be formulated with other ingredients of preparations to be taken orally, for example, foods, including animal food, and beverages, pharmaceutical or nutraceutical or homeopathic preparations.

Therefore, another aspect of the invention is a method for the production of food, a food precursor material or additive employed in the production of foodstuff comprising the step of admixing one or more of the above described isolated agonists, isolated antagonist, modified agonists, modified antagonists of hTAS2R14, hTAS2R10 and hTAS2R4 bitter taste receptor activity, respectively, with foodstuff or food precursor material or additive employed in the production of foodstuff.

Bitter taste is a particular problem when orally administering pharmaceuticals, which often have an unpleasant bitter taste. In particular in elderly persons, children and chronically ill patients this taste can lead to a lack of compliance with a treatment regimen. In addition in veterinary applications the oral administration of bitter tasting pharmaceuticals can be problematic. Therefore, a further aspect of the invention is a method for the production of a nutraceutical or pharmaceutical composition comprising the step of admixing the isolated antagonist or the modified antagonists of hTAS2R14, hTAS2R10 or hTAS2R4 bitter taste receptor activity with an active agent and optionally with a pharmaceutically acceptable carrier and/or adjuvants, in a pharmaceutically acceptable form.

Bitter tasting substances such as agonists of bitter taste receptors described herein are also useful supplements to serve as a safety additive in household (for example dissolvers, soaps, household chemicals) automotive and garden products. To prevent e.g. ingestion of such toxic substances, the amount of antagonist formulated with such products must be sufficient to effect an repellent response in the human or animal subject. Bitter tasting substances such as agonists of bitter taste receptors are also utilized to prevent nail-chewing and serve as repellent for animals including fish.

Therefore, another aspect of the invention is a method for the production of an animal repellent, precursor material or additive employed in the production of an animal repellent comprising the steps of admixing the isolated agonists, isolated antagonist, modified agonists or modified antagonists of hTAS2R14, hTAS2R10 and hTAS2R4 bitter taste receptor activity, respectively, as an active ingredient with an animal repellent or a precursor material or additive employed in the production of an animal repellent.

Consequently, a further aspect of the invention is an animal repellent, precursor material or additive employed in the production of an animal repellent producible as stated above.

A further aspect of the invention is food stuff, food precursor material or additive employed in the production of foodstuff producible according to the method of the invention.

Also comprised is a nutraceutical or pharmaceutical composition producible according to the method of the invention, comprising at least one nutraceutically or pharmaceutically active agent, an optional pharmaceutically acceptable carrier and/or adjuvants. These pharmaceutical and nutraceutical compositions comprise both products for human and animal consumption.

The amount of compound including an agonist or antagonist of present invention to be taken orally must be sufficient to effect a beneficial response in the subject, preferably human subject, and will be determined by the efficacy of the particular taste modulators and the existence, nature, and extent of any adverse side-effects that accompany the administration of a particular compound.

A further aspect of the present invention is the use of an agonist of hTAS2R14, hTAS2R10 or hTAS2R4 bitter taste receptor activity isolated according to the method of the invention to enhance bitter taste.

Also comprised is the use of an agonist of bitter taste receptor activity structurally related to absinthin, artemorin, amarogentin, arglabin, azathioprine, azepinon, benzoin, brucine, camphor, cascarillin, chlorhexidine, N,N'-diethylthiourea, herbolid A, isohumulone, noscapine, papaverin, parthenolid, picrotoxinin, arborescin or (−)-a-thujon, which may be identified by the methods taught herein, to enhance bitter taste, preferably of an agonist structurally related to absinthin, artemorin, amarogentin, arglabin, azathioprine, azepinon, benzoin, brucine, camphor, cascarillin, chlorhexidine, N,N'-diethylthiourea, herbolid A, isohumulone, noscapine, papaverin, parthenolid, picrotoxinin, arborescin or (−)-a-thujon having a structure according to formulas (I) to (XIII) as described above, to enhance bitter taste. In this use the bitter taste is preferably mediated by one or more bitter taste receptor selected from the group consisting of hTAS2R14, hTAS2R10 and hTAS2R4.

A further aspect of the present invention is the use of an antagonist of bitter taste receptor activity, which may be identified or produced by the methods taught herein, in particular an antagonist which is structurally related to absinthin, artemorin, amarogentin, arglabin, azathioprine, azepinon, benzoin, brucine, camphor, cascarillin, chlorhexidine, N,N'-diethylthiourea, herbolid A, isohumulone, noscapine, papaverin, parthenolid, picrotoxinin, arborescin and (−)-a-thujon, respectively, having a structure according to formulas (I) to (XIII) as described above, to reduce or suppress bitter taste. In this use the bitter taste is preferably mediated by bitter taste receptors selected from the group consisting of hTAS2R14, hTAS2R10 and hTAS2R4 is reduced or suppressed.

The following figures and examples are merely illustrative of the present invention and should not be construed to limit the scope of the invention as indicated by the appended claims in any way.

BRIEF DESCRIPTION OF THE TABLES AND FIGURES

FIG. 1 Chemical structure of artemorin (A), amarogentin (B), arglabin (C), absinthin (D), aborescin (E), noscapine (F), parthenolide (G), isohumulone (H), alpha-thujon (I), cascarillin (J), pictrotoxinin (K), papaverine (L), chlorhexidine (M), camphor (N), brucine (O), azathioprine (P), benzoin (O) and N,N' diethylthiourea (R).

Figure 2:
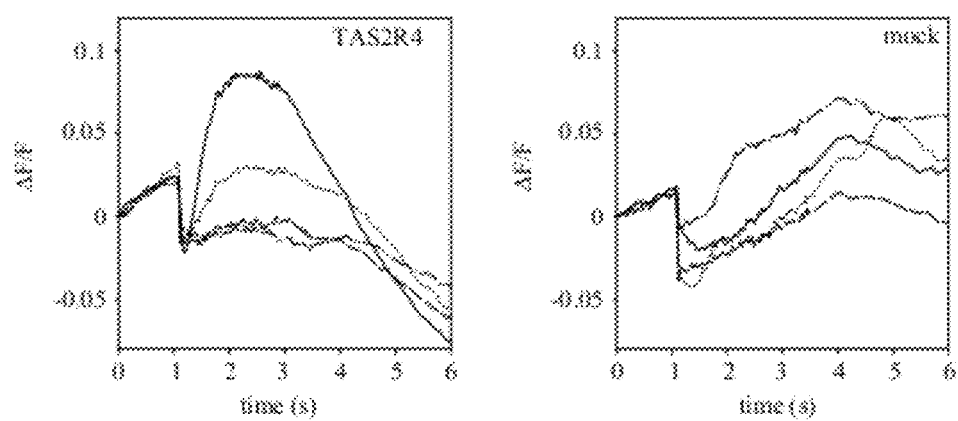

FIG. 2 Concentration-response curve of the effects of artemorin on the intracellular calcium concentration of HEK293T Gα16gust44 cells expressing TAS2R50. The data derived from one experiment carried out in triplicate.

Figure 3:
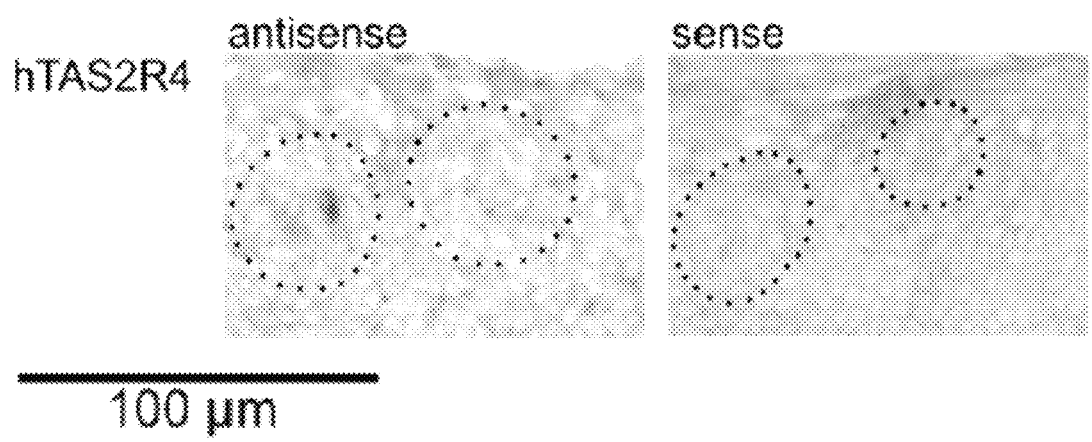

FIG. 3 Detection of hTAS2R4 mRNA in human circumvallate papilla by in situ hybridization.

EXAMPLES

Example 1

Functional Expression

Human TAS2R cDNA constructs were used that encoded a plasma membrane-targeting sequence of the rat somatostatin type 3 receptor at the N-terminus of the recombinant polypeptide and a herpes simplex virus glycoprotein D (HSV) epitope at its C-terminus (Bufe et al., 2002). The constructs were transiently transfected into HEK-293T cells that stably express the chimeric G-protein subunit Gα16gust44 using Lipofectamine 2000 (Invitrogen, San Diego, Calif.) in 96-well microtiter plates. Calcium imaging experiments using an automated fluorometric imaging plate reader (FLIPR) (Molecular Devices, Munich, Germany) have been performed 24-32 h later essentially as described previously (Bufe et al., 2002). Tastants (Sigma-Aldrich, Taufkirchen, Germany) were dissolved and administered in the following (in mM): 130 NaCl, 5 KCl, 10 HEPES, 2 $CaCl_2$, and 10 mM glucose, pH7.4. Data were collected from 1-2 independent experiments performed at least in triplicate and processed with SigmaPlot (SPSS, Chicago, Ill.). For dose-response curve calculation, the peak fluorescence responses after compound addition were corrected for and normalized to background fluorescence ($\Delta F/F=(F-F_0)/F_0$), and baseline noise was subtracted.

Example 2

In Situ Hybridization of Human Vallate Papilla

In situ hybridization was mainly done as before (Behrens et al, Eur J Neurosci 12 (2000) 1372-1384.). Briefly, 20 µm cross-sections of circumvallate papillae of human tongues were processed and thaw-mounted onto positively charged glass slides. Prior to hybridisation the sections were postfixated, permeabilised, and acetylated. Prehybridisation was done at 50° C. for 5 h, followed by hybridisation over night at 50° C. After hybridisation the slides were washed several times at low stringency, followed by RNAse A treatment and high stringency washes using 0.4×SSC buffer at 50° C. Hybridised riboprobes were detected using an anti-Digoxigenin antibody and colourimetry. Photomicrographs were taken with a CCD camera (RT slider, Diagnostic Instruments Inc.) mounted to a Zeiss Axioplan microscope.

Example 3

All 25 human bitter taste receptors were challenged with 100 µM artemorin (FIG. 1) in a FLIPR calcium imaging experiment. Out of these, three receptors, TAS2R14, TAS2R10, and TAS2R4, responded to artemorin in a dose-dependent manner (FIG. 2). Other tested substances elicited no calcium responses in TAS2R4-expressing cells (not shown). Only if these cells were challenged with high concentrations ($\geq 300$ µM) of denatonium benzoate and propylthiouracil (PROP), small responses could be detected, which is consistent with previously published results (Chandrashekar et al., Cell 2000). The signal obtained after stimulation with PROP is very small (somewhat questionable) and no dose-dependency can be shown as 1 mM PROP elicits endogenous signals of mock-transfected cells. Consistent with the role of TAS2R4 as a bitter taste receptor, we found its mRNA in taste receptor cells of human circumvallate papillae by in situ hybridisation (FIG. 3).

Example 4

In an assay similar to the assay described in Example 1 the three receptors, TAS2R14, TAS2R10, and TAS2R4, also responded to other bitter substances, when applied at the indicated molar ranges (see Table 1).

TABLE 1

| Substanz | TAS2R4 | TAS2R10 | TAS2R14 |
|---|---|---|---|
| Absinthin | | 0.3-0.01 mM | 0.1-0.0001 mM |
| Amarogentin | 1-0.3 mM | 1-0.1 mM | |
| Arglabin | | 0.1 mM | 0.1 mM |
| Azathioprine | 0.3-0.1 mM | 1-0.1 mM | 1-0.01 mM |
| Azepinon | | | 3-0.1 mM |
| Benzoin | | 0.1-0.01 mM | 0.1-0.003 mM |
| Brucine | | | 0.3-0.1 mM |
| Camphor | 1-0.1 mM | 1-0.03 mM | 0.1-0.003 mM |
| Cascarillin | | 0.1-0.003 mM | |
| Chlorhexidine | | | 0.001-0.000003 mM |
| N,N'-Diethylthiourea | | | 10 mM |
| Herbolid A | | | 1-0.001 mM |
| Isohumulone | | | 0.03-0.00003 mM |
| Noscapine | | | 0.01-0.0001 mM |
| Papaverin | | 0.01-0.0001 mM | |
| Parthenolid | | 0.3-001 mM | 1-0.001 mM |
| Picrotoxinin | | 3-0.3 mM | |
| Arborescin | | 0.3-0.1 mM | 0.3-0.01 mM |
| (−)-a-Thujon | | 0.3-0.03 mM | |

The invention claimed is:

1. A method for identifying an antagonist of hTAS2R14 bitter taste receptor activity,
wherein said hTAS2R14 bitter taste receptor activity is mediated by a hTAS2R14 bitter taste receptor comprising:
(a) a polypeptide comprising the amino acid sequence according to SEQ ID NO: 2; or
(b) a polypeptide comprising not more than fifteen (15) amino acid residues that are conservatively substituted compared to SEQ ID NO: 2 and has at least 20% hTAS2R14 bitter taste receptor activity; or
(c) a polypeptide having hTAS2R14 bitter taste receptor activity and where said polypeptide is at least 95% identical to a polypeptide having the amino acid sequence according to SEQ ID NO: 2;
comprising the steps:
(1) contacting a hTAS2R14 bitter taste receptor or a host cell expressing said hTAS2R14 bitter taste receptor with a potential antagonist, and
(2) determining whether the potential antagonist inhibits the hTAS2R14 bitter taste receptor activity;
wherein prior, concomitantly and/or after step (1) said bitter taste receptor or said host cell is contacted with chlorhexidine.

2. A method for identifying an agonist of hTAS2R14 bitter taste receptor activity,
wherein said hTAS2R14 bitter taste receptor activity is mediated by a hTAS2R14 bitter taste receptor comprising:
(a) a polypeptide comprising the amino acid sequence according to SEQ ID NO: 2; or
(b) a polypeptide comprising not more than fifteen (15) amino acid residues that are conservatively substituted compared to SEQ ID NO: 2 and has at least 20% hTAS2R14 bitter taste receptor activity; or
(c) a polypeptide having hTAS2R14 bitter taste receptor activity and where said polypeptide is at least 95% identical to a polypeptide having the amino acid sequence according to SEQ ID NO: 2;
comprising the steps:
(1) contacting a hTAS2R14 bitter taste receptor or a host cell expressing said hTAS2R14 bitter taste receptor with a potential agonist, and
(2) determining whether the potential agonist induces the hTAS2R14 bitter taste receptor activity;
wherein prior, concomitantly and/or after step (1) said bitter taste receptor or said host cell is contacted with chlorhexidine.

3. The method according to claim 2, wherein the identified potential agonist stimulates the activity of hTAS2R14 to at least 50% of the activity elicited by chlorhexidine at the same molar concentration.

4. The method according to claim 1, wherein the identified potential antagonist reduces the activity of hTAS2R14 stimulated by chlorhexidine at least by 10% at the same molar concentration.

5. A method for the production of a modified agonist of hTAS2R14, wherein an agonist identified in a method according to claim 2 is modified by the addition or exchange of at least one substituent.

6. The method according to claim 5, wherein a modified agonist is selected that stimulates the activity of hTAS2R14 at least as good as the identified agonist at the same molar concentration.

7. A method for the production of a modified antagonist of hTAS2R14, wherein an antagonist identified in a method according to claim 1 is modified by the addition or exchange of at least one substituent.

8. The method according to claim 7, wherein a modified antagonist is selected that reduces the activity of hTAS2R14 stimulated by chlorhexidine at least as good as the identified antagonist at the same molar concentration.

9. A method for the production of food, a food precursor material or additive employed in the production of foodstuff comprising the step of admixing the antagonist identified by the method of claim 1, and/or a modified antagonist thereof, with foodstuff, a food precursor material or additive employed in the production of foodstuff.

10. A method for the production of an animal repellent, precursor material or additive employed in the production of an animal repellent comprising the step of admixing the agonist identified according to the method of claim 2 and/or a modified agonist thereof, with an animal repellent or any precursor material or additive employed in the production of an animal repellent.

11. A method for the production of a nutraceutical or pharmaceutical composition comprising the step of admixing the antagonist identified by the method of claim 1, and/or a modified antagonist thereof, with an active agent and optionally with pharmaceutically acceptable carrier and/or adjuvants, in a pharmaceutically acceptable form.

* * * * *

SEQUENCE LISTING

<160> NUMBER OF SEQ ID NOS: 6

<210> SEQ ID NO 1
<211> LENGTH: 951
<212> TYPE: DNA
<213> ORGANISM: Homo sapiens

<400> SEQUENCE: 1

```
atgggtggtg tcataaagag catatttaca ttcgttttaa ttgtggaatt tataattgga      60
aatttaggaa atagtttcat agcactggtg aactgtattg actgggtcaa gggaagaaag     120
atctcttcgg ttgatcggat cctcactgct ttggcaatct ctcgaattag cctggtttgg     180
ttaatattcg gaagctggtg tgtgtctgtg tttttcccag cttttatttgc cactgaaaaa    240
atgttcagaa tgcttactaa tatctggaca gtgatcaatc attttagtgt ctggttagct     300
acaggcctcg gtactttta ttttctcaag atagccaatt tttctaactc tattttctc       360
tacctaaagt ggagagttaa aaaggtggtt ttggtgctgc ttcttgtgac ttcggtcttc     420
ttgttttaa atattgcact gataaacatc catataaatg ccagtatcaa tggatacaga      480
agaaacaaga cttgcagttc tgattcaagt aactttacac gattttccag tcttattgta     540
ttaaccagca ctgtgttcat tttcataccc tttactttgt ccctggcaat gtttcttctc     600
ctcatcttct ccatgtggaa acatcgcaag aagatgcagc acactgtcaa aatatccgga    660
gacgccagca ccaaagccca cagaggagtt aaaagtgtga tcactttctt cctactctat     720
gccatttct ctctgtcttt tttcatatca gtttggacct ctgaaaggtt ggaggaaaat     780
ctaattattc tttcccaggt gatgggaatg gcttatcctt catgtcactc atgtgttctg     840
attcttggaa acaagaagct gagacaggcc tctctgtcag tgctactgtg gctgaggtac     900
atgttcaaag atggggagcc ctcaggtcac aaagaattta gagaatcatc t              951
```

<210> SEQ ID NO 2
<211> LENGTH: 317
<212> TYPE: PRT
<213> ORGANISM: Homo sapiens

<400> SEQUENCE: 2

```
Met Gly Gly Val Ile Lys Ser Ile Phe Thr Phe Val Leu Ile Val Glu
1               5                   10                  15

Phe Ile Ile Gly Asn Leu Gly Asn Ser Phe Ile Ala Leu Val Asn Cys
            20                  25                  30

Ile Asp Trp Val Lys Gly Arg Lys Ile Ser Ser Val Asp Arg Ile Leu
        35                  40                  45

Thr Ala Leu Ala Ile Ser Arg Ile Ser Leu Val Trp Leu Ile Phe Gly
    50                  55                  60

Ser Trp Cys Val Ser Val Phe Phe Pro Ala Leu Phe Ala Thr Glu Lys
65                  70                  75                  80

Met Phe Arg Met Leu Thr Asn Ile Trp Thr Val Ile Asn His Phe Ser
                85                  90                  95

Val Trp Leu Ala Thr Gly Leu Gly Thr Phe Tyr Phe Leu Lys Ile Ala
            100                 105                 110

Asn Phe Ser Asn Ser Ile Phe Leu Tyr Leu Lys Trp Arg Val Lys Lys
        115                 120                 125

Val Val Leu Val Leu Leu Val Thr Ser Val Phe Leu Phe Leu Asn
    130                 135                 140

Ile Ala Leu Ile Asn Ile His Ile Asn Ala Ser Ile Asn Gly Tyr Arg
```

```
                145                 150                 155                 160
Arg Asn Lys Thr Cys Ser Ser Asp Ser Ser Asn Phe Thr Arg Phe Ser
                    165                 170                 175

Ser Leu Ile Val Leu Thr Ser Thr Val Phe Ile Phe Ile Pro Phe Thr
                180                 185                 190

Leu Ser Leu Ala Met Phe Leu Leu Ile Phe Ser Met Trp Lys His
            195                 200                 205

Arg Lys Lys Met Gln His Thr Val Lys Ile Ser Gly Asp Ala Ser Thr
        210                 215                 220

Lys Ala His Arg Gly Val Lys Ser Val Ile Thr Phe Phe Leu Leu Tyr
225                 230                 235                 240

Ala Ile Phe Ser Leu Ser Phe Phe Ile Ser Val Trp Thr Ser Glu Arg
                245                 250                 255

Leu Glu Glu Asn Leu Ile Ile Leu Ser Gln Val Met Gly Met Ala Tyr
                260                 265                 270

Pro Ser Cys His Ser Cys Val Leu Ile Leu Gly Asn Lys Lys Leu Arg
            275                 280                 285

Gln Ala Ser Leu Ser Val Leu Leu Trp Leu Arg Tyr Met Phe Lys Asp
        290                 295                 300

Gly Glu Pro Ser Gly His Lys Glu Phe Arg Glu Ser Ser
305                 310                 315

<210> SEQ ID NO 3
<211> LENGTH: 921
<212> TYPE: DNA
<213> ORGANISM: Homo sapiens

<400> SEQUENCE: 3
atgctacgtg tagtggaagg catcttcatt tttgttgtag ttagtgagtc agtgtttggg      60
gttttgggga atggatttat tggacttgta aactgcattg actgtgccaa gaataagtta     120
tctacgattg gctttattct caccggctta gctatttcaa gaattttcct gatatggata     180
ataattacag atggatttat acagatattc tctccaaata tatatgcctc cggtaaccta     240
attgaatata ttagttactt tgggtaatt ggtaatcaat caagtatgtg gtttgccacc      300
agcctcagca tcttctattt cctgaagata gcaattttt ccaactacat atttctctgg      360
ttgaagagca gaacaaatat ggttcttccc ttcatgatag tattcttact tatttcatcg     420
ttacttaatt ttgcatacat tgcgaagatt cttaatgatt ataaaatgaa gaatgacaca     480
gtctgggatc tcaacatgta taaaagtgaa tactttatta acagatttt gctaaatctg      540 ggagtcattt tcttctttac actatcccta attacatgta ttttttttaat catttcccttt    600 tggagacaca acaggcagat gcaatcgaat gtgacaggat tgagagactc caacacagaa     660
gctcatgtga aggcaatgaa agtttgata tctttcatca tcctctttat cttgtatttt       720
ataggcatgg ccatagaaat atcatgtttt actgtgcgag aaaacaaact gctgcttatg     780
tttggaatga caaccacagc catctatccc tggggtcact catttatctt aattctagga     840
aacagcaagc taaagcaagc ctcttttgagg gtactgcagc aattgaagtg ctgtgagaaa     900
aggaaaaatc tcagagtcac a                                               921

<210> SEQ ID NO 4
<211> LENGTH: 307
<212> TYPE: PRT
<213> ORGANISM: Homo sapiens

<400> SEQUENCE: 4
```

```
Met Leu Arg Val Val Glu Gly Ile Phe Ile Phe Val Val Ser Glu
1               5                   10                  15

Ser Val Phe Gly Val Leu Gly Asn Gly Phe Ile Gly Leu Val Asn Cys
            20                  25                  30

Ile Asp Cys Ala Lys Asn Lys Leu Ser Thr Ile Gly Phe Ile Leu Thr
            35                  40                  45

Gly Leu Ala Ile Ser Arg Ile Phe Leu Ile Trp Ile Ile Thr Asp
50                  55                  60

Gly Phe Ile Gln Ile Phe Ser Pro Asn Ile Tyr Ala Ser Gly Asn Leu
65                  70                  75                  80

Ile Glu Tyr Ile Ser Tyr Phe Trp Val Ile Gly Asn Gln Ser Ser Met
                85                  90                  95

Trp Phe Ala Thr Ser Leu Ser Ile Phe Tyr Phe Leu Lys Ile Ala Asn
            100                 105                 110

Phe Ser Asn Tyr Ile Phe Leu Trp Leu Lys Ser Arg Thr Asn Met Val
            115                 120                 125

Leu Pro Phe Met Ile Val Phe Leu Leu Ile Ser Ser Leu Leu Asn Phe
130                 135                 140

Ala Tyr Ile Ala Lys Ile Leu Asn Asp Tyr Lys Met Lys Asn Asp Thr
145                 150                 155                 160

Val Trp Asp Leu Asn Met Tyr Lys Ser Glu Tyr Phe Ile Lys Gln Ile
                165                 170                 175

Leu Leu Asn Leu Gly Val Ile Phe Phe Phe Thr Leu Ser Leu Ile Thr
            180                 185                 190

Cys Ile Phe Leu Ile Ile Ser Leu Trp Arg His Asn Arg Gln Met Gln
            195                 200                 205

Ser Asn Val Thr Gly Leu Arg Asp Ser Asn Thr Glu Ala His Val Lys
210                 215                 220

Ala Met Lys Val Leu Ile Ser Phe Ile Ile Leu Phe Ile Leu Tyr Phe
225                 230                 235                 240

Ile Gly Met Ala Ile Glu Ile Ser Cys Phe Thr Val Arg Glu Asn Lys
                245                 250                 255

Leu Leu Leu Met Phe Gly Met Thr Thr Thr Ala Ile Tyr Pro Trp Gly
            260                 265                 270

His Ser Phe Ile Leu Ile Leu Gly Asn Ser Lys Leu Lys Gln Ala Ser
            275                 280                 285

Leu Arg Val Leu Gln Gln Leu Lys Cys Cys Glu Lys Arg Lys Asn Leu
290                 295                 300

Arg Val Thr
305

<210> SEQ ID NO 5
<211> LENGTH: 897
<212> TYPE: DNA
<213> ORGANISM: Homo sapiens

<400> SEQUENCE: 5
atgcttcggt tattctattt ctctgctatt attgcctcag ttattttaaa ttttgtagga      60
atcattatga atctgtttat tacagtggtc aattgcaaaa cttgggtcaa aagccataga     120
atctcctctt ctgataggat tctgttcagc ctgggcatca ccaggtttct tatgctggga     180
ctatttctgg tgaacaccat ctacttcgtc tcttcaaata cggaaaggtc agtctacctg     240
tctgcttttt ttgtgttgtg tttcatgttt ttggactcga gcagtgtctg gtttgtgacc     300
ttgctcaata tcttgtactg tgtgaagatt actaacttcc aacactcagt gtttctcctg     360
```

```
ctgaagcgga atatctcccc aaagatcccc aggctgctgc tggcctgtgt gctgatttct    420
gctttcacca cttgcctgta catcacgctt agccaggcat cacctttttcc tgaacttgtg   480 actacgagaa ataacacatc atttaatatc agtgagggca tcttgtcttt agtggttttct  540 ttggtcttga gctcatctct ccagttcatc attaatgtga cttctgcttc cttgctaata   600
cactccttga ggagacatat acagaagatg cagaaaaatg ccactggttt ctggaatccc   660
cagacggaag ctcatgtagg tgctatgaag ctgatggtct atttcctcat cctctacatt   720
ccatattcag ttgctaccct ggtccagtat ctccccttttt atgcagggat ggatatgggg  780
accaaatcca tttgtctgat ttttgccacc ctttactctc caggacattc tgttctcatt   840
attatcacac atcctaaact gaaaacaaca gcaagaagaa ttcttttgttt caaaaaa     897
```

<210> SEQ ID NO 6
<211> LENGTH: 299
<212> TYPE: PRT
<213> ORGANISM: Homo sapiens

<400> SEQUENCE: 6

```
Met Leu Arg Leu Phe Tyr Phe Ser Ala Ile Ile Ala Ser Val Ile Leu
 1               5                  10                  15

Asn Phe Val Gly Ile Ile Met Asn Leu Phe Ile Thr Val Val Asn Cys
                20                  25                  30

Lys Thr Trp Val Lys Ser His Arg Ile Ser Ser Ser Asp Arg Ile Leu
            35                  40                  45

Phe Ser Leu Gly Ile Thr Arg Phe Leu Met Leu Gly Leu Phe Leu Val
        50                  55                  60

Asn Thr Ile Tyr Phe Val Ser Ser Asn Thr Glu Arg Ser Val Tyr Leu
 65                  70                  75                  80

Ser Ala Phe Phe Val Leu Cys Phe Met Phe Leu Asp Ser Ser Ser Val
                85                  90                  95

Trp Phe Val Thr Leu Leu Asn Ile Leu Tyr Cys Val Lys Ile Thr Asn
            100                 105                 110

Phe Gln His Ser Val Phe Leu Leu Leu Lys Arg Asn Ile Ser Pro Lys
        115                 120                 125

Ile Pro Arg Leu Leu Leu Ala Cys Val Leu Ile Ser Ala Phe Thr Thr
130                 135                 140

Cys Leu Tyr Ile Thr Leu Ser Gln Ala Ser Pro Phe Pro Glu Leu Val
145                 150                 155                 160

Thr Thr Arg Asn Asn Thr Ser Phe Asn Ile Ser Glu Gly Ile Leu Ser
                165                 170                 175

Leu Val Val Ser Leu Val Leu Ser Ser Leu Gln Phe Ile Ile Asn
            180                 185                 190

Val Thr Ser Ala Ser Leu Leu Ile His Ser Leu Arg Arg His Ile Gln
        195                 200                 205

Lys Met Gln Lys Asn Ala Thr Gly Phe Trp Asn Pro Gln Thr Glu Ala
210                 215                 220

His Val Gly Ala Met Lys Leu Met Val Tyr Phe Leu Ile Leu Tyr Ile
225                 230                 235                 240

Pro Tyr Ser Val Ala Thr Leu Val Gln Tyr Leu Pro Phe Tyr Ala Gly
                245                 250                 255

Met Asp Met Gly Thr Lys Ser Ile Cys Leu Ile Phe Ala Thr Leu Tyr
            260                 265                 270
```

-continued

```
Ser Pro Gly His Ser Val Leu Ile Ile Ile Thr His Pro Lys Leu Lys
        275                 280                 285
Thr Thr Ala Lys Lys Ile Leu Cys Phe Lys Lys
        290                 295
```